US008541453B2

(12) United States Patent
Hadida-Ruah et al.

(10) Patent No.: US 8,541,453 B2
(45) Date of Patent: *Sep. 24, 2013

(54) MODULATORS OF ATP-BINDING CASSETTE TRANSPORTERS

(75) Inventors: Sara Sabina Hadida-Ruah, La Jolla, CA (US); Peter Diederik Jan Grootenhuis, San Diego, CA (US); Mark Thomas Miller, San Diego, CA (US); Matthew Hamilton, Hackettstown, NJ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/112,115

(22) Filed: May 20, 2011

(65) Prior Publication Data

US 2011/0306637 A1 Dec. 15, 2011

Related U.S. Application Data

(60) Division of application No. 11/202,278, filed on Aug. 11, 2005, now Pat. No. 7,977,322, which is a continuation-in-part of application No. 11/047,366, filed on Jan. 31, 2005, now abandoned.

(60) Provisional application No. 60/603,503, filed on Aug. 20, 2004, provisional application No. 60/603,564, filed on Aug. 24, 2004.

(51) Int. Cl.
| | | |
|---|---|---|
| C07D 231/40 | (2006.01) |
| C07D 233/88 | (2006.01) |
| C07D 263/48 | (2006.01) |
| C07D 271/113 | (2006.01) |
| C07D 277/46 | (2006.01) |
| C07D 277/54 | (2006.01) |
| C07D 277/82 | (2006.01) |
| C07D 285/135 | (2006.01) |
| C07D 405/12 | (2006.01) |
| C07D 407/12 | (2006.01) |
| C07D 409/12 | (2006.01) |
| C07D 409/14 | (2006.01) |
| C07D 413/12 | (2006.01) |
| C07D 417/04 | (2006.01) |
| C07D 417/06 | (2006.01) |
| C07D 417/12 | (2006.01) |
| C07D 417/14 | (2006.01) |
| C07D 493/10 | (2006.01) |
| A61K 31/454 | (2006.01) |
| A61K 31/427 | (2006.01) |
| A61K 31/4439 | (2006.01) |
| A61K 31/433 | (2006.01) |
| A61K 31/4245 | (2006.01) |
| A61K 31/4178 | (2006.01) |
| A61K 31/422 | (2006.01) |
| A61P 11/00 | (2006.01) |
| A61P 3/00 | (2006.01) |
| A61P 3/06 | (2006.01) |
| A61P 3/10 | (2006.01) |
| A61P 25/28 | (2006.01) |
| A61P 25/00 | (2006.01) |
| A61P 1/12 | (2006.01) |
| A61P 27/02 | (2006.01) |
| A61P 13/12 | (2006.01) |

(52) U.S. Cl.
USPC .......... 514/321; 514/338; 514/363; 514/364; 514/371; 514/377; 514/397; 546/197; 546/270.7; 548/139; 548/143; 548/195; 548/233; 548/311.7

(58) Field of Classification Search
None
See application file for complete search history.

(56) References Cited

U.S. PATENT DOCUMENTS

| | | |
|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |

(Continued)

OTHER PUBLICATIONS

Chan et al., abstract, 2011, http://www.ncbi.nlm.nih.gov/pubmed/21827405.*
Apostoli et al., PPAR Research, 2012, 1-16, FOLUM3 2012.*
ClinicalTrial, 2011, http://www.nature.com/news/2011/110928/full/477526a.html.*
Peter A. Sloane et al., "A Pharmacologic Approach to Acquired Cystic Fibrosis Transmembrane Conductance Regulator Dysfunction in Smoking Related Lung Disease." Jun. 2012, vol. 7, Issue 6, pp. 1-13.
Cristina Bombieri et al., "Complete mutational screening of the CFTR gene in 120 patients with pulmonary disease" Human Genet (1998) 103:718-722.
Marc H. Levin et al., Investigative Opthamology & Visual Science, Apr. 2005, vol. 46, No. 4; pp. 1428-1434.

*Primary Examiner* — Sun Jae Loewe
(74) *Attorney, Agent, or Firm* — Michael J. DiVerdi

(57) ABSTRACT

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

33 Claims, No Drawings

(56) References Cited

U.S. PATENT DOCUMENTS

| | | |
|---|---|---|
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor et al. |
| 2005/0059687 A1 | 3/2005 | Makings et al. |
| 2005/0113423 A1 | 5/2005 | VanGoor et al. |
| 2006/0052358 A1 | 3/2006 | Hadida Ruah et al. |
| 2007/0105833 A1 | 5/2007 | Hadida Ruah et al. |
| 2008/0071095 A1 | 3/2008 | Hadida-Ruah et al. |
| 2008/0306062 A1 | 12/2008 | Hadida Ruah et al. |
| 2009/0105272 A1 | 4/2009 | Grootenhuis et al. |
| 2009/0143381 A1 | 6/2009 | Hadida Ruah et al. |
| 2009/0170905 A1 | 7/2009 | Keshavarz-Shokri et al. |
| 2009/0176839 A1 | 7/2009 | Keshavarz-Shokri et al. |
| 2009/0246820 A1 | 10/2009 | Singh et al. |
| 2009/0253736 A1 | 10/2009 | Hadida-Ruah et al. |
| 2010/0036130 A1 | 2/2010 | Siesel et al. |
| 2010/0074949 A1 | 3/2010 | Rowe et al. |
| 2010/0087490 A1 | 4/2010 | Young et al. |
| 2010/0113508 A1 | 5/2010 | Binch et al. |
| 2010/0113555 A1 | 5/2010 | Ruah et al. |
| 2010/0125090 A1 | 5/2010 | Hadida Ruah et al. |
| 2010/0130547 A1 | 5/2010 | Zhang et al. |
| 2010/0144798 A1 | 6/2010 | Van Goor et al. |
| 2010/0168094 A1 | 7/2010 | Binch et al. |
| 2010/0168158 A1 | 7/2010 | Binch et al. |
| 2010/0249113 A1 | 9/2010 | Hadida Ruah et al. |
| 2010/0249180 A1 | 9/2010 | Gallardo-Godoy et al. |
| 2010/0256184 A1 | 10/2010 | Rowe et al. |
| 2010/0267768 A1 | 10/2010 | DeMattei et al. |
| 2010/0331344 A1 | 12/2010 | Hadida Ruah et al. |
| 2011/0008259 A1 | 1/2011 | Binch et al. |
| 2011/0060024 A1 | 3/2011 | Hadida Ruah et al. |
| 2011/0064811 A1 | 3/2011 | Hurter et al. |
| 2011/0065928 A1 | 3/2011 | Ambhaikar et al. |
| 2011/0071206 A1 | 3/2011 | Ruah et al. |
| 2011/0098311 A1 | 4/2011 | Van Goor et al. |
| 2011/0123449 A1 | 5/2011 | Zhang et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Goor et al. |
| 2011/0263654 A1 | 10/2011 | Keshavarz et al. |
| 2011/0288121 A1 | 11/2011 | Sun et al. |
| 2011/0288122 A1 | 11/2011 | Van Goor et al. |
| 2012/0004216 A1 | 1/2012 | Hadida Ruah et al. |
| 2012/0010257 A1 | 1/2012 | Hadida-Ruah et al. |
| 2012/0015999 A1 | 1/2012 | Alargova et al. |
| 2012/0035179 A1 | 2/2012 | Hadida Ruah et al. |
| 2012/0046330 A1 | 2/2012 | Alargova et al. |
| 2012/0064157 A1 | 3/2012 | Dokou et al. |
| 2012/0071504 A1 | 3/2012 | Yang et al. |
| 2012/0122921 A1 | 5/2012 | DeMattei et al. |
| 2012/0122922 A1 | 5/2012 | Young |
| 2012/0165372 A1 | 6/2012 | DeMattei et al. |
| 2012/0184583 A1 | 7/2012 | Van Goor et al. |
| 2012/0190856 A1 | 7/2012 | Siesel et al. |
| 2012/0203006 A1 | 8/2012 | Siesel et al. |
| 2012/0208841 A1 | 8/2012 | Binch et al. |
| 2012/0214841 A1 | 8/2012 | Hurter et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0259129 A1 | 10/2012 | Ambhaikar et al. |
| 2012/0270869 A1 | 10/2012 | Hadida Ruah et al. |
| 2012/0277268 A1 | 11/2012 | Keshavarz-Shokri et al. |
| 2012/0309758 A1 | 12/2012 | Sheth et al. |
| 2012/0322798 A1 | 12/2012 | Hadida Ruah et al. |

\* cited by examiner

MODULATORS OF ATP-BINDING CASSETTE TRANSPORTERS

CROSS-REFERENCE TO RELATED APPLICATIONS

The present application is a divisional of U.S. patent application Ser. No. 11/202,278, filed Aug. 11, 2005, which is a continuation-in-part of and claims the benefit of priority under 35 U.S.C. §120 of U.S. application Ser. No. 11/047,366, filed Jan. 31, 2005, which claims the benefit of priority under 35 U.S.C. §119 of U.S. Provisional Application No. 60/540,564, filed Jan. 30, 2004, and U.S. Provisional Application No. 60/603,503, filed Aug. 20, 2004, the entire contents of each of the above two applications being is incorporated herein by reference.

TECHNICAL FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeate of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the endoplasmic reticulum ("ER"), and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354:526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl- channels expressed on the basolateral surface of the cell. Secondary active transport of chloride from the luminal side leads to the accumulation of intracellular chloride, which can then passively leave the cell via Cl- channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43 pp 1-7 (2003); Rutishauser, J., et al., Swiss Med Wkly, 132 pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to P-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E-coli* (ETEC) having the K99 pilus antigen. Common viral causes of diarrhea include rotayirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

DESCRIPTION OF FIGURES

Summary of the Invention

It has now been found that compounds of this invention, and pharmaceutically acceptable compositions thereof, are useful as modulators of ABC transporter activity. These compounds have the general formula I:

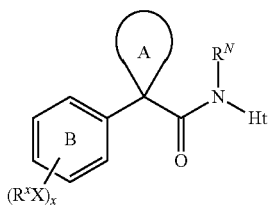

or a pharmaceutically acceptable salt thereof, wherein Ht, $R^N$, ring A, ring B, X, $R^X$, and x are described below.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (di), neurophyseal di, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjögren's disease.

DESCRIPTION OF THE DRAWINGS

FIG. 1 recites the compounds excluded from certain embodiments of the present invention, as described below.

DETAILED DESCRIPTION OF THE INVENTION

I. General Description of Compounds of the Invention

The present invention relates to compounds of formula I useful as modulators of ABC transporter activity:

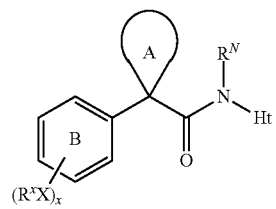

or a pharmaceutically acceptable salt thereof, wherein:

Ht is a 5-membered heteroaromatic ring containing 1-4 heteroatoms selected from O, S, N, or NH, wherein said ring is optionally fused to a 6-membered monocyclic or 10-membered bicyclic, carbocyclic or heterocyclic, aromatic or non-aromatic ring, wherein Ht is optionally substituted with w occurrences of —WR$^W$, wherein w is 0-5;

$R^N$ is H or R;

R is hydrogen or $C_{1-6}$ aliphatic wherein up to two methylene units of R are optionally and independently replaced by —CO—, —CS—, —COCO—, —CONR'—, —CONR'NR'—, —CO$_2$—, —OCO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, NR'SO$_2$—, or —NR'SO$_2$NR'—;

ring A is 3-7 membered monocyclic ring having 0-3 heteroatoms selected from O, S, N, or NH, wherein ring A is optionally substituted with q occurrences of -QR$^Q$;

ring B is optionally fused to 5-6 membered carbocyclic or heterocyclic, aromatic or non-aromatic ring;

each of x, q, and w is independently 0-5; each —X—R$^X$, -Q-R$^Q$, and —W—R$^W$ is independently R';

R' is independently R$^1$, R$^2$, R$^3$, R$^4$, or R$^5$;

R$^1$ is oxo, R$^6$ or ((C1-C4)aliphatic)$_n$-Y;

n is 0 or 1;

Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$; or two $R^1$ on adjacent ring atoms, taken together, form 1,2-methylenedioxy, 1,2-difluoromethylenedioxy, 1,2-ethylenedioxy, or 1,2-tetrafluoroethylenedioxy;

$R^2$ is aliphatic, wherein each $R^2$ optionally comprises up to 2 substituents independently selected from $R^1$, $R^4$, or $R^5$;

$R^3$ is a cycloaliphatic, aryl, heterocyclic, or heteroaryl ring optionally comprising up to 3 substituents, independently selected from $R^1$, $R^2$, $R^4$ or $R^5$;

$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^6C(O)R^6$, $NR^5C(O)R^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^6$, $NR^5SO_2R^5$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

$R^5$ is a cycloaliphatic, aryl, heterocyclic, or heteroaryl ring, optionally comprising up to 3 $R^1$ substituents;

$R^6$ is H or aliphatic, wherein $R^6$ optionally comprises a $R^7$ substituent;

$R^7$ is a cycloaliphatic, aryl, heterocyclic, or heteroaryl ring, and each $R^7$ optionally comprises up to 2 substituents independently chosen from H, (C1-C6)-straight or branched alkyl, ($C_2$-$C_6$) straight or branched alkenyl or alkynyl, 1,2-methylenedioxy, 1,2-ethylenedioxy, or $(CH_2)_n$—Z;

Z is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, N(aliphatic)$R^8$, $NHR^8$, COOH, C(O)O(-aliphatic), or O-aliphatic; and $R^8$ is an amino protecting group.

In another embodiment, the present invention provides compounds of formula I, wherein the compounds set forth in FIG. 1 are excluded.

2. Compounds and Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halogen atoms. The term "halogen" means F, Cl, Br, or I. Examples of haloaliphatic include $-CHF_2$, $-CH_2F$, $-CF_3$, $-CF_2-$, or perhaloalkyl, such as, $-CF_2CF_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $-R^o$; $-OR^o$; $-SR^o$; 1,2-methylene-dioxy; 1,2-ethylenedioxy; phenyl (Ph) optionally substituted with $R^o$; $-O(Ph)$ optionally substituted with $R^o$; $-(CH_2)_{1-2}(Ph)$, optionally substituted with $R^o$; $-CH=CH(Ph)$, optionally substituted with $R^o$; $-NO_2$; $-CN$; $-N(R^o)_2$; $-NR^oC(O)R^o$; $-NR^oC(O)N(R^o)_2$; $-NR^oCO_2R^o$; $-NR^oNR^oC(O)R^o$; $-NR^oNR^oC(O)N(R^o)_2$; $-NR^oNR^oCO_2R^o$; $-C(O)C(O)R^o$; $-C(O)CH_2C(O)R^o$; $-CO_2R^o$; $-C(O)R^o$; $-C(O)N(R^o)_2$; $-OC(O)N(R^o)_2$; $-S(O)_2R^o$; $-SO_2N(R^o)_2$; $-S(O)R^o$; $-NR^oSO_2N(R^o)_2$; $-NR^oSO_2R^o$; $-C(=S)N(R^o)_2$; $-C(=NH)-N(R^o)_2$; or $-(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, $-O(Ph)$, or $-CH_2(Ph)$, or, notwithstanding the definition above, two independent occurrences of $R^o$, on the same substituent or different substituents, taken together with the atom(s) to which each $R^o$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^o$ are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}$ aliphatic), or $haloC_{1-4}aliphatic$, wherein each of the foregoing $C_{1-4}aliphatic$ groups of $R^o$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: $=O$, $=S$, $=NNHR^*$, $=NN(R^*)_2$, $=NNHC(O)R^*$, $=NNHCO_2(alkyl)$, $=NNHSO_2(alkyl)$, or $=NR^*$, where each $R^*$ is independently selected from hydrogen or an optionally substituted $C_{1-6}$ aliphatic. Optional substituents on the aliphatic group of $R^*$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo\ C_{1-4}$ aliphatic), or $halo(C_{1-4}$ aliphatic), wherein each of the foregoing $C_{1-4}aliphatic$ groups of $R^*$ is unsubstituted.

Optional substituents on the nitrogen of a non-aromatic heterocyclic ring are selected from $-R^+$, $-N(R^+)_2$, $-C(O)R^+$, $-CO_2R^+$, $-C(O)C(O)R^+$, $-C(O)CH_2C(O)R^+$, $-SO_2R^+$, $-SO_2N(R^+)_2$, $-C(=S)N(R^+)_2$, $-C(=NH)-N(R^+)_2$, or $-NR^+SO_2R^+$; wherein $R^+$ is hydrogen, an optionally substituted $C_{1-6}$ aliphatic, optionally substituted phenyl, optionally substituted $-O(Ph)$, optionally substituted $-CH_2(Ph)$, optionally substituted $-(CH_2)_{1-2}(Ph)$; optionally substituted $-CH=CH(Ph)$; or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic)$_2$, halogen, $C_{1-4}$ aliphatic, OH, $O(C_{1-4}$ aliphatic), $NO_2$, CN, $CO_2H$, $CO_2(C_{1-4}$ aliphatic), $O(halo\ C_{1-4}$ aliphatic), or halo ($C_{1-4}$ aliphatic), wherein each of the foregoing $C_{1-4}aliphatic$ groups of $R^+$ is unsubstituted.

The term "alkylidene chain" refers to a straight or branched carbon chain that may be fully saturated or have one or more units of unsaturation and has two points of attachment to the rest of the molecule. The term "spirocycloalkylidene" refers to a carbocyclic ring that may be fully saturated or have one or more units of unsaturation and has two points of attachment from the same ring carbon atom to the rest of the molecule.

As detailed above, in some embodiments, two independent occurrences of $R^o$ (or $R^+$, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

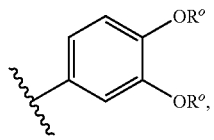

these two occurrences of R° are taken together with the oxygen atoms to which they are bound to form a fused 6-membered oxygen containing ring:

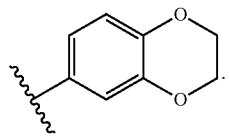 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹³C- or ¹⁴C-enriched carbon are within the scope of this invention. Such compounds are useful, for example, as analytical tools or probes in biological assays.

3. Description of Exemplary Compounds

In some embodiments, R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In some embodiments, each of Q, X, and W is independently a bond or is an optionally substituted $C_1$-$C_6$ alkylidene chain wherein up to two methylene units of Q, W, or X are optionally and independently replaced by —CO—, —CS—, —COCO—, —CONR'—, —CONR'NR'—, —CO₂—, —OCO—, —NR'CO₂—, —O—, —NR'CONR'—, —OCONR'—, —NR'NR', —NR'NR'CO—, —NR'CO—, —S—, —SO, —SO₂—, —NR'—, —SO₂NR'—, NR'SO₂—, or —NR'SO₂NR'—.

In some embodiments, each of $R^X$, $R^Q$, and $R^W$ is independently R', halo, NO₂, CN, CF₃, or OCF₃;

In other embodiments, Q is independently a bond or is an optionally substituted $C_{1-6}$ alkylidene chain wherein one or two non-adjacent methylene units are optionally and independently replaced by O, NR, S, SO₂, COO, or CO, and $R^Q$ is R' or halogen. In still other embodiments, each occurrence of QR$^Q$ is independently —$C_{1-3}$alkyl, —O($C_{1-3}$alkyl), —CF₃, —OCF₃, —SCF₃, —F, —Cl, —Br, or —COOR', —COR', —O(CH₂)₂N(R)(R'), —O(CH₂)N(R)(R'), —CON(R)(R'), —(CH₂)₂OR', —(CH₂)OR', optionally substituted phenyl, —N(R)(R'), —(CH₂)₂N(R)(R'), or —(CH₂)N(R)(R').

In other embodiments, X is independently a bond or is an optionally substituted $C_{1-6}$ alkylidene chain wherein one or two non-adjacent methylene units are optionally and independently replaced by O, NR, S, SO₂, COO, or CO, and $R^X$ is R' or halogen. In still other embodiments, each occurrence of XR$^X$ is independently —$C_{1-3}$alkyl, —O($C_{1-3}$alkyl), —CF₃, —OCF₃, —SCF₃, —F, —Cl, —Br, or —COOR', —COR', —O(CH₂)₂N(R)(R'), —O(CH₂)N(R)(R'), —CON(R)(R'), —(CH₂)₂OR', —(CH₂)OR', optionally substituted phenyl, —N(R)(R'), —(CH₂)₂N(R)(R'), or —(CH₂)N(R)(R').

In other embodiments, W is independently a bond or is an optionally substituted $C_{1-6}$ alkylidene chain wherein one or two non-adjacent methylene units are optionally and independently replaced by O, NR, S, SO₂, COO, or CO, and $R^W$ is R' or halogen. In still other embodiments, each occurrence of WR$^W$ is independently —$C_{1-3}$alkyl, —O($C_{1-3}$alkyl), —CF₃, —OCF₃, —SCF₃, —F, —Cl, —Br, or —COOR', —COR', —O(CH₂)₂N(R)(R'), —O(CH₂)N(R)(R'); —CON(R)(R'), —(CH₂)₂OR', —(CH₂)OR', optionally substituted phenyl, —N(R)(R'), —(CH₂)₂N(R)(R'), or —(CH₂)N(R)(R').

In one embodiment of formula I, R is hydrogen.

In one embodiment, $R^N$ is hydrogen.

In some embodiments, ring A is a 3-7 membered cycloalkyl ring.

In other embodiments, ring A is a 3-7 membered ring containing 1 heteroatom selected from O, NH, or S. Or, ring A contains up two heteroatoms selected from O, S, or NH.

In one embodiment, ring A is selected from:

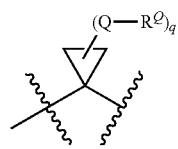

a

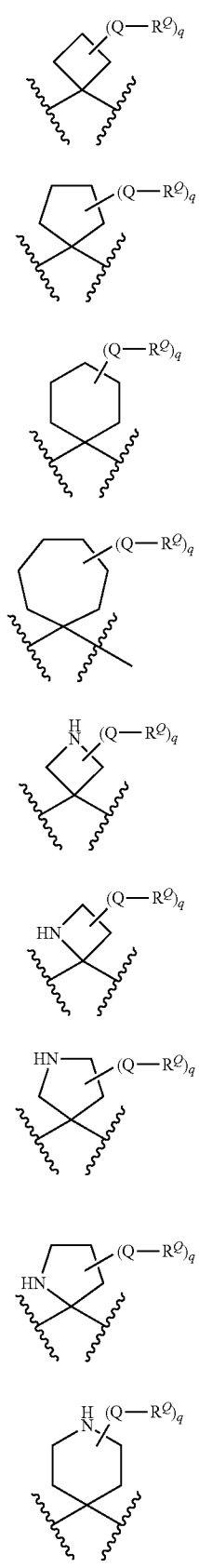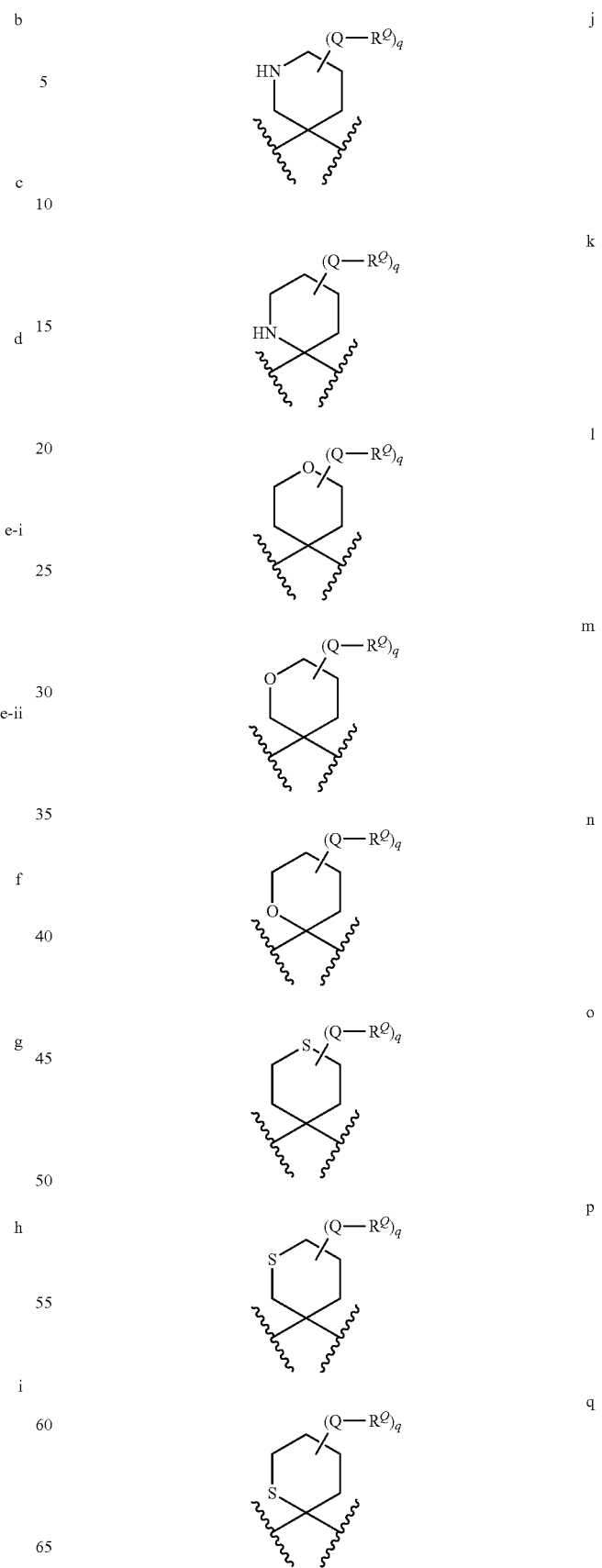

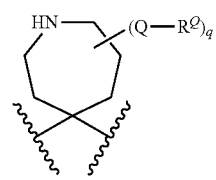
r
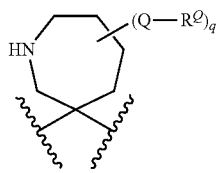
s
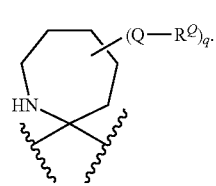
t
In some embodiments, Ht is an optionally substituted 5-membered heteroaromatic ring containing 1-4 heteroatoms selected from O, S, N, or NH, wherein said ring is optionally fused to a phenyl ring.
In certain embodiments, Ht is selected from one of the following rings:
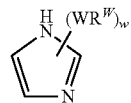
1-a
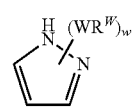
1-b
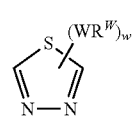
1-c
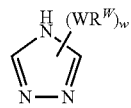
1-d
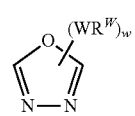
1-e
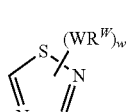
1-f
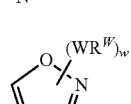
1-g
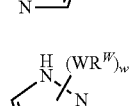
1-h
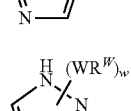
1-i
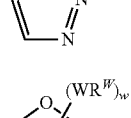
1-j
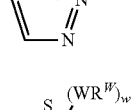
1-k
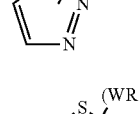
1-l
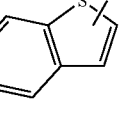
1-m
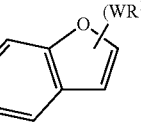
1-n
1-o
1-p
1-q
1-r
1-s
1-t -continued

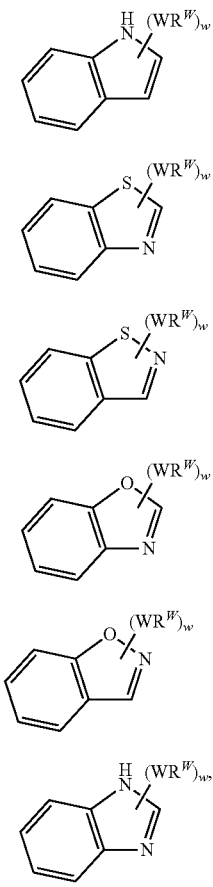

wherein each ring is linked to the remainder of the molecule through a carbon ring atom.

In some embodiments, ring B is fused to 5-6 membered carbocyclic or heterocyclic, aromatic or non-aromatic ring. In certain embodiments, ring B is fused to a five membered heterocyclic ring.

In some embodiments, ring B is optionally substituted phenyl.

According to one embodiment, the present invention provides compounds of formula IIA:

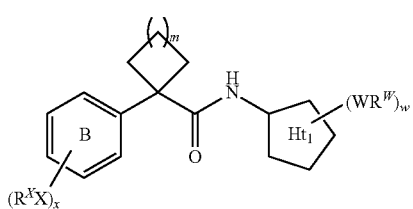

IIA wherein:
m is 0-4;
Ht$_1$ is a 5-membered heteroaromatic ring containing 1-4 heteroatoms selected from O, S, N, or NH, wherein said ring is optionally fused to a phenyl or 6-membered heteroaromatic ring;
ring B is optionally fused to 5-6 membered carbocyclic or heterocyclic, aromatic or non-aromatic ring;

X, R$^X$, x, W, R$^W$, and w are as defined above.

In some embodiments of formula IIA, m is 0. In other embodiments, m is 1. In yet other embodiments, m is 2. Or, m is 3. In certain other embodiments, m is 4.

In one embodiment of formula IIA, Ht$_1$ is an optionally substituted 5-membered heteroaromatic ring containing 1-4 heteroatoms selected from O, S, N, or NH.

In certain embodiments of formula IIA, Ht$^1$ is selected from:

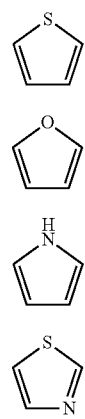

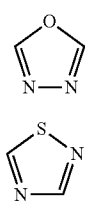

| | |
|---|---|
| 1-n |  |
| 1-o | 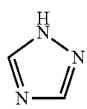 |
| 1-p | 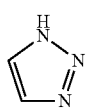 |
| 1-q | 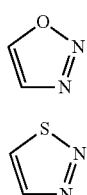 |
| 1-r | 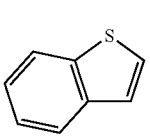 |
| 1-s | 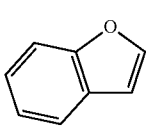 |
| 1-t | 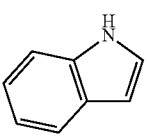 |
| 1-u | 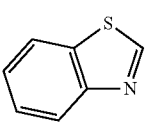 |
| 1-v | 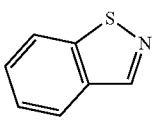 |
| 1-w | 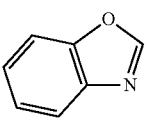 |
| 1-x | 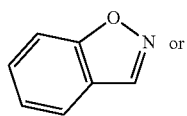 |
| 1-y | 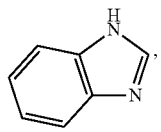 |
| 1-z | | wherein each ring is linked to the remainder of the molecule through a carbon ring atom.

Preferred $Ht_1$ include 1-d, 1-f, 1-j, 1-l, and 1-v rings above.

In certain embodiments of formula IIA, ring B is phenyl optionally substituted with up to x occurrences of X—$R^X$. In other embodiments, ring B is fused with a 5 membered ring, such as, methylenedioxy, imidazolyl, triazolyl, etc.

In certain embodiments of formula IIA, x is 0-3. Preferably, x is 0-2.

According to another embodiment, the present invention provides compounds of formula IIIA or formula IIIB:

IIIA

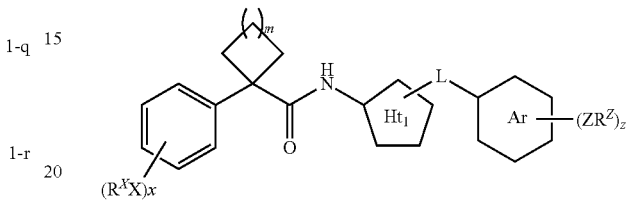

IIIB

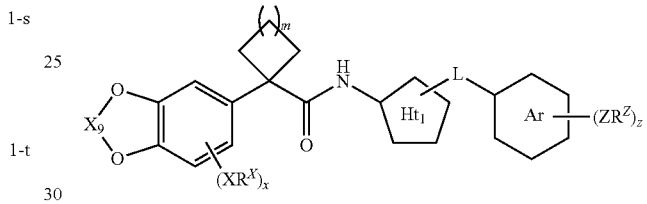

wherein:

m is 0 to 4;

Ar is phenyl or a six-membered heteroaromatic ring;

L is a bond, O, S, SO, $SO_2$, C(O), NR', $C_{1-4}$ aliphatic, or $CHR^L$; $R^L$ is —OR', —SR', —SOR', —$SO_2$R', or —N(R')$_2$; or

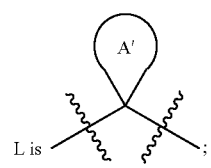 [SMILES: *C(*)(C)C ; "L is" ; ";"]

wherein ring A' is a 3-7 membered monocyclic ring having 0-3 heteroatoms selected from O, S, N, or NH, wherein ring A' is optionally substituted with q occurrences of -$QR^Q$;

R' is as defined above;

$X_9$ is $CH_2$, $CF_2$, $CH_2$—$CH_2$, or $CF_2$—$CF_2$;

$Ht_1$ is a 5-membered heteroaromatic ring containing 1-4 heteroatoms selected from O, S, N, or NH, wherein said ring is optionally fused to a phenyl ring; and z, Z, and $R^Z$ are as defined for x, X, and RX, respectively.

In certain embodiments of formula MA or formula MB, $Ht^1$ is selected from:

1-a

-continued
1-b 
1-c 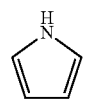
1-d 
1-e 
1-f 
1-g 
1-h 
1-h′ 
1-i 
1-j 
1-k 
1-l 
1-m 
1-n 
1-o 
1-p
1-q
1-r
1-s
1-t
1-u
1-v
1-w
1-x
1-y or
1-z
wherein each ring is linked to the remainder of the molecule through a carbon ring atom.
Preferred $Ht_1$ in formula IIIA or formula IIIB include 1-d, 1-f, 1-j, 1-l, and 1-v rings above.
In certain embodiments of formula IIIA or formula IIIB ring Ar is selected from:

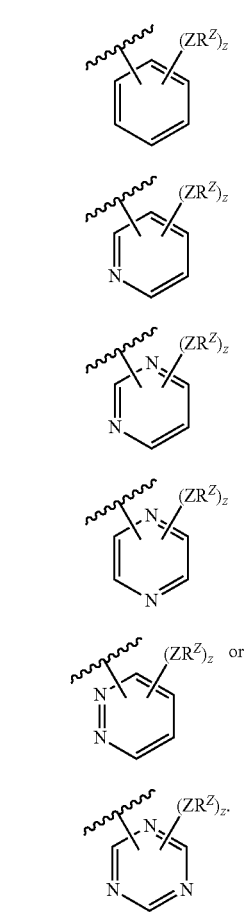

In certain embodiments of formula IIIA or formula IIIB, m is 0. In other embodiments thereof, m is 1. In yet other embodiments thereof, m is 2. Or, m is 3. In certain other embodiments thereof, m is 4.

According to another embodiment, the present invention provides compounds of formula IVA or formula IVB:

IVA

IVB wherein:

L is a bond, O, S, SO, $SO_2$, C(O), NR', $C_{1-4}$ aliphatic, or $CHR^L$;

$R^L$ is —OR', —SR', —SOR', —$SO_2$R', or —N(R')$_2$; or

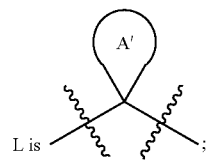 [SMILES: *C(*)(C)C ; "L is" ; ";"]

L is wherein ring A' is a 3-7 membered monocyclic ring having 0-3 heteroatoms selected from O, S, N, or NH, wherein ring A' is optionally substituted with q occurrences of -$QR^Q$;

R' is as defined above;

$X_9$ is $CH_2$, $CF_2$, $CH_2$—$CH_2$, or $CF_2$—$CF_2$;

$X^1$ is O, S, or NR;

R is hydrogen or $C_{1-4}$ aliphatic; and each of $X^2$ and $X^3$ is independently selected from CH or N.

According to one embodiment of the present invention, L is —$CH_2$—, thus providing compounds of formula IVA-1 or formula IVB-1:

IVA-1

IVB-1

According to one embodiment of formula IVA-1 or formula IVB-1, $X^1$ is S, $X^2$ is N, and $X^3$ is CH.

According to another embodiment of formula IVA-1 or formula IVB-1, $X^1$ is S, $X^2$ and $X^3$ both are N.

According to one embodiment of formula IVA-1 or formula IVB-1, $X^1$ is S, $X^2$ is CH, and $X^3$ is N.

According to one embodiment of formula IVA-1 or formula IVB-1, $X^1$ is O, $X^2$ is N, and $X^3$ is CH.

According to another embodiment of formula IVA-1 or formula IVB-1, $X^1$ is O, $X^2$ and $X^3$ both are N.

According to one embodiment of formula IVA-1 or formula IVB-1, $X^1$ is O, $X^2$ is CH, and $X^3$ is N.

According to one embodiment of formula IVA-1 or formula IVB-1, $X^1$ is NR, $X^2$ is N, and $X^3$ is CH. In one embodiment, R is hydrogen. Or, R is $C_{1-4}$ alkyl.

According to another embodiment of formula IVA-1 or formula IVB-1, $X^1$ is NR, $X^2$ and $X^3$ both are N. In one embodiment, R is hydrogen. Or, R is $C_{1-4}$ alkyl.

According to one embodiment of formula IVA-1 or formula IVB-1, $X^1$ is NR, $X^2$ is CH, and $X^3$ is N. In one embodiment, R is hydrogen. Or, R is $C_{1-4}$ alkyl.

According to one embodiment of the present invention, L is —C(O)—, thus providing compounds of formula IVA-2 or formula IVB-2:

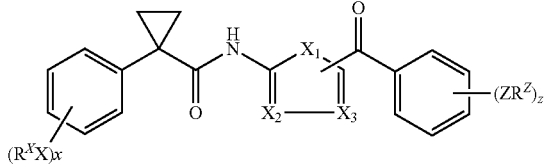

IVA-2

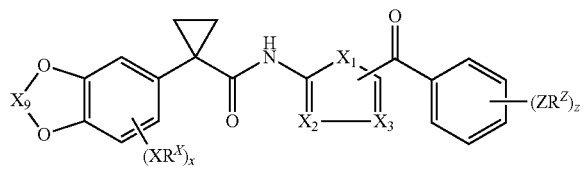

IVB-2

According to one embodiment of formula IVA-2 or formula IVB-2, $X^1$ is S, $X^2$ is N, and $X^3$ is CH.

According to another embodiment of formula IVA-2 or formula IVB-2, $X^1$ is S, $X^2$ and $X^3$ both are N.

According to one embodiment of formula IVA-2 or formula IVB-2, $X^1$ is S, $X^2$ is CH, and $X^3$ is N.

According to one embodiment of formula IVA-2 or formula IVB-2, $X^1$ is O, $X^2$ is N, and $X^3$ is CH.

According to another embodiment of formula IVA-2 or formula IVB-2, $X^1$ is O, $X^2$ and $X^3$ both are N.

According to one embodiment of formula IVA-2 or formula IVB-2, $X^1$ is O, $X^2$ is CH, and $X^3$ is N.

According to one embodiment of formula IVA-2 or formula IVB-2, $X^1$ is NR, $X^2$ is N, and $X^3$ is CH. In one embodiment, R is hydrogen. Or, R is $C_{1-4}$ alkyl.

According to another embodiment of formula IVA-2 or formula IVB-2, $X^1$ is NR, $X^2$ and $X^3$ both are N. In one embodiment, R is hydrogen. Or, R is $C_{1-4}$ alkyl.

According to one embodiment of formula IVA-2 or formula IVB-2, $X^1$ is NR, $X^2$ is CH, and $X^3$ is N. In one embodiment, R is hydrogen. Or, R is $C_{1-4}$ alkyl.

According to another embodiment, L is S, SO, or $SO_2$, thus providing compounds of formula IVA-3 or formula IVB-3:

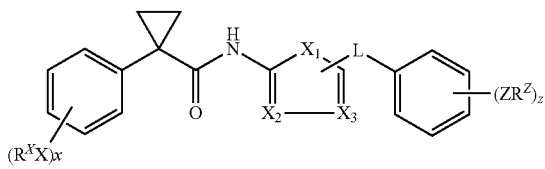

IVA-3

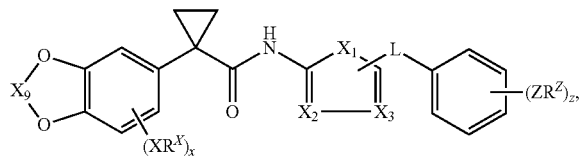

IVB-3 wherein L is S, SO, or $SO_2$.

According to one embodiment of formula IVA-3 or formula IVB-3, $X^1$ is S, $X^2$ is N, and $X^3$ is CH.

According to another embodiment of formula IVA-3 or formula IVB-3, $X^1$ is S, $X^2$ and $X^3$ both are N.

According to one embodiment of formula IVA-3 or formula IVB-3, $X^1$ is S, $X^2$ is CH, and $X^3$ is N.

According to one embodiment of formula IVA-3 or formula IVB-3, $X^1$ is O, $X^2$ is N, and $X^3$ is CH.

According to another embodiment of formula IVA-3 or formula IVB-3, $X^1$ is O, $X^2$ and $X^3$ both are N.

According to one embodiment of formula IVA-3 or formula IVB-3, $X^1$ is O, $X^2$ is CH, and $X^3$ is N.

According to one embodiment of formula IVA-3 or formula IVB-3, $X^1$ is NR, $X^2$ is N, and $X^3$ is CH. In one embodiment, R is hydrogen. Or, R is $C_{1-4}$ alkyl.

According to another embodiment of formula IVA-3 or formula IVB-3, $X^1$ is NR, $X^2$ and $X^3$ both are N. In one embodiment, R is hydrogen. Or, R is $C_{1-4}$ alkyl.

According to one embodiment of formula IVA-3 or formula IVB-3, $X^1$ is NR, $X^2$ is CH, and $X^3$ is N. In one embodiment, R is hydrogen. Or, R is $C_{1-4}$ alkyl.

According to another embodiment, L is O, thus providing compounds of formula IVA-4 or formula IVB-4:

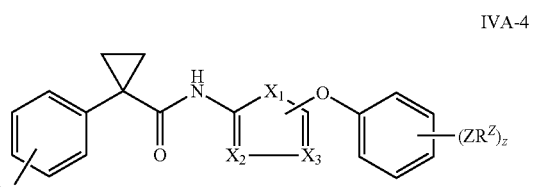

IVA-4

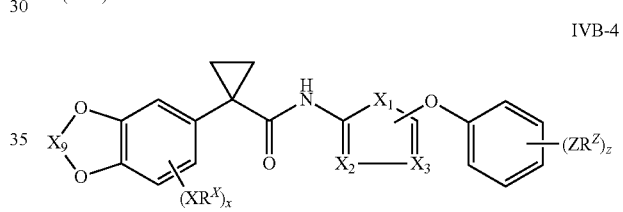

IVB-4

According to one embodiment of formula IVA-4 or formula IVB-4, $X^1$ is S, $X^2$ is N, and $X^3$ is CH.

According to another embodiment of formula IVA-4 or formula IVB-4, $X^1$ is S, $X^2$ and $X^3$ both are N.

According to one embodiment of formula IVA-4 or formula IVB-4, $X^1$ is S, $X^2$ is CH, and $X^3$ is N.

According to one embodiment of formula IVA-4 or formula IVB-4, $X^1$ is O, $X^2$ is N, and $X^3$ is CH.

According to another embodiment of formula IVA-4 or formula IVB-4, $X^1$ is O, $X^2$ and $X^3$ both are N.

According to one embodiment of formula IVA-4 or formula IVB-4, $X^1$ is O, $X^2$ is CH, and $X^3$ is N.

According to one embodiment of formula IVA-4 or formula IVB-4, $X^1$ is NR, $X^2$ is N, and $X^3$ is CH. In one embodiment, R is hydrogen. Or, R is $C_{1-4}$ alkyl.

According to another embodiment of formula IVA-4 or formula IVB-4, $X^1$ is NR, $X^2$ and $X^3$ both are N. In one embodiment, R is hydrogen. Or, R is $C_{1-4}$ alkyl.

According to one embodiment of formula IVA-4 or formula IVB-4, $X^1$ is NR, $X^2$ is CH, and $X^3$ is N. In one embodiment, R is hydrogen. Or, R is $C_{1-4}$ alkyl.

According to another embodiment, L is a bond, thus providing compounds of formula IVA-5, formula IVB-5 or formula IVA-6, formula IVB-6:

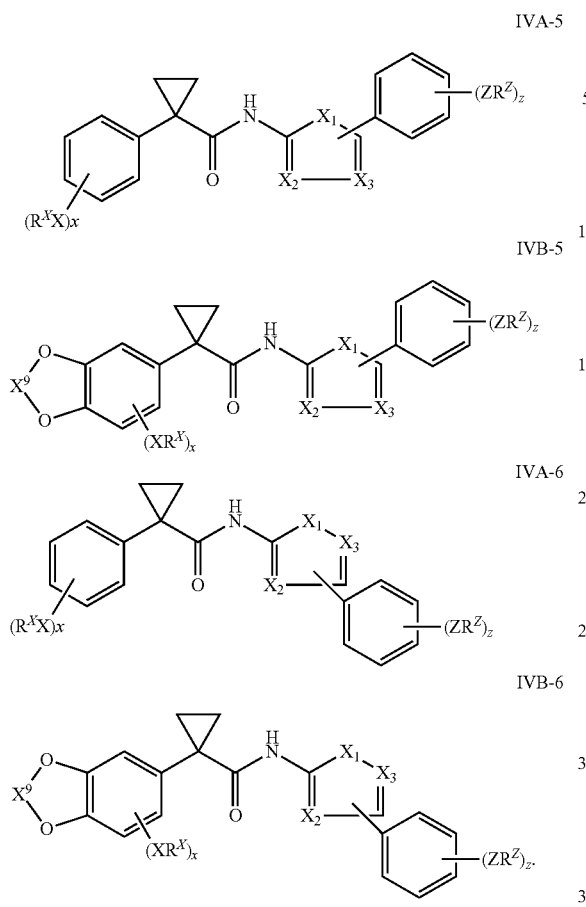

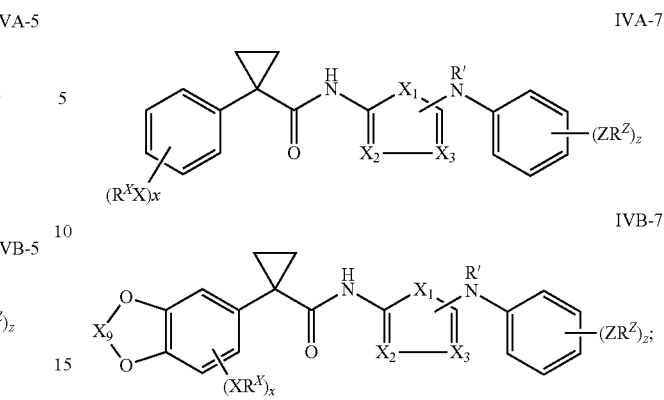

According to one embodiment of formula IVA-5 or IVB-5, $X^1$ is S, $X^2$ is N, and $X^3$ is CH.

According to another embodiment of formula IVA-5 or IVB-5, $X^1$ is S, $X^2$ and $X^3$ both are N.

According to one embodiment of formula IVA-5 or IVB-5, $X^1$ is S, $X^2$ is CH, and $X^3$ is N.

According to one embodiment of formula IVA-5 or IVB-5, $X^1$ is O, $X^2$ is N, and $X^3$ is CH.

According to another embodiment of formula IVA-5 or IVB-5, $X^1$ is O, $X^2$ and $X^3$ both are N.

According to one embodiment of formula IVA-5 or IVB-5, $X^1$ is O, $X^2$ is CH, and $X^3$ is N.

According to one embodiment of formula IVA-5 or IVB-5, $X^1$ is NR, $X^2$ is N, and $X^3$ is CH. In one embodiment, R is hydrogen. Or, R is $C_{1-4}$ alkyl.

According to another embodiment of formula IVA-5 or IVB-5, $X^1$ is NR, $X^2$ and $X^3$ both are N. In one embodiment, R is hydrogen. Or, R is $C_{1-4}$ alkyl.

According to one embodiment of formula IVA-5 or IVB-5, $X^1$ is NR, $X^2$ is CH, and $X^3$ is N. In one embodiment, R is hydrogen. Or, R is $C_{1-4}$ alkyl.

According to one embodiment of formula IVA-6 or IVB-6, $X^1$ is S, $X^2$ is N, and $X^3$ is CH.

According to one embodiment of formula IVA-6 or IVB-6, $X^1$ is O, $X^2$ is N, and $X^3$ is CH.

According to one embodiment of formula IVA-6 or IVB-6, $X^1$ is O, $X^2$ is CH, and $X^3$ is N.

According to another embodiment, L is —NR'—, thus providing compounds of formula IVA-7 or formula IVB-7:

wherein:
R' is hydrogen or $R^D$;
$R^D$ is $C_{1-6}$ aliphatic optionally substituted with —OH, —O($C_{1-4}$aliphatic), —S($C_{1-4}$aliphatic), —$CF_3$, —$OCF_3$, —$SCF_3$, halo, $NH_2$, NHR, $N(R)_2$, C(O)OH, C(O)O($C_{1-4}$aliphatic), NHC(O)($C_{1-4}$aliphatic), or a 3-7 membered heterocyclic ring containing up to 4 heteroatoms selected from O, N, or S, wherein said ring is optionally substituted with up to 2 substituents selected from oxo or $(C_{1-4}$aliphatic$)_p$-Y;
p is 0 or 1;
Y is halo, CN, $NO_2$, $CF_3$, $OCF_3$, OR, SR, $NH_2$, NHR, $N(R)_2$, COOH, or COOR;
R is hydrogen or $C_{1-4}$ aliphatic;

According to one embodiment of formula IVA-7 or formula IVB-7, $X^1$ is S, $X^2$ is N, and $X^3$ is CH.

According to another embodiment of formula IVA-7 or formula IVB-7, $X^1$ is S, $X^2$ and $X^3$ both are N.

According to one embodiment of formula IVA-7 or formula IVB-7, $X^1$ is S, $X^2$ is CH, and $X^3$ is N.

According to one embodiment of formula IVA-7 or formula IVB-7, $X^1$ is O, $X^2$ is N, and $X^3$ is CH.

According to another embodiment of formula IVA-7 or formula IVB-7, $X^1$ is O, $X^2$ and $X^3$ both are N.

According to one embodiment of formula IVA-7 or formula IVB-7, $X^1$ is O, $X^2$ is CH, and $X^3$ is N.

According to one embodiment of formula IVA-7 or formula IVB-7, $X^1$ is NR, $X^2$ is N, and $X^3$ is CH. In one embodiment, R is hydrogen. Or, R is $C_{1-4}$ alkyl.

According to another embodiment of formula IVA-7 or formula IVB-7, $X^1$ is NR, $X^2$ and $X^3$ both are N. In one embodiment, R is hydrogen. Or, R is $C_{1-4}$ alkyl.

According to one embodiment of formula IVA-7 or formula IVB-7, $X^1$ is NR, $X^2$ is CH, and $X^3$ is N. In one embodiment, R is hydrogen. Or, R is $C_{1-4}$ alkyl.

According to another embodiment, the present invention provides compounds of formula VA-1, formula VA-2, formula VA-3, or formula VA-4:

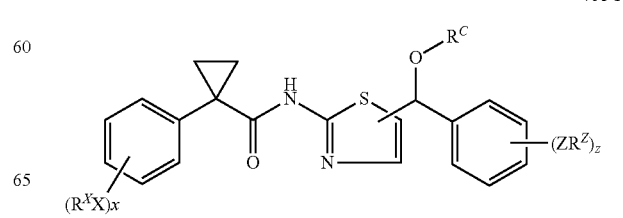

-continued

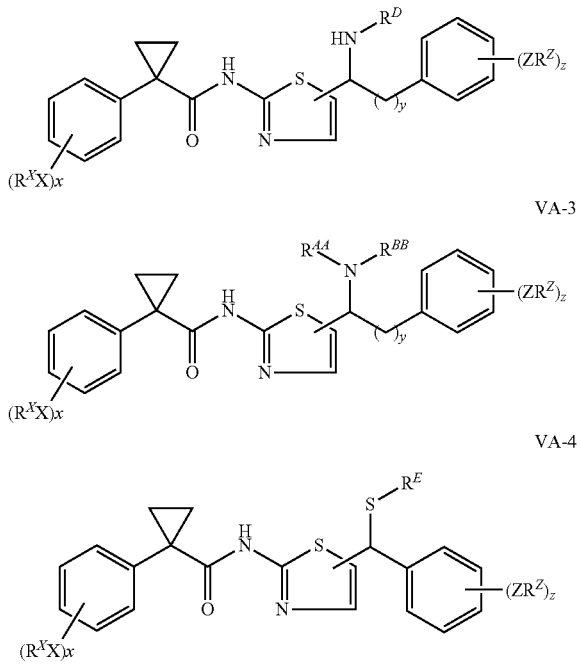

VA-2

VA-3

VA-4 wherein:
each of $R^{AA}$, $R^{BB}$, $R^C$, $R^D$ and $R^E$ is independently hydrogen, C1-C6 aliphatic, C3-C7 cycloalkyl, (C3-C7-cycloalkyl)-C1-C6 aliphatic, (C3-C7-cycloalkenyl)-C1-C6-aliphatic, (3-7-membered heterocycyl), (3-7-membered heterocycyl)-C1-C6-aliphatic, (3-6-membered heteroaryl)-C1-C6 aliphatic, wherein said aliphatic, cycloalkyl, cycloalkenyl, heterocyclyl, or heteroaryl is optionally substituted with up to three substituents selected from OH, —O($C_{1-4}$aliphatic), —$CF_3$, —$OCF_3$, —$SCF_3$, halo, $NH_2$, NHR, $N(R)_2$, or (C1-C4 aliphatic)$_p$-Y;

p is 0 or 1;
y is 0 or 1;
Y is hydrogen, halo, CN, $NO_2$, $CF_3$, $OCF_3$, OR, SR, $NH_2$, NHR, $N(R)_2$, NHC(O)R, COOH, or COOR;
R is hydrogen or $C_{1-4}$ aliphatic; or
$R^{AA}$ and $R^{BB}$, taken together with the nitrogen atom, is a 3-7 membered heterocyclic ring containing up to 4 heteroatoms selected from O, N, or S, wherein said ring is optionally substituted with up to 2 substituents selected from oxo or (C1-C4 aliphatic)$_p$-Y; and
wherein up to two methylene groups in any said aliphatic above are optionally and independently replaced with O, S, C(O), NH, or N(C1-C6 allyl).

In one embodiment, y is 0. In another embodiment, y is 1.
In certain embodiments, $R^C$ is $C_{1-4}$ alkyl optionally substituted with up to two substituents selected from —OH, —O($C_{1-4}$alkyl), NH($C_{1-4}$ alkyl), or N($C_{1-4}$ alkyl)$_2$. In other embodiments, $R^C$ is $C_{1-4}$ alkyl optionally substituted with 5-6 membered heterocyclic ring containing up to 2 heteroatoms selected from O, N, or S, wherein said ring is optionally substituted with up to 2 substituents selected from oxo, ($C_{1-4}$ aliphatic), ($C_{1-4}$ aliphatic)-Y, wherein Y is halo, —OH, or —O($C_{1-4}$ alkyl).

Preferred embodiments of $R^C$ in the present invention include hydrogen, methyl, ethyl, —$(CH_2)_2$-(4-hydroxy-1-piperidyl), —$(CH_2)_3$-(4-hydroxy-1-piperidyl), —$(CH_2)_4$-(4-hydroxy-1-piperidyl), ethylmethylamino-ethyl, 2-hydroxyethyl, 3-hydroxypropyl, 4-hydroxybutyl, 2-methoxyethyl, isopropyl, (2-methoxymethyl-1-pyrrolidinyl)ethyl, tetrahydrofuran-2-ylmethyl, tetrahydrofuran-3-ylmethyl, (pyrrolidin-2-one-5-yl)methyl, (pyrrolidin-1-yl)ethyl, dimethylaminoethyl, 1-piperidylethyl, allyl, n-propyl, diisopropylaminoethyl, and (N-morpholino)ethyl.

In one embodiment of formula VA-1:
a. z is 0-2 and $ZR^Z$ together is selected from halo, OMe, OEt, CN, C(O)$NH_2$, Me, Et, $NH_2$, COOH, $SO_2$Me, $CF_3$, $OCF_3$, difluoromethylenedioxy, N(Me)$_2$, or N(Et)$_2$;
b. x is 0-2 and XRx together is selected from halo, $CF_3$, OH, OMe, OEt, CN, $CH_2NH_2$, $CH_2$N(Et)$_2$, 1,2,4-triazol-1-yl, O($CH_2$)$_2$OMe, morpholin-4-yl, C(O)NH($CH_2$)$_2$OH, OC(O)NHEt, NHS(O)$_2$Me, piperazin-1-yl, NHC(O)$CH_2$N(Me)$_2$, C(O)NH(4-methyl-1,3-oxazol-2-yl), C(O)$NH_2$, Me, Et, $NH_2$, COOH, $SO_2$Me, N(Me)$_2$, N(Et)$_2$, $OCF_3$, or SMe; and
c. $R^C$ is hydrogen, methyl, ethyl, —$(CH_2)_2$-(4-hydroxy-1-piperidyl), —$(CH_2)_3$-(4-hydroxy-1-piperidyl), —$(CH_2)_4$-(4-hydroxy-1-piperidyl), ethylmethylamino-ethyl, 2-hydroxyethyl, 3-hydroxypropyl, 4-hydroxybutyl, 2-methoxyethyl, isopropyl, (2-methoxymethyl-1-pyrrolidinyl)ethyl, tetrahydrofuran-2-ylmethyl, tetrahydrofuran-3-ylmethyl, (pyrrolidin-2-one-5-yl)methyl, (pyrrolidin-1-yl)ethyl, dimethylaminoethyl, 1-piperidylethyl, allyl, n-propyl, diisopropylaminoethyl, or (N-morpholino)ethyl.

In one embodiment of formula VA-2, $R^D$ is hydrogen.
In one embodiment, $R^D$ is optionally substituted C1-C6 aliphatic. Exemplary embodiments include C1-C6 alkyl, optionally substituted with up two substituents selected from OH, —O(C1-C4 alkyl), acetamido, $NH_2$, NH(C1-C4 alkyl), or N(C1-C4 alkyl)$_2$.

In another embodiment, $R^D$ is an optionally substituted C3-C6 cycloalkyl, cycloalkenyl ring, (C3-C6 cycloalkyl)-C1-C6 aliphatic or (C3-C6 cycloalkyl)-cycloalkenyl ring. Exemplary embodiments include cyclopropyl, cyclobutyl, cyclopentyl, cyclohexyl, cyclohexenyl ethyl or cyclohexylmethyl.

In one embodiment, $R^D$ is optionally substituted 3-7 membered heterocyclyl or (3-7 membered heterocyclyl)-C1-C6 aliphatic, wherein said heterocyclyl contains up to 2 heteroatoms selected from O, S, or N. Exemplary embodiments include (N-methyl-pyrrolidin-2-yl)-ethyl, pyrrolidin-1-ylethyl, isoxazolin-3-one-4-yl, 2,2-dimethyl-tetrahydro-2H-pyran-4-yl, tetrahydrofuran-2-yl-methyl, morpholin-4-yl-ethyl, morpholin-4-yl-propyl, or piperidin-1-yl-ethyl.

In another embodiment, $R^D$ is optionally substituted 5-6 membered heteroaryl or (5-6-membered heteroaryl)-C1-C6 aliphatic, wherein said heteroaryl contains up to 2 heteroatoms selected from O, S, or N. Exemplary embodiments include imidazolyl-propyl, furanyl-methyl, or pyridinyl-ethyl.

In certain embodiments, $R^D$ is $C_{1-4}$ alkyl optionally substituted with —OH, —O($C_{1-4}$alkyl), NH($C_{1-4}$ alkyl), or N($C_{1-4}$ alkyl)$_2$. In other embodiments, $R^D$ is $C_{1-4}$ alkyl optionally substituted with 5-6 membered heterocyclic ring containing up to 2 heteroatoms selected from O, N, or S, wherein said ring is optionally substituted with up to 2 substituents selected from oxo, ($C_{1-4}$ aliphatic), ($C_{1-4}$ aliphatic)-Y, wherein Y is halo, —OH, or —O($C_{1-4}$ alkyl).

Preferred embodiments of $R^D$ include (N-morpholino)ethyl, (N-morpholino)propyl, dimethylaminoethyl, or (N-piperidyl)ethyl. Or, $R^D$ is as shown for any of the compounds in Table 1 herein.

In one embodiment of formula VA-2:
a. z is 0-2 and $ZR^Z$ together is selected from halo, OMe, OEt, $CF_3$, CN, C(O)$NH_2$, Me, Et, $NH_2$, COOH, $SO_2$Me, $OCF_3$, difluoromethylenedioxy, N(Me)$_2$, or N(Et)$_2$;

b. x is 0-2 and XR$^X$ together is selected from halo, CF$_3$, OH, OMe, OEt, CN, CH$_2$NH$_2$, CH$_2$N(Et)$_2$, 1,2,4-triazol-1-yl, O(CH$_2$)$_2$OMe, morpholin-4-yl, C(O)NH(CH$_2$)$_2$OH, OC(O)NHEt, NHS(O)$_2$Me, piperazin-1-yl, NHC(O)CH$_2$N(Me)$_2$, C(O)NH(4-methyl-1,3-oxazol-2-yl), C(O)NH$_2$, Me, Et, NH$_2$, COOH, SO$_2$Me, N(Me)$_2$, N(Et)$_2$, OCF$_3$, or SMe; and c. y is 0;

d. R$^D$ is (N-morpholino)ethyl, (N-morpholino)propyl, dimethylaminoethyl, or (N-piperidyl)ethyl or R$^D$ is as shown for any of the compounds in Table 1 herein.

In one embodiment, one of R$^{AA}$ and R$^{BB}$ is C1-C4 alkyl, and the other of R$^{AA}$ and R$^{BB}$ is selected from C1-C4 alkyl, C2-C4 alkenyl, C3-C6 cycloalkyl, (C3-C6 cycloalkyl)-C1-C4 alkyl, wherein said alkyl, alkenyl, or cycloalkenyl has up to 2 substituents selected from OH or —O(C1-C4 alkyl).

In one embodiment, R$^{AA}$ and R$^{BB}$, taken together with the nitrogen atom, forms a ring selected from pyrrolidinyl, piperidinyl, piperazinyl, or morpholinyl, wherein said ring is optionally substituted with up to two substituents selected from hydroxy, C1-C4 alkyl, C2-C4 alkenyl, COOH, acetoxy, acetyl, hydroxymethyl, hydroxyethyl, methoxymethyl, methoxyethyl, allyl, ethylenedioxy, or C(O)NH$_2$.

In certain embodiments of formula VA-3, each of R$^{AA}$ and R$^{BB}$ is independently C$_{1-4}$ alkyl optionally substituted with up to two substituents selected from —OH, —O(C$_{1-4}$alkyl), NH(C$_{1-4}$ alkyl), or N(C$_{1-4}$ alkyl)$_2$. In other embodiments, R$^{AA}$ and R$^{BB}$ is C$_{1-4}$ alkyl optionally substituted with 5-6 membered heterocyclic ring containing up to 2 heteroatoms selected from O, N, or S, wherein said ring is optionally substituted with up to 2 substituents selected from oxo, (C$_{1-4}$ aliphatic), (C$_{1-4}$ aliphatic)-Y, wherein Y is halo, —OH, or —O(C$_{1-4}$ alkyl).

Preferred R$^{AA}$ and R$^{BB}$ include Me, Et, propyl, butyl, allyl, hydroxyethyl, dihydroxypropyl, cyclohexyl, cyclopropylmethyl, or diisopropylaminoethyl.

In certain embodiments, R$^{AA}$ and R$^{BB}$, taken together with the nitrogen atom, is selected from:

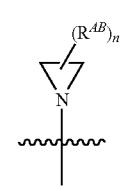

ab-1

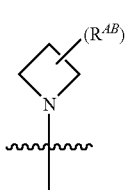

ab-2

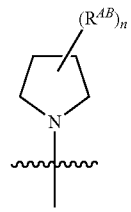

ab-3

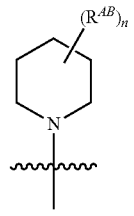

ab-4

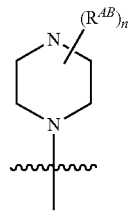

ab-5

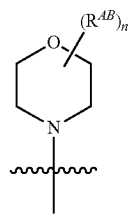

ab-6

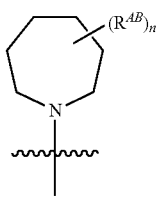

ab-7

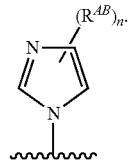

ab-8

Preferred R$^{AB}$ include methoxymethyl, methoxyethyl, acetoxy, allyl, methyl, —OH, hydroxymethyl, hydroxyethyl, ethylenedioxy, COOH, CONH$_2$, or C(O)CH$_3$.

According to one embodiment of formula VA-4, R$^E$ is independently C$_{1-6}$ aliphatic optionally substituted with —OH, —O(C$_{1-4}$aliphatic), —S(C$_{1-4}$aliphatic), —CF$_3$, —OCF$_3$, —SCF$_3$, halo, NH$_2$, NHR, N(R)$_2$, C(O)OH, C(O)O(C$_{1-4}$aliphatic), or NHC(O)(C$_{1-4}$aliphatic). Preferred embodiments of R$^E$ include —(CH$_2$)$_2$OH, —(CH$_2$)$_3$OH, —(CH$_2$)$_4$OH, —(CH$_2$)$_2$NH$_2$, —(CH$_2$)$_2$NMe$_2$, —(CH$_2$)$_2$NEt$_2$, —(CH$_2$)$_2$NHC(O)Me, —(CH$_2$)$_2$COOH, —(CH$_2$)$_2$COOH, —(CH$_2$)COOMe, —(CH$_2$)CH(NH$_2$)COOH, or —(CH$_2$)$_2$CH(NH$_2$)COOH.

According to another embodiment, the present invention provides compounds of formula VB-1, formula VB-2, formula VB-3, of formula VB-4:

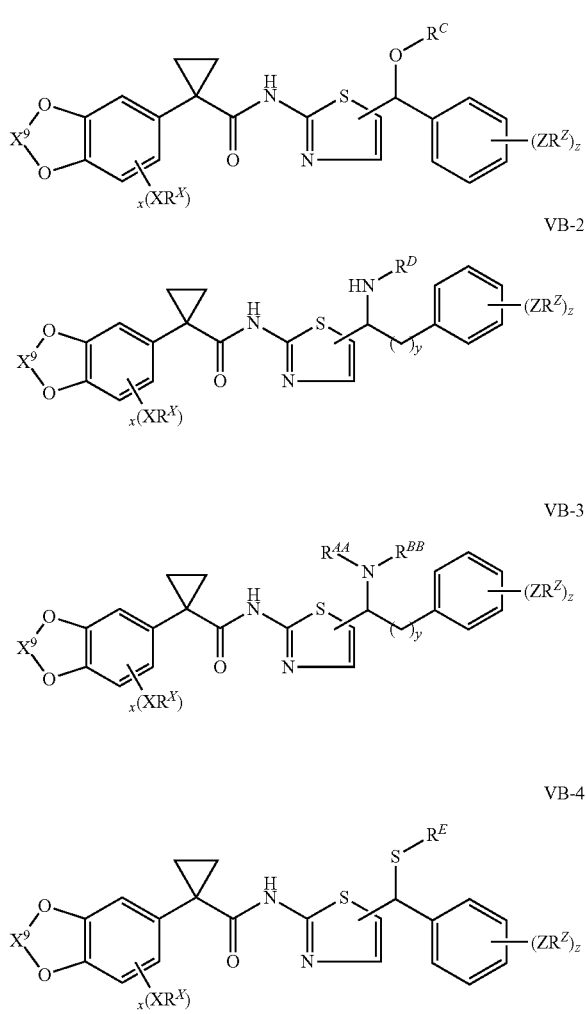

wherein:

$X^9$ is $CH_2$, $CF_2$, $CH_2$—$CH_2$, or $CF_2$—$CF_2$;

each of $R^{AA}$, $R^{BB}$, $R^C$, $R^D$ and $R^E$ is independently hydrogen, C1-C6 aliphatic, C3-C7 cycloalkyl, (C3-C7-cycloalkyl)-C1-C6 aliphatic, (C3-C7-cycloalkenyl)-C1-C6-aliphatic, (3-7-membered heterocycyl), (3-7-membered heterocycyl)-C1-C6-aliphatic, (3-6-membered heteroaryl)-C1-C6 aliphatic, wherein said aliphatic, cycloalkyl, cycloalkenyl, heterocyclyl, or heteroaryl is optionally substituted with up to three substituents selected from OH, —$O(C_{1-4}$aliphatic), —$CF_3$, —$OCF_3$, —$SCF_3$, halo, $NH_2$, NHR, $N(R)_2$, or $(C_1$-$C_4$ aliphatic$)_p$-Y;

p is 0 or 1;

y is 0 or 1;

Y is hydrogen, halo, CN, $NO_2$, $CF_3$, $OCF_3$, OR, SR, $NH_2$, NHR, $N(R)_2$, NRCOR, COOH, or COOR;

R is hydrogen or $C_{1-4}$ aliphatic; or $R^{AA}$ and $R^{BB}$, taken together with the nitrogen atom, is a 3-7 membered heterocyclic ring containing up to 4 heteroatoms selected from O, N, or S, wherein said ring is optionally substituted with up to 2 substituents selected from oxo or (C1-C4 aliphatic)$_p$-Y; and wherein up to two methylene groups in any said aliphatic above are optionally and independently replaced with O, S, C(O), NH, or N(C1-C6 allyl).

In one embodiment, y is 0. In another embodiment, y is 1.

In one embodiment, $X^9$ is $CH_2$. Or, $X^9$ is $CF_2$. Or, $X^9$ is $CH_2$—$CH_2$ or $CF_2$—$CF_2$.

Preferred embodiments of $R^C$ in the present invention include hydrogen, methyl, ethyl, —$(CH_2)_2$-(4-hydroxy-1-piperidyl), —$(CH_2)_3$-(4-hydroxy-1-piperidyl), —$(CH_2)_4$-(4-hydroxy-1-piperidyl), ethylmethylamino-ethyl, 2-hydroxyethyl, 3-hydroxypropyl, 4-hydroxybutyl, 2-methoxyethyl, isopropyl, (2-methoxymethyl-1-pyrrolidinyl)ethyl, tetrahydrofuran-2-ylmethyl, tetrahydrofuran-3-ylmethyl, (pyrrolidin-2-one-5-yl)methyl, (pyrrolidin-1-yl)ethyl, dimethylaminoethyl, 1-piperidylethyl, allyl, n-propyl, diisopropylaminoethyl, and (N-morpholino)ethyl.

In one embodiment, $R^D$ is hydrogen.

In one embodiment, $R^D$ is optionally substituted C1-C6 aliphatic. Exemplary embodiments include C1-C6 alkyl, optionally substituted with up two substituents selected from OH, —O(C1-C4 alkyl), acetamido, $NH_2$, NH(C1-C4 alkyl), or N(C1-C4 alkyl)$_2$.

In another embodiment, $R^D$ is an optionally substituted C3-C6 cycloalkyl or cycloalkenyl ring, or (C3-C6 cycloalkyl or cycloalkenyl ring)-C1-C6 aliphatic. Exemplary embodiments include cyclopropyl, cyclobutyl, cyclopentyl, cyclohexyl, cyclohexenylethyl or cyclohexylmethyl.

In one embodiment, $R^D$ is optionally substituted 3-7 membered heterocyclyl or (3-7 membered heterocyclyl)-C1-C6 aliphatic, wherein said heterocyclyl contains up to 2 heteroatoms selected from O, S, or N. Exemplary embodiments include (N-methyl-pyrrolidin-2-yl)-ethyl, pyrrolidin-1-ylethyl, isoxazolin-3-one-4-yl, 2,2-dimethyl-tetrahydro-2H-pyran-4-yl, tetrahydrofuran-2-yl-methyl, morpholin-4-yl-ethyl, morpholin-4-yl-propyl, or piperidin-1-yl-ethyl.

In another embodiment, $R^D$ is optionally substituted 5-6 membered heteroaryl or (5-6-membered heteroaryl)-C1-C6 aliphatic, wherein said heteroaryl contains up to 2 heteroatoms selected from O, S, or N. Exemplary embodiments include imidazolylpropyl, furanylmethyl, or pyridinylethyl.

In certain embodiments, $R^D$ is $C_{1-4}$ alkyl optionally substituted with —OH, —$O(C_{1-4}$alkyl), NH($C_{1-4}$ alkyl), or N($C_{1-4}$ alkyl)$_2$. In other embodiments, $R^D$ is $C_{1-4}$ alkyl optionally substituted with 5-6 membered heterocyclic ring containing up to 2 heteroatoms selected from O, N, or S, wherein said ring is optionally substituted with up to 2 substituents selected from oxo, ($C_{1-4}$ aliphatic), ($C_{1-4}$ aliphatic)-Y, wherein Y is halo, —OH, or —$O(C_{1-4}$ alkyl).

Preferred embodiments of $R^D$ include (N-morpholino)ethyl, (N-morpholino)propyl, dimethylaminoethyl, or (N-piperidyl)ethyl. Or, $R^D$ is as shown for any of the compounds in Table 1 herein.

In one embodiment, one of $R^{AA}$ and $R^{BB}$ is C1-C4 alkyl, and the other of $R^{AA}$ and $R^{BB}$ is selected from C1-C4 alkyl, C2-C4 alkenyl, C3-C6 cycloalkyl, (C3-C6 cycloalkyl)-C1-C4 alkyl, wherein said alkyl, alkenyl, or cycloalkenyl has up to 2 substituents selected from OH or —O(C1-C4 alkyl).

In one embodiment, $R^{AA}$ and $R^{BB}$, taken together with the nitrogen atom, forms a ring selected from pyrrolidinyl, imidazolyl, piperidinyl, piperazinyl, or morpholinyl, wherein said ring is optionally substituted with up to two substituents selected from hydroxy, C1-C4 alkyl, C2-C4 alkenyl, COOH, acetoxy, acetyl, hydroxymethyl, methoxymethyl, methoxyethyl, allyl, ethylenedioxy, or $C(O)NH_2$.

In one embodiment, the present invention provides compounds of formula VB-3-i:

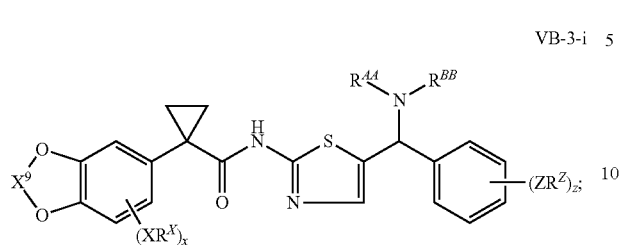

VB-3-i wherein $X^9$ is $CH_2$, $CF_2$, $CH_2$—$CH_2$, or $CF_2$—$CF_2$;

$R^{AA}$ and $R^{BB}$ are selected from hydrogen, C1-C6 alkyl, or —CH(C1-C6 alkyl)-$CH_2$OH; or $R^{AA}$ and $R^{BB}$ taken together form a pyrrolidinyl ring optionally substituted with (C1-C4 aliphatic)$_p$-Y;

Y is halo, CN, $NO_2$, $CF_3$, $OCF_3$, OR, OCOR, SR, $NH_2$, NHR, $N(R)_2$, COOH, or COOR; and R is hydrogen or $C_{1-4}$ aliphatic; and $X^9$, Z, $R^X$, $R^Z$, x, p, and z are as defined above.

In one embodiment, $X^9$ is $CH_2$. Or, $X^9$ is $CF_2$. Or, $X^9$ is $CH_2$—$CH_2$ or $CF_2$—$CF_2$.

In one embodiment, $R^{AA}$ and $R^{BB}$ both are simultaneously hydrogen.

In one embodiment, $R^{AA}$ and $R^{BB}$ taken together is 3-acetoxy-pyrrolidin-1-yl, 2-methoxymethyl-pyrrolidin-1-yl, hydroxymethyl-pyrrolidin-1-yl, pyrrolidin-1-yl, 2-aminocarbonyl-pyrrolidin-1-yl, or 3-hydroxy-pyrrolidin-1-yl.

In one embodiment, $R^{AA}$ is hydrogen, and $R^{BB}$ is —CH(C1-C6 alkyl)-$CH_2$OH. Exemplary such alkyl include methyl, ethyl, n-propyl, isopropyl, n-butyl, t-butyl, or isobutyl. In one embodiment, $R^{BB}$ is (R)—CH(C1-C6 alkyl)-$CH_2$OH. Or, $R^{BB}$ is (S)—CH(C1-C6 alkyl)-$CH_2$OH.

In another embodiment, the present invention provides compounds of formula VB-3-ii:

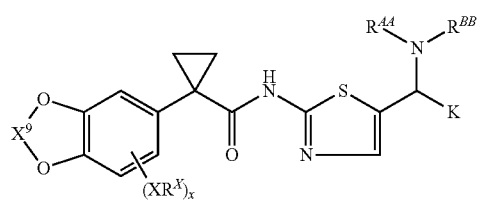

wherein:

K is C1-C6 aliphatic;

$X^9$ is $CH_2$, $CF_2$, $CH_2$—$CH_2$, or $CF_2$—$CF_2$;

$R^{AA}$ and $R^{BB}$ are selected from C1-C6 alkyl; or $R^{AA}$ and $R^{BB}$ taken together form a pyrrolidinyl, piperidinyl, or morpholinyl ring optionally substituted with (C1-C4 aliphatic)$_p$-Y;

Y is halo, CN, $NO_2$, $CF_3$, $OCF_3$, OR, SR, $NH_2$, NHR, $N(R)_2$, COOH, $CONH_2$, or COOR; and R is hydrogen or $C_{1-4}$ aliphatic; and $X^9$, Z, $R^X$, $R^Z$, x, p, and z are as defined above.

According to another embodiment, the present invention provides compounds of formula VIA or formula VIB:

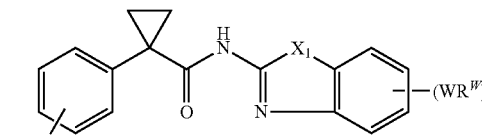

VIA

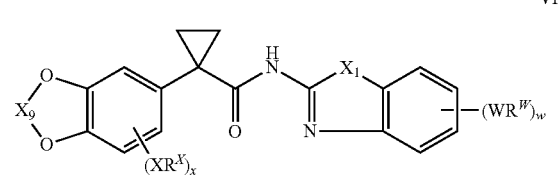

VIB wherein:

$X^1$ is O, S, or NR; and

R is hydrogen or $C_{1-4}$ alkyl.

According to one embodiment of formula VIA, $X^1$ is S. Or, $X^1$ is O. Or, $X^1$ is NR. In one embodiment, R is hydrogen. Or, R is $C_{1-4}$ alkyl.

According to one embodiment of formula VIB, $X^1$ is S. Or, $X^1$ is O. Or, $X^1$ is NR. In one embodiment, R is hydrogen. Or, R is $C_{1-4}$ alkyl.

According to another embodiment, the present invention provides compounds of formula VIIA or formula VIIB:

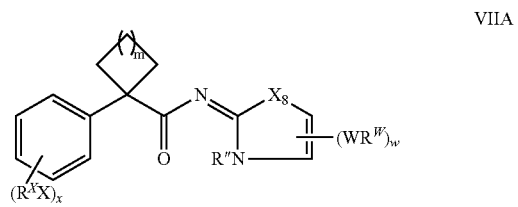

VIIA

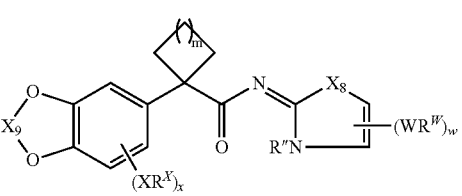

VIIB wherein:

m is 0-4;

$X^8$ is O or S; and

R" is $C_{1-4}$ alkyl optionally substituted with NH($C_{1-4}$ alkyl), N($C_{1-4}$ alkyl)$_2$, or C(O)O—($C_{1-4}$ alkyl)

In certain embodiments of formula VIIA or formula VIIB, m is 0. Or, m is 2 or 3.

In certain embodiments of formula VIIA or formula VIIB, R" is methyl.

In certain embodiments of formula VIIA or formula VIIB, $X^8$ is S. Or, $X^8$ is O.

In an alternative embodiment, the present invention provides compounds of formula I' useful as modulators of CFTR:

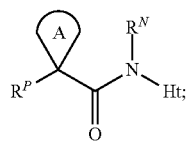

wherein $R^N$, Ht and ring A are as defined above; and
$R^P$ is hydrogen, CN, C1-C6 aliphatic optionally substituted with $NH_2$ or phenyl, wherein said phenyl is optionally substituted with up to 3 substituents selected from OR;
wherein up to two methylene groups in said aliphatic is optionally and independently replaced by O, S, NH, or C(O);
R is C1-C4 alkyl.

Exemplary compounds of the present invention are recited below in Table 1.

TABLE 1-continued
| Cmpd # | Compound |
|---|---|
| 9 | 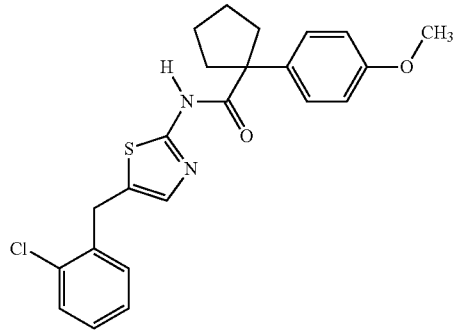 [SMILES: COc1ccc(C2(C(=O)Nc3ncc(Cc4ccccc4Cl)s3)CCCC2)cc1] |
| 10 | 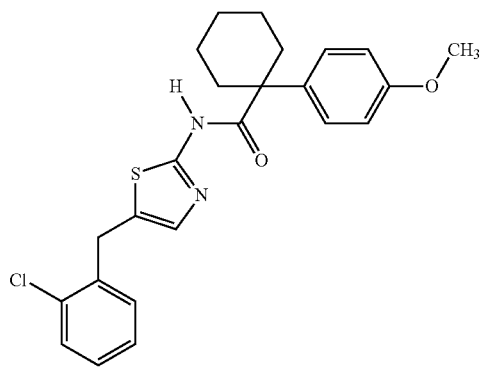 [SMILES: COc1ccc(C2(C(=O)Nc3ncc(Cc4ccccc4Cl)s3)CCCCC2)cc1] |
| 11 | 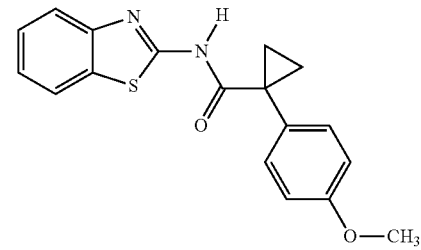 [SMILES: COc1ccc(C2(C(=O)Nc3nc4ccccc4s3)CC2)cc1] |
| 12 | 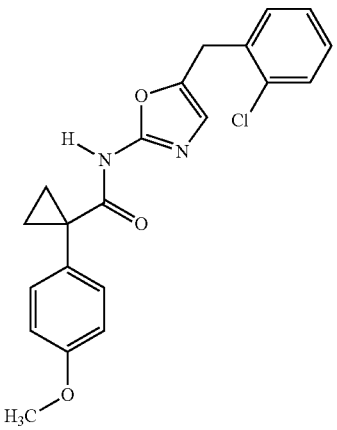 [SMILES: COc1ccc(C2(C(=O)Nc3ncc(Cc4ccccc4Cl)o3)CC2)cc1] |
TABLE 1-continued
| Cmpd # | Compound |
|---|---|
| 13 | 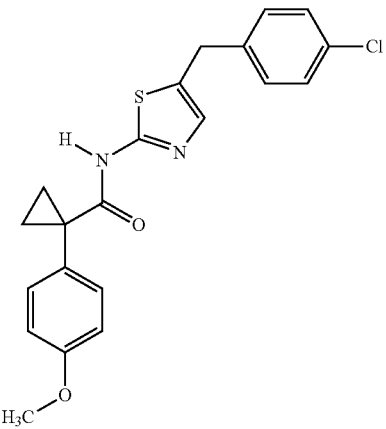 [SMILES: COc1ccc(C2(C(=O)Nc3ncc(Cc4ccc(Cl)cc4)s3)CC2)cc1] |
| 14 | 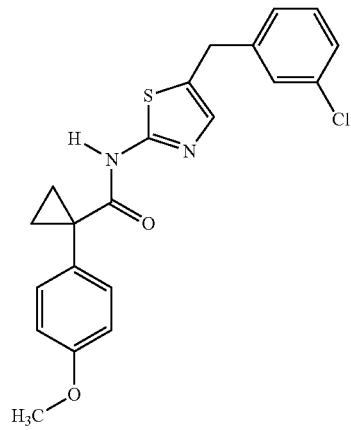 [SMILES: COc1ccc(C2(C(=O)Nc3ncc(Cc4cccc(Cl)c4)s3)CC2)cc1] |
| 15 | 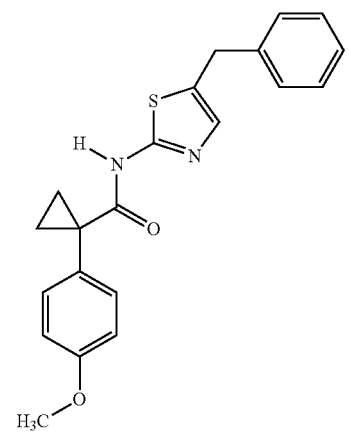 [SMILES: COc1ccc(C2(C(=O)Nc3ncc(Cc4ccccc4)s3)CC2)cc1] |

TABLE 1-continued

| Cmpd # | Compound |
|---|---|
| 16 | N-[5-(2-methoxybenzyl)thiazol-2-yl]-1-(4-methoxyphenyl)cyclopropanecarboxamide |
| 17 | 1-(4-methoxyphenyl)-N-(4-phenylthiazol-2-yl)cyclopropanecarboxamide |
| 18 | 1-(4-methoxyphenyl)-N-(5-phenylthiazol-2-yl)cyclopropanecarboxamide |
| 19 | N-[4-(2-chlorophenyl)thiazol-2-yl]-1-(4-methoxyphenyl)cyclopropanecarboxamide |
| 20 | N-[5-(2-methoxybenzyl)thiazol-2-yl]-1-(4-methoxyphenyl)cyclohexanecarboxamide |
| 21 | 1-(4-chlorophenyl)-N-[5-(2-methoxybenzyl)thiazol-2-yl]cyclopentanecarboxamide |
| 22 | 1-(4-chlorophenyl)-N-[5-(2-chlorobenzyl)thiazol-2-yl]cyclopentanecarboxamide |

TABLE 1-continued

| Cmpd # | Compound |
|---|---|
| 23 | 1-(3-fluorophenyl)-N-[5-(2-methoxybenzyl)thiazol-2-yl]cyclopentanecarboxamide |
| 24 | 1-(3-fluorophenyl)-N-[5-(2-chlorobenzyl)thiazol-2-yl]cyclopentanecarboxamide |
| 25 | 1-(4-fluorophenyl)-N-[5-(2-methoxybenzyl)thiazol-2-yl]cyclopentanecarboxamide |
| 26 | 1-(4-fluorophenyl)-N-[5-(2-chlorobenzyl)thiazol-2-yl]cyclopentanecarboxamide |
| 27 | N-[5-(2-methoxybenzyl)thiazol-2-yl]-1-(4-methoxyphenyl)cyclopentanecarboxamide |
| 28 | 1-(2-fluorophenyl)-N-[5-(2-methoxybenzyl)thiazol-2-yl]cyclopentanecarboxamide |
| 29 | 1-(2-fluorophenyl)-N-[5-(2-chlorobenzyl)thiazol-2-yl]cyclopentanecarboxamide |
| 30 | N-[5-(2-methoxybenzyl)thiazol-2-yl]-1-phenylcyclohexanecarboxamide |

TABLE 1-continued

| Cmpd # | Compound |
|---|---|
| 31 | (structure) |
| 32 | (structure) |
| 33 | (structure) |
| 34 | (structure) |
| 35 | (structure) |
| 36 | (structure) |
| 37 | (structure) |
| 38 | (structure) |

TABLE 1-continued
| Cmpd # | Compound |
|---|---|
| 39 | 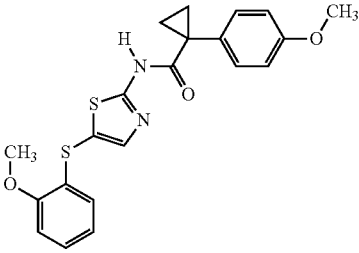 [SMILES: COc1ccc(C2(C(=O)Nc3ncc(Sc4ccccc4OC)s3)CC2)cc1] |
| 40 | 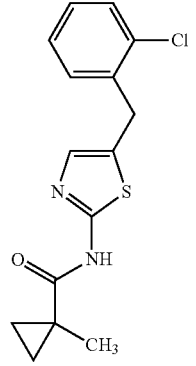 [SMILES: CC1(C(=O)Nc2ncc(Cc3ccccc3Cl)s2)CC1] |
| 41 | 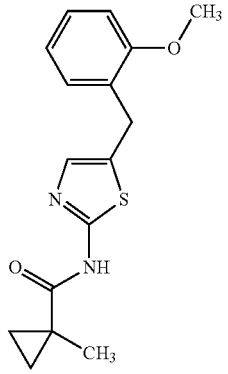 [SMILES: COc1ccccc1Cc1cnc(NC(=O)C2(C)CC2)s1] |
| 42 | 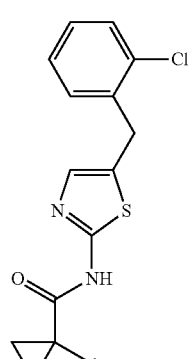 |
| 43 | 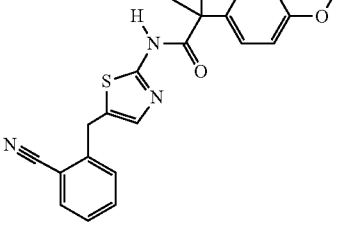 |
| 44 | 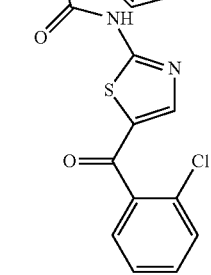 |
| 45 | 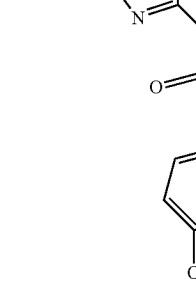 |
| 46 | 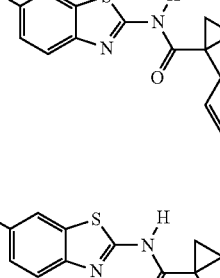 |
| 47 | 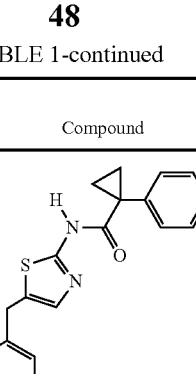 |

TABLE 1-continued

| Cmpd # | Compound |
|---|---|
| 48 | 4-chlorobenzothiazol-2-yl cyclopropanecarboxamide with 4-methoxyphenyl |
| 49 | 6-methoxybenzothiazol-2-yl cyclopropanecarboxamide with 4-methoxyphenyl |
| 50 | 4-methylbenzothiazol-2-yl cyclopropanecarboxamide with 4-methoxyphenyl |
| 51 | 1-(4-methoxyphenyl)-N-(5-(2-chlorophenylsulfinyl)thiazol-2-yl)cyclopropanecarboxamide |
| 52 | 1-(4-methoxyphenyl)-N-(5-(2-chlorophenylsulfonyl)thiazol-2-yl)cyclopropanecarboxamide |
| 53 | 1-(4-methoxyphenyl)-N-(5-(2-chlorophenoxy)thiazol-2-yl)cyclopropanecarboxamide |
| 54 | N-(5-(2-chlorobenzyl)thiazol-2-yl)-4-(4-methoxyphenyl)tetrahydro-2H-pyran-4-carboxamide |
| 55 | N-(5-(2-chlorobenzyl)thiazol-2-yl)-1-(3,4-dimethoxyphenyl)cyclopropanecarboxamide |
| 56 | N-(5-(2-chlorobenzyl)thiazol-2-yl)-1-(benzo[d][1,3]dioxol-5-yl)cyclopropanecarboxamide |
| 57 | N-(5-(2-methoxybenzyl)thiazol-2-yl)-4-(4-methoxyphenyl)tetrahydro-2H-pyran-4-carboxamide |

TABLE 1-continued

| Cmpd # | Compound |
|---|---|
| 58 | (structure) |
| 59 | (structure) |
| 60 | (structure) |
| 61 | (structure) |
| 62 | (structure) |
| 63 | (structure) |
| 64 | (structure) |
| 65 | (structure) |
| 66 | (structure) |
| 67 | (structure) |
| 68 | (structure) |
| 69 | (structure) |

TABLE 1-continued

| Cmpd # | Compound |
|---|---|
| 70 | |
| 71 | |
| 72 | |
| 73 | |
| 74 | |
| 75 | |
| 76 | |
| 77 | |
| 78 | |
| 79 | |

TABLE 1-continued

| Cmpd # | Compound |
|---|---|
| 80 | |
| 81 | |
| 82 | |
| 83 | |
| 84 | |
| 85 | |
| 86 | |
| 87 | |
| 88 | |
| 89 | |
| 90 | |
| 91 | |

TABLE 1-continued

| Cmpd # | Compound |
|---|---|
| 92 | |
| 93 | |
| 94 | |
| 95 | |
| 96 | |
| 97 | |
| 98 | |
| 99 | |
| 100 | |
| 101 | |

TABLE 1-continued

| Cmpd # | Compound |
|---|---|
| 102 | |
| 103 | |
| 104 | |
| 105 | |
| 106 | |
| 107 | |
| 108 | |
| 109 | |
| 110 | |
| 111 | |
| 112 | |
| 113 | |
| 114 | |

TABLE 1-continued

| Cmpd # | Compound |
|---|---|
| 115 | |
| 116 | |
| 117 | |
| 118 | |
| 119 | |
| 120 | |
| 121 | |
| 122 | |
| 123 | |
| 124 | |

TABLE 1-continued

| Cmpd # | Compound |
|---|---|
| 125 | |
| 126 | |
| 127 | |
| 128 | |
| 129 | |
| 130 | |
| 131 | |
| 132 | |
| 133 | |
| 134 | |

TABLE 1-continued

| Cmpd # | Compound |
|---|---|
| 135 | |
| 136 | |
| 137 | |
| 138 | |
| 139 | |
| 140 | |
| 141 | |
| 142 | |
| 143 | |
| 144 | |

TABLE 1-continued

| Cmpd # | Compound |
|---|---|
| 145 | |
| 146 | |
| 147 | |
| 148 | |
| 149 | |
| 150 | |
| 151 | |
| 152 | |
| 153 | |
| 154 | |
| 155 | |

TABLE 1-continued
| Cmpd # | Compound |
|---|---|
| 156 | 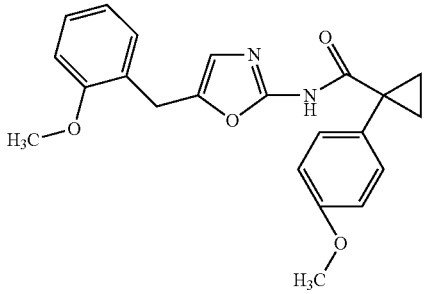 [SMILES: COc1ccc(C2(C(=O)Nc3ncc(Cc4ccccc4OC)o3)CC2)cc1] |
| 157 | 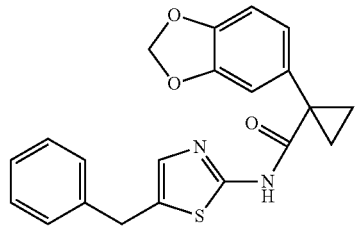 |
| 158 | 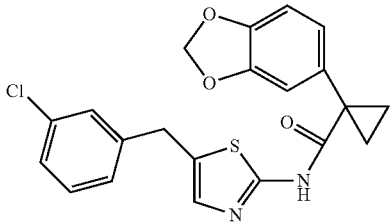 [SMILES: O=C(Nc1ncc(Cc2cccc(Cl)c2)s1)C1(c2ccc3c(c2)OCO3)CC1] |
| 159 | 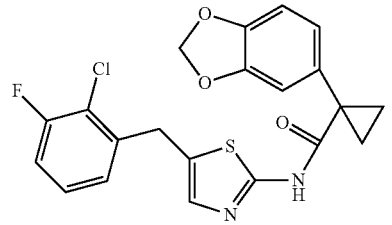 [SMILES: O=C(Nc1ncc(Cc2cccc(F)c2Cl)s1)C1(c2ccc3c(c2)OCO3)CC1] |
| 160 | 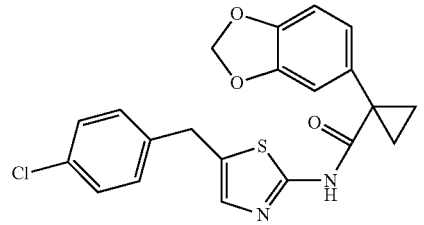 |
| 161 | 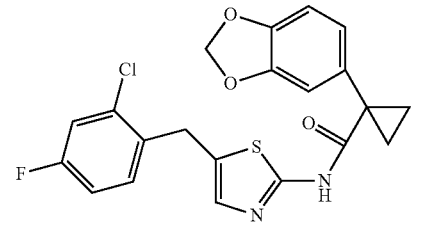 [SMILES: O=C(Nc1ncc(Cc2ccc(F)cc2Cl)s1)C1(c2ccc3c(c2)OCO3)CC1] |
| 162 | 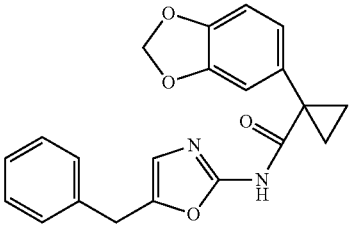 [SMILES: O=C(Nc1ncc(Cc2ccccc2)o1)C1(c2ccc3c(c2)OCO3)CC1] |
| 163 | 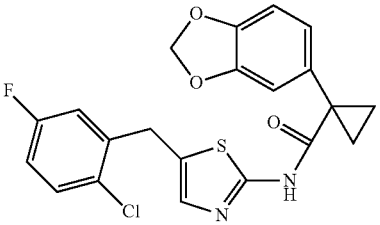 [SMILES: O=C(Nc1ncc(Cc2cc(F)ccc2Cl)s1)C1(c2ccc3c(c2)OCO3)CC1] |
| 164 | 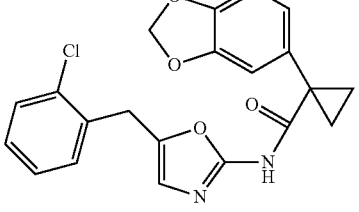 |
| 165 | 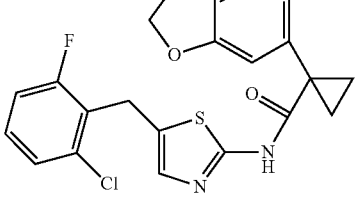 |
| 166 | 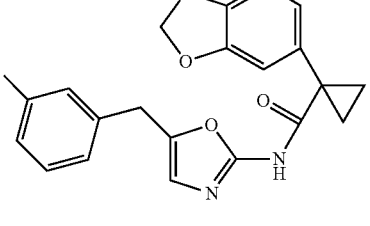 |
| 167 | 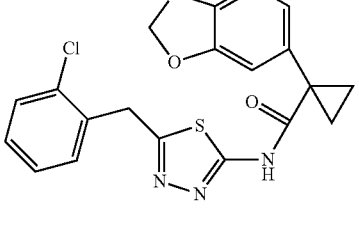 |

TABLE 1-continued

| Cmpd # | Compound |
|---|---|
| 168 | |
| 169 | |
| 170 | |
| 171 | |
| 172 | |
| 173 | |
| 174 | |
| 175 | |
| 176 | |
| 177 | |
| 178 | |
| 179 | |

TABLE 1-continued

| Cmpd # | Compound |
|---|---|
| 180 | |
| 181 | |
| 182 | |
| 183 | |
| 184 | |
| 185 | |
| 186 | |
| 187 | |
| 188 | |
| 189 | |

TABLE 1-continued

| Cmpd # | Compound |
|---|---|
| 190 | |
| 191 | |
| 192 | |
| 193 | |
| 194 | |
| 195 | |
| 196 | |
| 197 | |
| 198 | |
| 199 | |

TABLE 1-continued

| Cmpd # | Compound |
|---|---|
| 200 | |
| 201 | |
| 202 | |
| 203 | |
| 204 | |
| 205 | |
| 206 | |
| 207 | |

TABLE 1-continued
| Cmpd # | Compound |
|---|---|
| 208 | 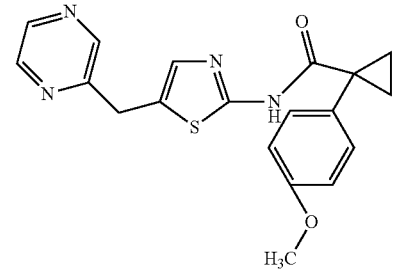 [SMILES: COc1ccc(C2(C(=O)Nc3ncc(Cc4cnccn4)s3)CC2)cc1] |
| 209 | 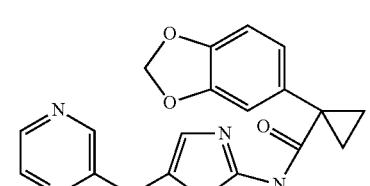 |
| 210 | 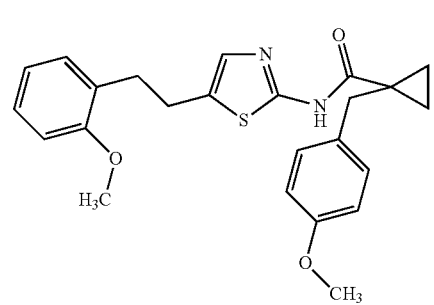 [SMILES: COc1ccc(CC2(C(=O)Nc3ncc(CCc4ccccc4OC)s3)CC2)cc1] |
| 211 | 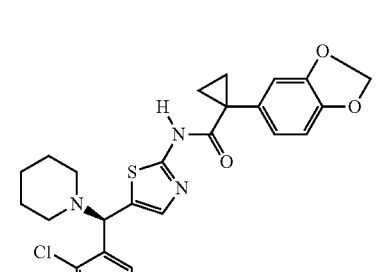 |
| 212 | 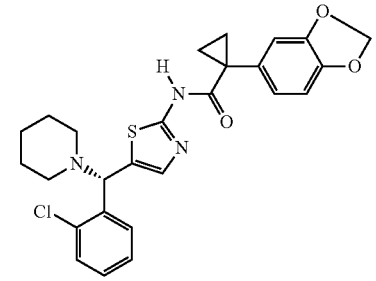 |
| 213 | 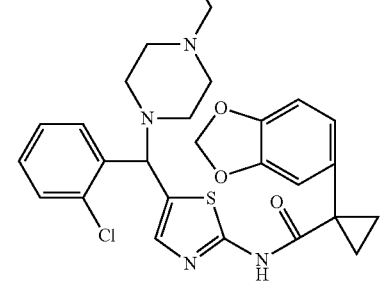 |
| 214 | 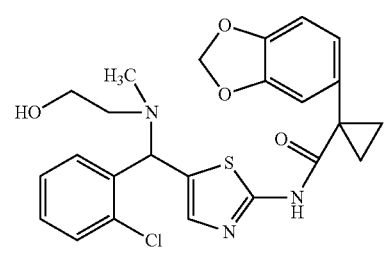 [SMILES: CN(CCO)C(c1cnc(NC(=O)C2(c3ccc4c(c3)OCO4)CC2)s1)c1ccccc1Cl] |
| 215 | 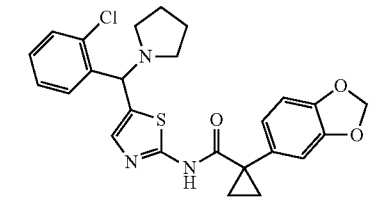 [SMILES: O=C(Nc1ncc(C(c2ccccc2Cl)N2CCCC2)s1)C1(c2ccc3c(c2)OCO3)CC1] |
| 216 | 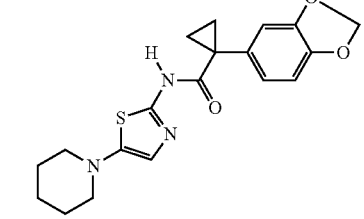 |
| 217 | 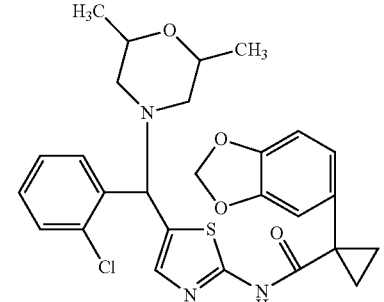 |

TABLE 1-continued
| Cmpd # | Compound |
|---|---|
| 218 |  |
| 219 | |
| 220 | |
| 221 | |
| 222 | |
| 223 | |
| 224 |  |
| 225 | |
| 226 | |
| 227 | |
| 228 | |

TABLE 1-continued

| Cmpd # | Compound |
|---|---|
| 229 | (structure) |
| 230 | (structure) |
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |

TABLE 1-continued
| Cmpd # | Compound |
|---|---|
| 241 | 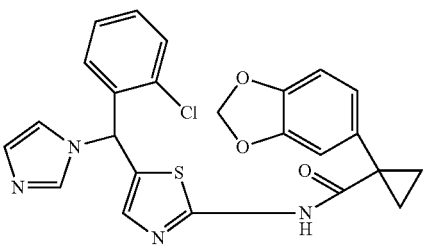 [SMILES: O=C(Nc1ncc(C(c2ccccc2Cl)n2ccnc2)s1)C1(c2ccc3c(c2)OCO3)CC1] |
| 242 | 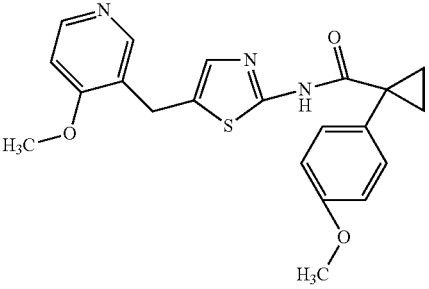 [SMILES: COc1ccc(C2(C(=O)Nc3ncc(Cc4cnccc4OC)s3)CC2)cc1] |
| 243 | 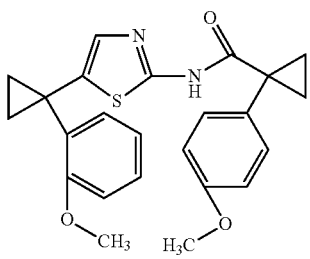 [SMILES: COc1ccc(C2(C(=O)Nc3ncc(C4(c5ccccc5OC)CC4)s3)CC2)cc1] |
| 244 | 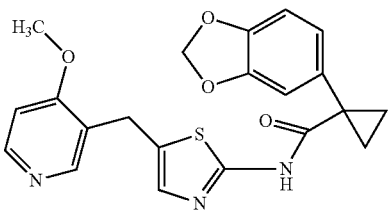 [SMILES: COc1ccncc1Cc1cnc(NC(=O)C2(c3ccc4c(c3)OCO4)CC2)s1] |
| 245 | 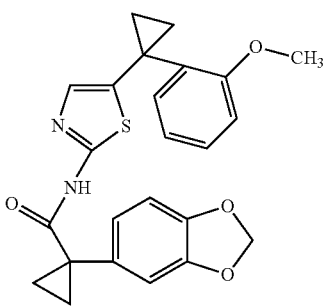 [SMILES: COc1ccccc1C1(c2cnc(NC(=O)C3(c4ccc5c(c4)OCO5)CC3)s2)CC1] |
| 246 | 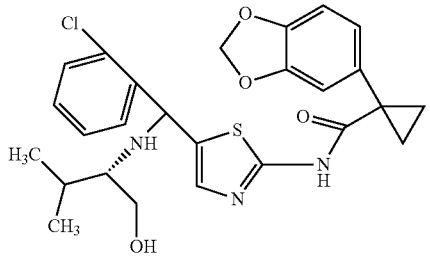 [SMILES: CC(C)[C@@H](CO)NC(c1cnc(NC(=O)C2(c3ccc4c(c3)OCO4)CC2)s1)c1ccccc1Cl] |
| 247 | 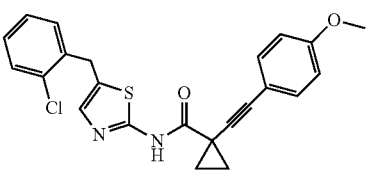 [SMILES: COc1ccc(C#CC2(C(=O)Nc3ncc(Cc4ccccc4Cl)s3)CC2)cc1] |
| 248 | 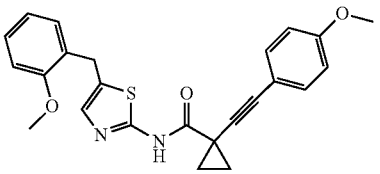 [SMILES: COc1ccc(C#CC2(C(=O)Nc3ncc(Cc4ccccc4OC)s3)CC2)cc1] |
| 249 | 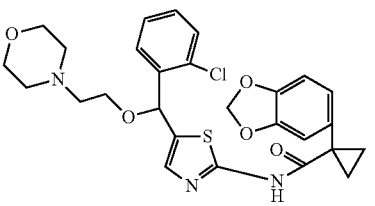 [SMILES: O=C(Nc1ncc(C(OCCN2CCOCC2)c2ccccc2Cl)s1)C1(c2ccc3c(c2)OCO3)CC1] |
| 250 | 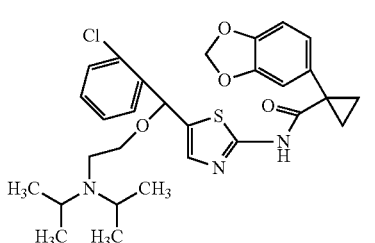 |
| 251 | 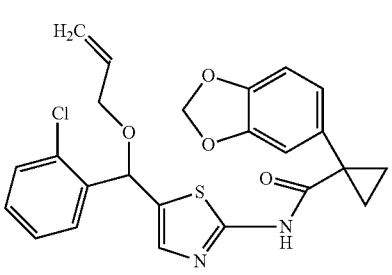 [SMILES: C=CCOC(c1cnc(NC(=O)C2(c3ccc4c(c3)OCO4)CC2)s1)c1ccccc1Cl] |
| 252 | 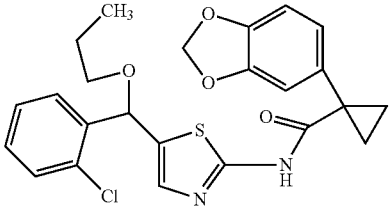 [SMILES: CCCOC(c1cnc(NC(=O)C2(c3ccc4c(c3)OCO4)CC2)s1)c1ccccc1Cl] |

TABLE 1-continued

| Cmpd # | Compound |
|---|---|
| 253 | |
| 254 | |
| 255 | |
| 256 | |
| 257 | |
| 258 | |
| 259 | |
| 260 | |
| 261 | |
| 262 | |
| 263 | |
| 264 | |

TABLE 1-continued

| Cmpd # | Compound |
|---|---|
| 265 | (structure) |
| 266 | (structure) |
| 267 | (structure) |
| 268 | (structure) |
| 269 | (structure) |
| 270 | (structure) |
| 271 | (structure) |
| 272 | (structure) |
| 273 | (structure) |
| 274 | (structure) |
| 275 | (structure) |
| 276 | (structure) |

TABLE 1-continued

| Cmpd # | Compound |
|---|---|
| 277 | (structure) |
| 278 | (structure) |
| 279 | (structure) |
| 280 | (structure) |
| 281 | (structure) |
| 282 | (structure) |
| 283 | (structure) |
| 284 | (structure) |
| 284 | (structure) |
| 285 | (structure) |
| 286 | (structure) |

TABLE 1-continued

| Cmpd # | Compound |
|---|---|
| 287 | |
| 288 | |
| 289 | |
| 290 | |
| 291 | |
| 292 | |
| 293 | |
| 294 | |
| 295 | |
| 296 | |
| 297 | |

TABLE 1-continued

| Cmpd # | Compound |
|---|---|
| 298 | |
| 299 | |
| 300 | |
| 301 | |
| 302 | |
| 303 | |
| 304 | |
| 305 | |
| 306 | |

TABLE 1-continued
| Cmpd # | Compound |
|---|---|
| 307 | 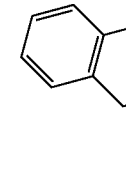 |
| 308 |  |
| 309 | 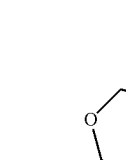 |
| 310 | 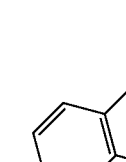 |
| 311 | 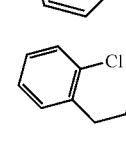 |
| 312 |  |
| 313 | |
| 314 | |
| 315 | |
| 316 |  |

TABLE 1-continued

| Cmpd # | Compound |
|---|---|
| 317 | |
| 318 | |
| 319 | |
| 320 | |
| 321 | |
| 322 | |
| 323 | |
| 324 | |
| 325 | |
| 326 | |
| 327 | |

TABLE 1-continued
| Cmpd # | Compound |
|---|---|
| 328 | 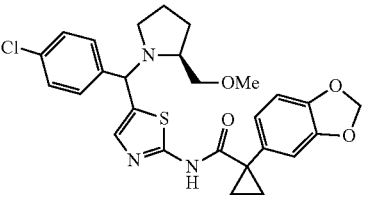 [SMILES: COC[C@@H]1CCCN1C(c1ccc(Cl)cc1)c1cnc(NC(=O)C2(c3ccc4c(c3)OCO4)CC2)s1] |
| 329 | 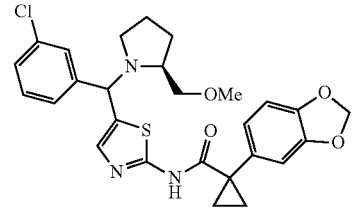 [SMILES: COC[C@@H]1CCCN1C(c1cccc(Cl)c1)c1cnc(NC(=O)C2(c3ccc4c(c3)OCO4)CC2)s1] |
| 330 | 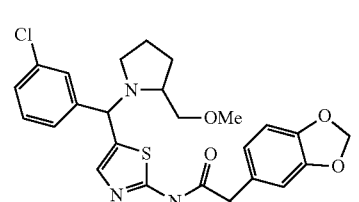 |
| 331 | 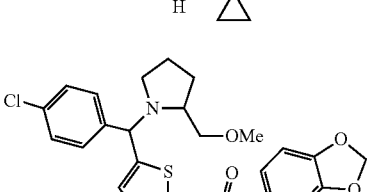 |
| 332 | 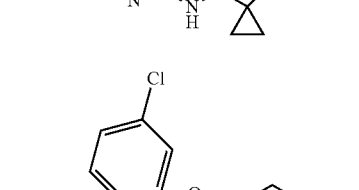 |
| 333 | 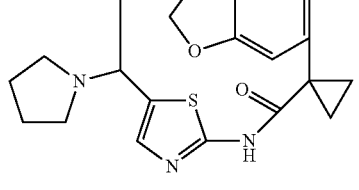 |
| 334 | 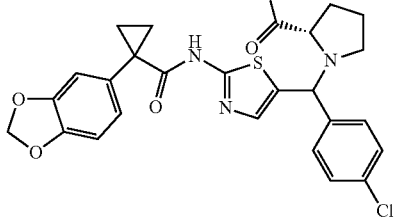 |
| 335 | 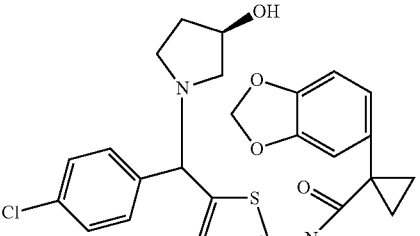 |
| 336 | 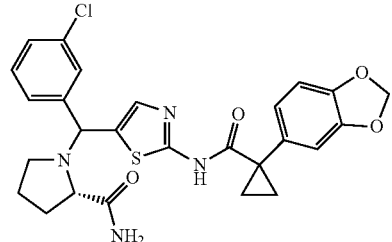 |
| 337 | 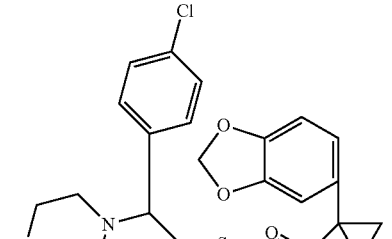 |
| 338 | 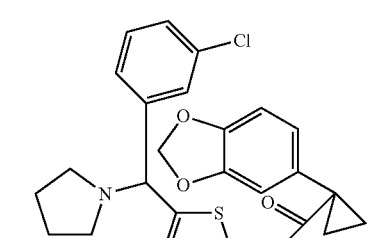 |

TABLE 1-continued

| Cmpd # | Compound |
|---|---|
| 339 | |
| 340 | |
| 341 | |
| 342 | |
| 343 | |
| 344 | |
| 345 | |
| 346 | |
| 347 | |
| 348 | |
| 349 | |

TABLE 1-continued

| Cmpd # | Compound |
|---|---|
| 350 | |
| 351 | |
| 352 | |
| 353 | |
| 354 | |
| 355 | |
| 356 | |
| 357 | |
| 358 | |
| 359 | |
| 360 | |

US 8,541,453 B2
TABLE 1-continued
| Cmpd # | Compound |
|---|---|
| 361 | 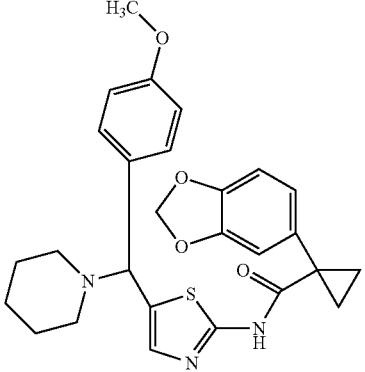 [SMILES: COc1ccc(C(c2cnc(NC(=O)C3(c4ccc5c(c4)OCO5)CC3)s2)N2CCCCC2)cc1] |
| 362 | 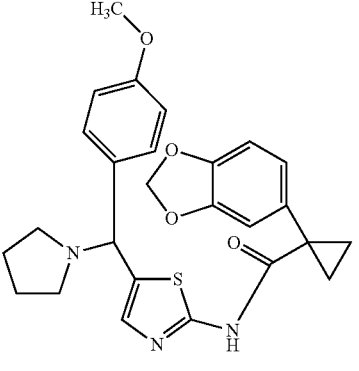 [SMILES: COc1ccc(C(c2cnc(NC(=O)C3(c4ccc5c(c4)OCO5)CC3)s2)N2CCCC2)cc1] |
| 363 | 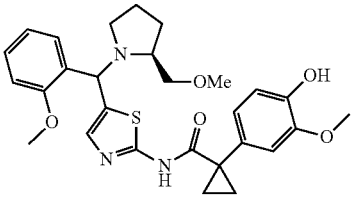 [SMILES: COC[C@@H]1CCCN1C(c1cnc(NC(=O)C2(c3ccc(O)c(OC)c3)CC2)s1)c1ccccc1OC] |
| 364 | 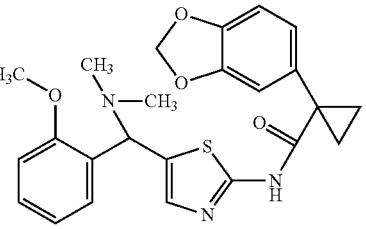 |
| 365 | 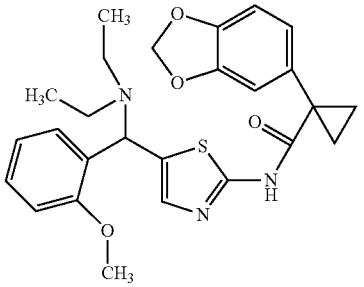 [SMILES: CCN(CC)C(c1cnc(NC(=O)C2(c3ccc4c(c3)OCO4)CC2)s1)c1ccccc1OC] |
TABLE 1-continued
| Cmpd # | Compound |
|---|---|
| 366 | 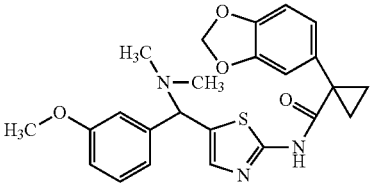 [SMILES: COc1cccc(C(c2cnc(NC(=O)C3(c4ccc5c(c4)OCO5)CC3)s2)N(C)C)c1] |
| 367 | 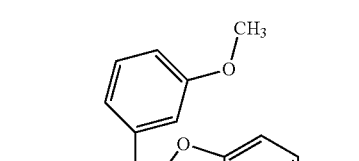 |
| 368 |  |
| 369 | 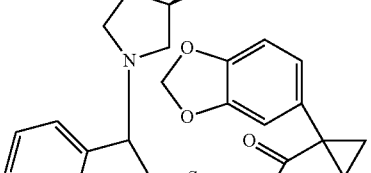 |
| 370 | 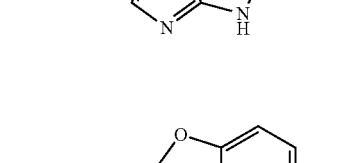 |

TABLE 1-continued

| Cmpd # | Compound |
|---|---|
| 371 | |
| 372 | |
| 373 | |
| 374 | |
| 375 | |
| 376 | |
| 377 | |
| 378 | |
| 379 | |
| 380 | |
| 381 | |

TABLE 1-continued

| Cmpd # | Compound |
|---|---|
| 382 | |
| 383 | |
| 384 | |
| 385 | |
| 386 | |
| 387 | |
| 388 | |
| 389 | |
| 390 | |
| 391 | |
| 392 | |

TABLE 1-continued

| Cmpd # | Compound |
|---|---|
| 393 | |
| 394 | |
| 395 | |
| 396 | |
| 397 | |
| 398 | |
| 399 | |
| 400 | |
| 401 | |
| 402 | |
| 403 | |

TABLE 1-continued

| Cmpd # | Compound |
|---|---|
| 404 | |
| 405 | |
| 406 | |
| 407 | |
| 408 | |
| 409 | |
| 410 | |
| 411 | |
| 412 | |
| 413 | |

TABLE 1-continued

| Cmpd # | Compound |
|---|---|
| 414 | |
| 415 | |
| 416 | |
| 417 | |
| 418 | |
| 419 | |
| 420 | |
| 421 | |
| 422 | |
| 423 | |
| 424 | |
| 425 | |

TABLE 1-continued
| Cmpd # | Compound |
|---|---|
| 426 | 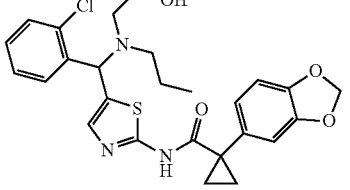 |
| 427 | 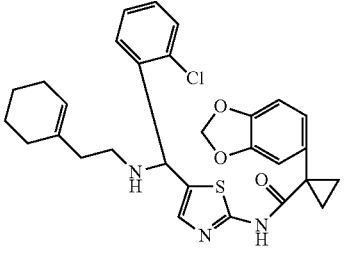 [SMILES: O=C(Nc1ncc(C(NCCC2=CCCCC2)c2ccccc2Cl)s1)C1(c2ccc3c(c2)OCO3)CC1] |
| 428 | 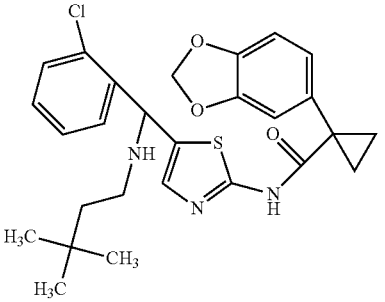 [SMILES: CC(C)(C)CCNC(c1cnc(NC(=O)C2(c3ccc4c(c3)OCO4)CC2)s1)c1ccccc1Cl] |
| 429 | 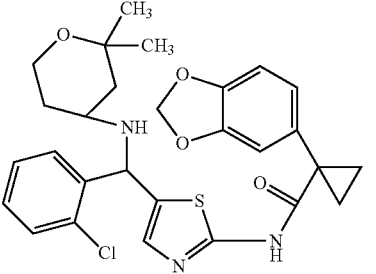 [SMILES: CC1(C)CC(NC(c2cnc(NC(=O)C3(c4ccc5c(c4)OCO5)CC3)s2)c2ccccc2Cl)CCO1] |
| 430 | 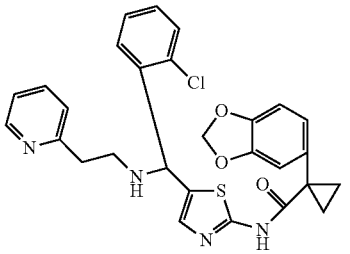 [SMILES: O=C(Nc1ncc(C(NCCc2ccccn2)c2ccccc2Cl)s1)C1(c2ccc3c(c2)OCO3)CC1] |
| 431 | 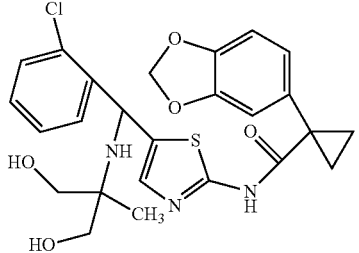 [SMILES: CC(CO)(CO)NC(c1cnc(NC(=O)C2(c3ccc4c(c3)OCO4)CC2)s1)c1ccccc1Cl] |
| 432 | 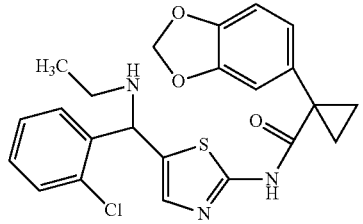 [SMILES: CCNC(c1cnc(NC(=O)C2(c3ccc4c(c3)OCO4)CC2)s1)c1ccccc1Cl] |
| 433 | 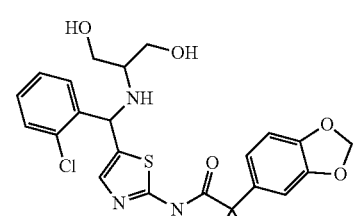 |
| 434 | 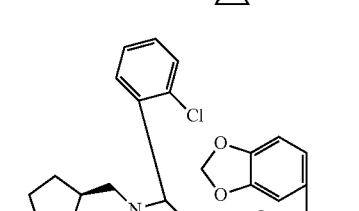 |
| 435 | 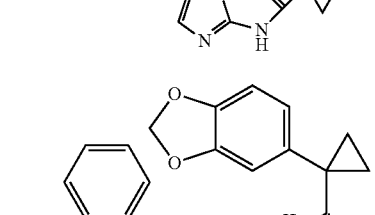 |
| 436 | 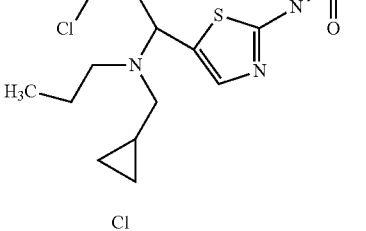 |
| 437 | 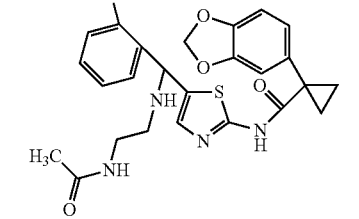 |

TABLE 1-continued

| Cmpd # | Compound |
|---|---|
| 438 | |
| 439 | |
| 440 | |
| 441 | |
| 442 | |
| 443 | |
| 444 | |
| 445 | |
| 446 | |
| 447 | |
| 448 | |

TABLE 1-continued

| Cmpd # | Compound |
|---|---|
| 449 | (structure) |
| 450 | (structure) |
| 451 | (structure) |
| 452 | (structure) |
| 453 | (structure) |
| 454 | (structure) |
| 455 | (structure) |
| 456 | (structure) |
| 457 | (structure) |
| 458 | (structure) |
| 459 | (structure) |
| 460 | (structure) |

TABLE 1-continued

| Cmpd # | Compound |
|---|---|
| 461 | |
| 462 | |
| 463 | |
| 464 | |
| 465 | |
| 466 | |
| 467 | |
| 468 | |
| 469 | |
| 470 | |
| 471 | |

TABLE 1-continued
| Cmpd # | Compound |
|---|---|
| 472 | 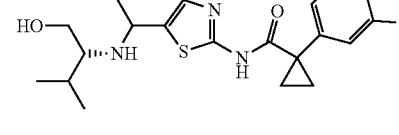 |
| 473 | |
| 474 | |
| 475 | |
| 476 | |
| 477 | |
| 478 | 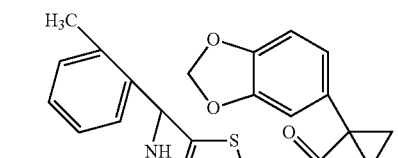 |
| 479 | |
| 480 | |
| 481 | |
| 482 | |

TABLE 1-continued

| Cmpd # | Compound |
|---|---|
| 483 | |
| 484 | |
| 485 | |
| 486 | |
| 487 | |
| 488 | |
| 489 | |
| 490 | |
| 491 | |
| 492 | |
| 493 | |

TABLE 1-continued

| Cmpd # | Compound |
|---|---|
| 494 | |
| 495 | |
| 496 | |
| 497 | |
| 498 | |

4. General Synthetic Schemes

Compounds of formula I can be prepared by well known methods in the art. Illustrated below are exemplary methods for the preparation of compounds of formula I. Scheme I below illustrates an exemplary synthetic method for compounds of formula I.

Scheme I

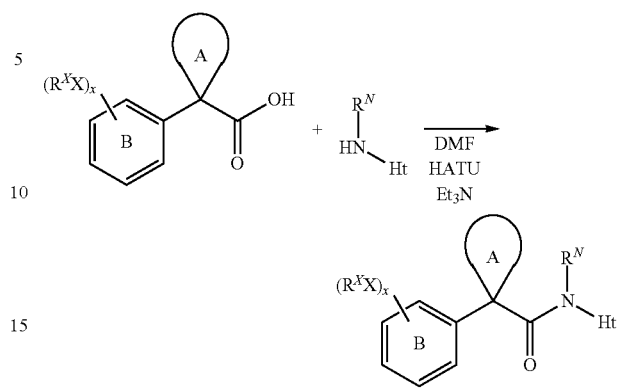

General Procedure: One equivalent of the appropriate carboxylic acid and one equivalent of the appropriate amine were dissolved in N,N-dimethylformamide (DMF) containing triethylamine (3 equivalents). O-(7-Azabenzotriazol-1-yl)-N,N,N',N'-tetramethyluronium hexafluorophosphate (HATU) was added and the solution was allowed to stir. The crude product was purified by reverse-phase preparative liquid chromatography to yield the pure product.

5. Uses, Formulation and Administration

Pharmaceutically Acceptable Compositions

As discussed above, the present invention provides compounds that are useful as modulators of ABC transporters and thus are useful in the treatment of disease, disorders or conditions such as Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of an ATP-Binding Cassette Transporters.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal a-galactosidase A), Straussler-Scheinker syndrome, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of cystic fibrosis, hereditary emphysema (due to a1-antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses (due to lysosomal processing enzymes), Sandhof/Tay-Sachs (due to β-hexosaminidase), Crigler-Najjar type II (due to UDP-glucuronyl-sialyc-transferase), polyendocrinopathy/hyperinsulemia, diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are glycanosis CDG type 1, hereditary emphysema (due to α1-antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

General Schemes

Preparation of Spirocycloalkyl Acids

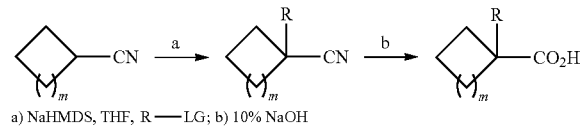

a) NaHMDS, THF, R—LG; b) 10% NaOH

LG = Living Group such as Cl, Br, etc.

Preparation of spirocycloalkyl acids

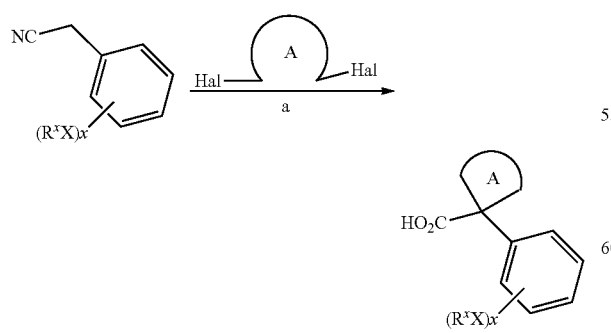

Hal = Cl, Br, I a) NaOH

Preparation of Spirocycloalkyl Acids

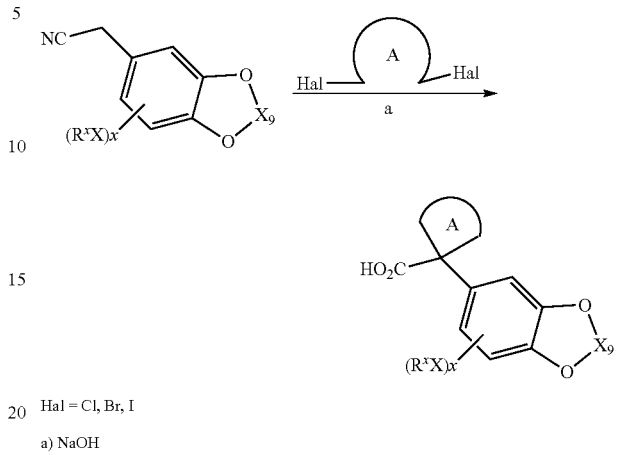

Hal = Cl, Br, I a) NaOH

Preparation of Amine Moities

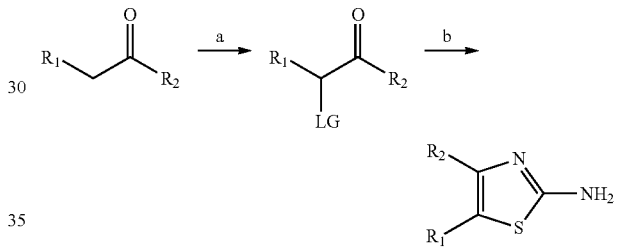

a) Br$_2$ or NBS, EtOAc, Mg(ClO$_4$)$_2$ (LG = Br); b) H$_2$NCSNH$_2$

Preparation of Amine Moieties

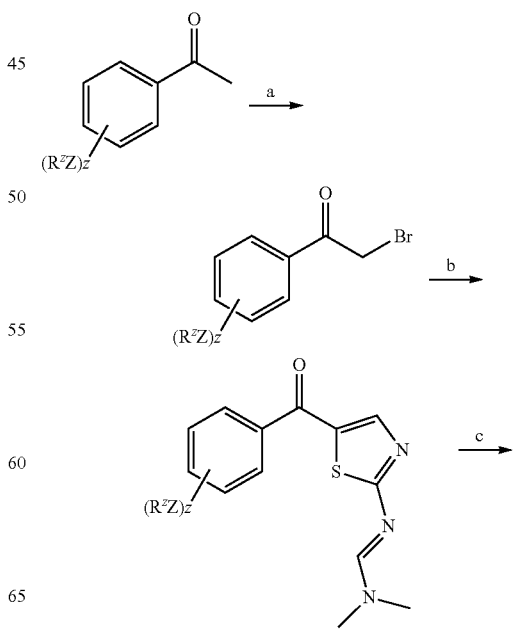

143
-continued

144
-continued

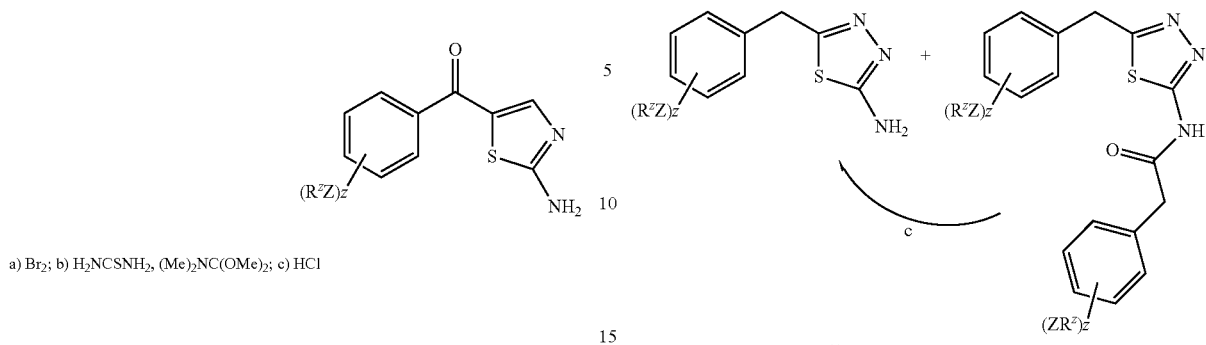

a) Br$_2$; b) H$_2$NCSNH$_2$, (Me)$_2$NC(OMe)$_2$; c) HCl a) H$_2$N—NHCONH$_2$, POCl$_3$; b) H$_2$N—NHCSNH$_2$, POCl$_3$; c) HCl

Preparation of Amine Moieties

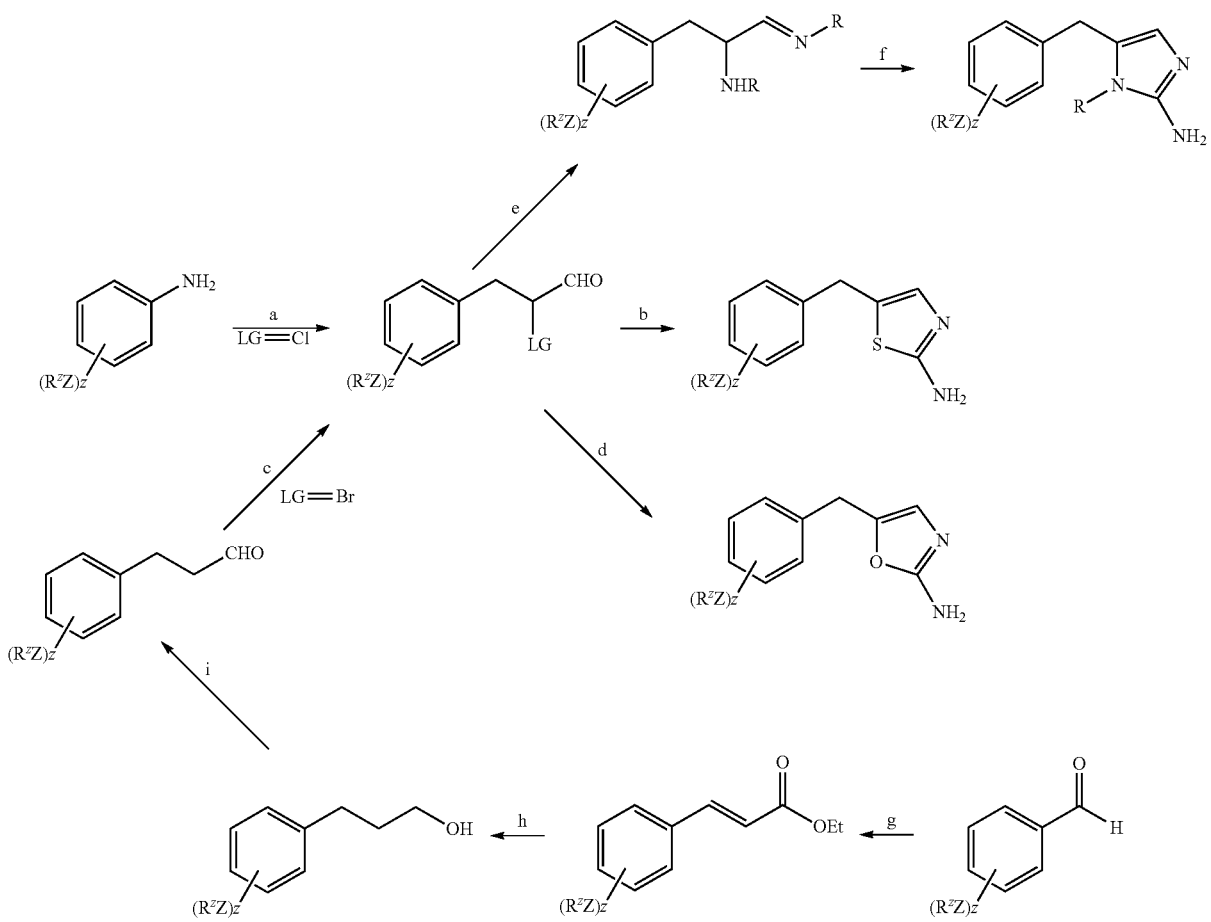

a) NaNO$_2$, CuCl$_2$, CH$_2$=CHCHO (LG=Cl); b) H$_2$NCSNH$_2$; c) Br$_2$, CH$_2$Cl$_2$ (LG = Br); d) H$_2$NCONH$_2$;
e) RNH$_2$, MeOH (R = alkyl); f) NH$_2$CN, H$_2$SO$_4$; g) EtO$_2$CCH$_2$P(O)(OEt)$_2$, NaH; h) LAH; i) SO$_3$•Pyridine SO$_3$ Preparation of Amine Moieties Preparation of Amine Moieties

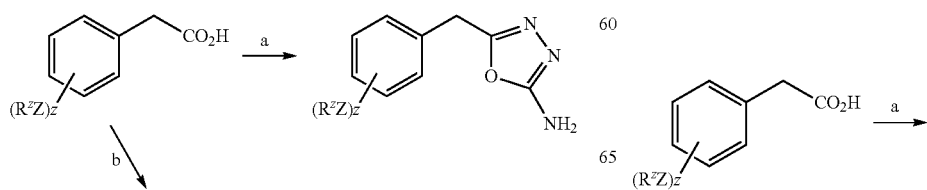

145
-continued
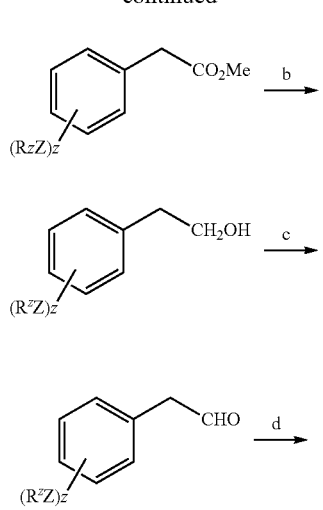
146
-continued
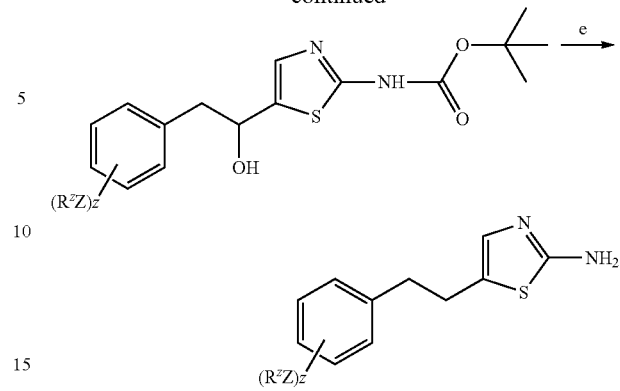
a) $K_2CO_3$, MeI; b) LAH; c) $SO_3$·Pyridine; d) n-BuLi, tert-butyl thiazol-2-ylcarbamate; e) $Et_3SiH$, TFA.
Preparation of Compounds of Formula VA-1 and Formula VA-4
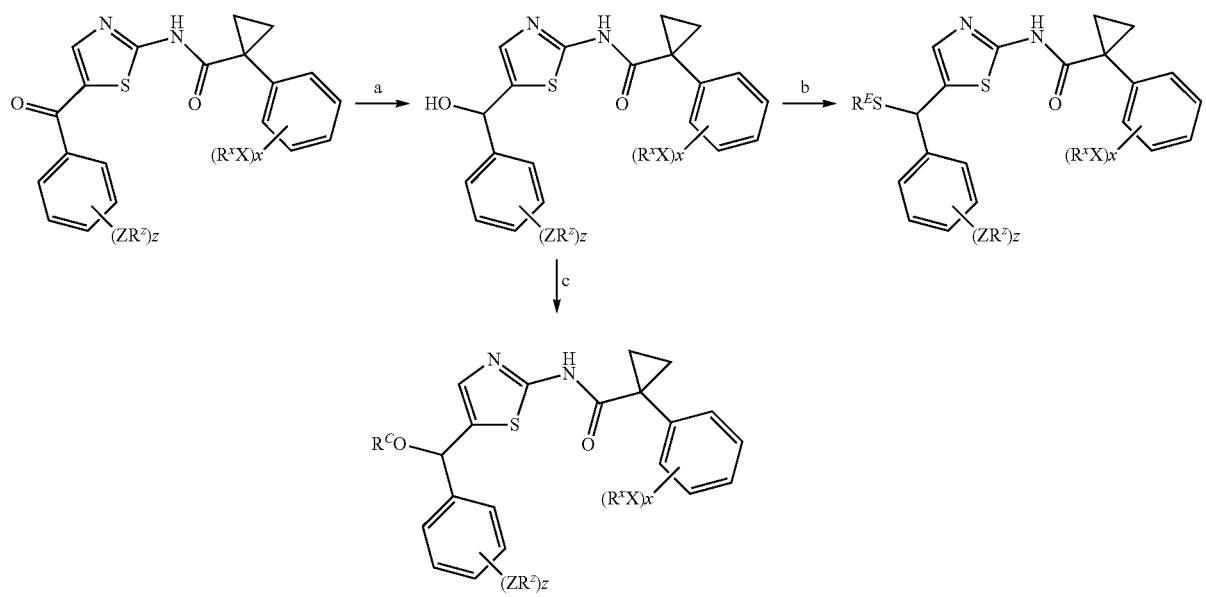
a) $NaBH_4$, MeOH; b) $R^E SH$, TFA; c) $R^C OH$, pTSOH, ΔT.
Preparation of Compounds of Formula VA-2 and Formula VA-3
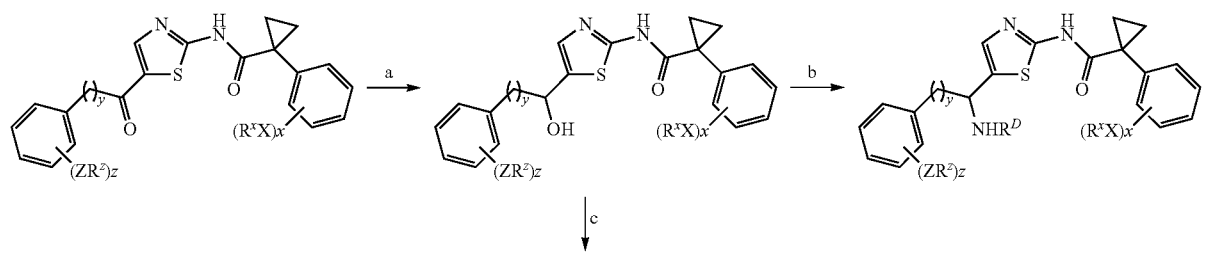

-continued
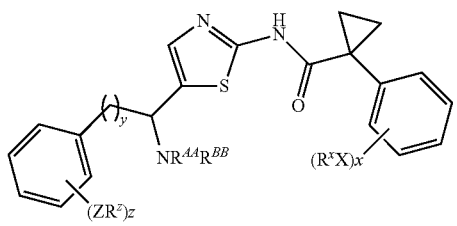
a) NaBH$_4$, MeOH; b) i) MsCl, Et$_3$N; ii) NH$_2$R$^D$; c) i) MsCl, Et$_3$N; ii) NHR$^{AA}$R$^{BB}$
Preparation of Compounds of Formula VB-1 and Formula VB-4
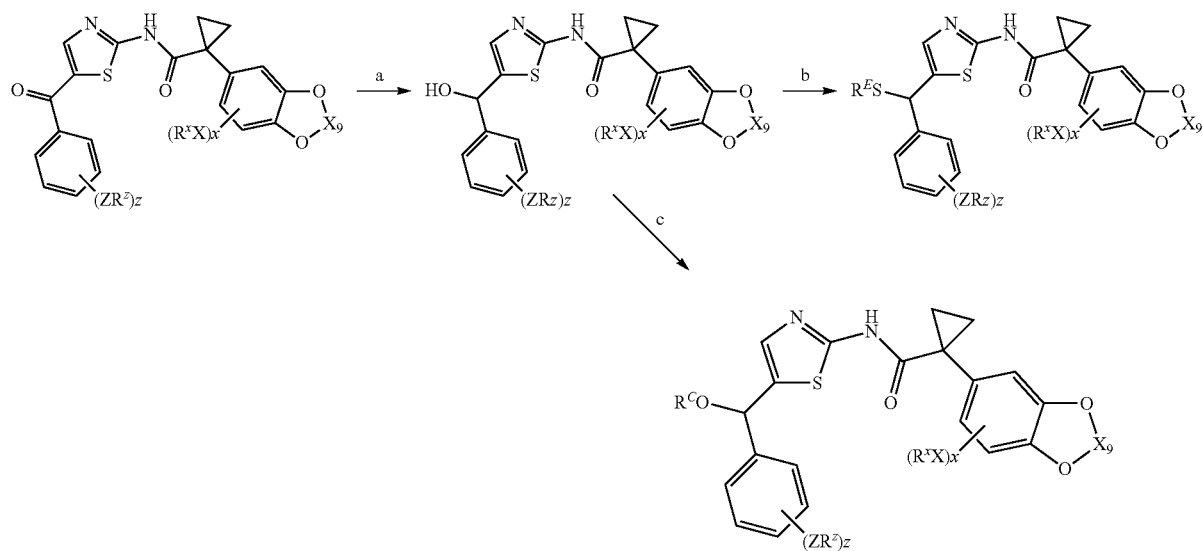
a) NaBH$_4$, MeOH; b) R$^E$SH, TFA; c) R$^C$OH, pTSOH, ΔT
Preparation of Compounds of Formula VB-2 and Formula VB-3
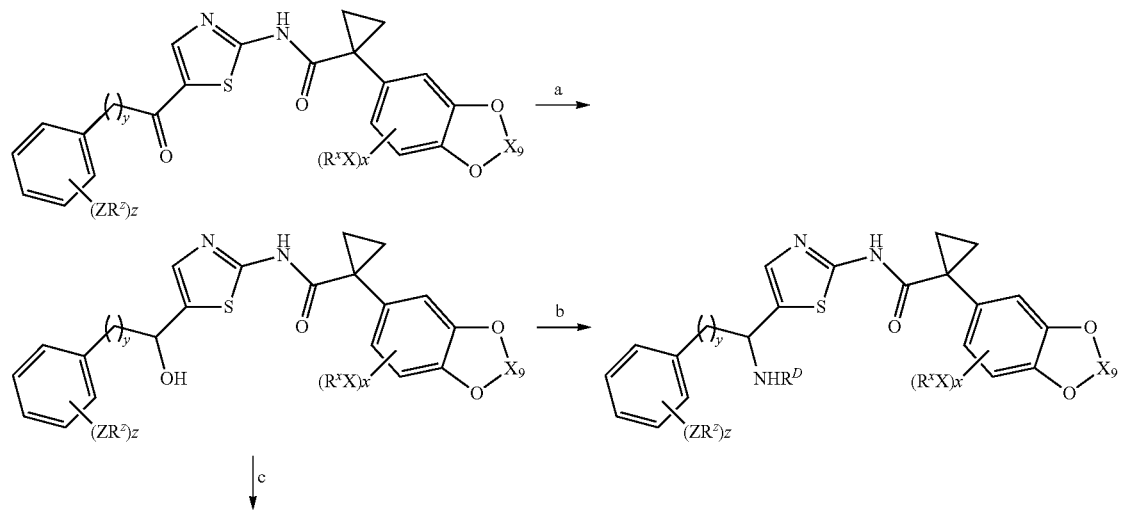

-continued

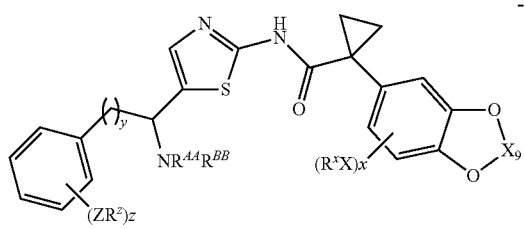

a) NaBH$_4$, MeOH; b) i) MsCl, Et$_3$N; ii) NH$_2$R$^D$; e) i) MsCl, Et$_3$N; ii) NHR$^{AA}$R$^{BB}$

Example 1

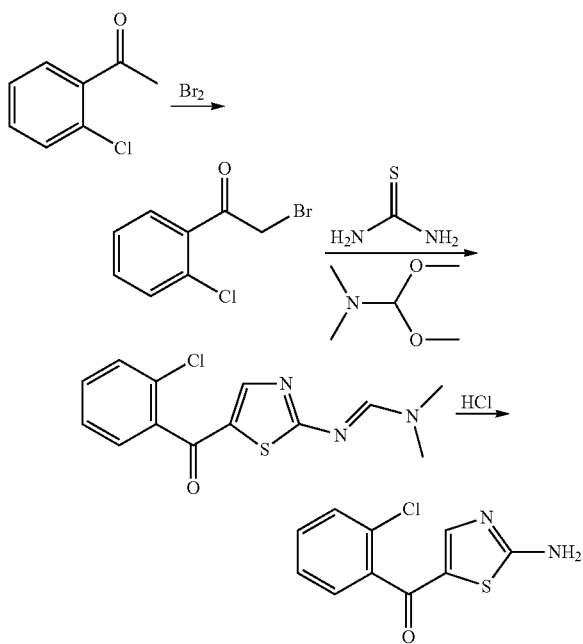

2-Bromo-1-(chloro-phenyl)-ethanone Bromine (3.8 mL, 65 mmol) was added dropwise to a solution of 1-(2-chloro-phenyl)-ethanone (10 g, 65 mmol) in acetic acid (75 mL) at 0° C. The mixture was then warmed to room temperature and stirred overnight. The mixture was evaporated to dryness and used in the next step without further purification.

N'-[5-(2-Chloro-benzoyl)-thiazol-2-yl]-N,N-dimethyl-formamidine. A mixture of thiourea (4.95 g, 65.0 mmol) and dimethoxymethyl-dimethyl-amine (23.2 g, 195 mmol) in methanol (80 mL) was heated at reflux for 30 minutes. After allowing the mixture to cool, triethylamine (19.8 g, 195 mmol) and a solution of 2-bromo-1-(chloro-phenyl)-ethanone (crude from last step) in methanol (50 mL) were added. The mixture was heated at reflux for 4 hours. The solvent was removed and the residue was used directly in the next procedure.

(2-Amino-thiazol-5-yl)-(2-chloro-phenyl)-methanone The crude N'-[5-(2-chloro-benzoyl)-thiazol-2-yl]-N,N-dimethyl-formamidine was dissolved in 10% hydrochloric acid (150 mL) and heated at 70° C. for 4 hours. The precipitate was filtered, washed with ether, and then suspended in a 10% sodium carbonate solution (250 mL). The suspension was stirred for 1 hour and the precipitate was filtered, washed with ether, and dried in air to give (2-amino-thiazol-5-yl)-(2-chloro-phenyl)-methanone as a brown solid (8.5 g, 36 mmol, 55% from 1-(2-chloro-phenyl)-ethanone). ESI-MS m/z calc. 238.0. found 239.3 (M+1)$^{+1}$; $^1$H NMR (DMSO) δ 7.25 (s, 1H), 7.42-7.55 (m, 4H), 8.35 (s, 2H).

(2-Amino-thiazol-5-yl)-(2-methoxy-phenyl)-methanone (2-Amino-thiazol-5-yl)-(2-methoxy-phenyl)-methanone was prepared in a manner analogous to that of (2-amino-thiazol-5-yl)-(2-chloro-phenyl)-methanone (92% yield). ESI-MS m/z calc. 234.1, found; 235.1 (M+1)$^{+1}$; $^1$H NMR (CDCl$_3$) δ 7.37-7.7.47 (m, 3H), 6.98-7.04 (m, 2H), 5.77 (br, 1H), 3.82 (s, 3H).

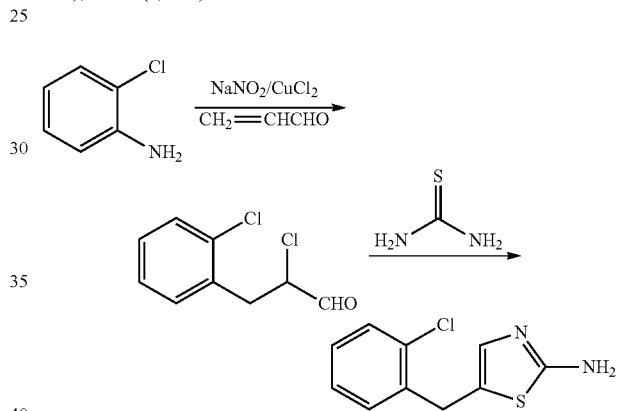

2-Chloro-3-(2-chloro-phenyl)-propionaldehyde To a solution of 2-chloroaniline (12.7 g, 100 mmol) in hydrochloric acid (20% aqueous solution, 40 mL) was added dropwise a solution of sodium nitrite (7.5 g, 110 mmol) in water (20 mL) at 0 to 5° C. After stirring for 10 minutes, a cooled solution of acrolin (15 g, 270 mmol) in acetone (100 mL) containing calcium oxide (2.0 g, 36 mmol) was added gradually, and then followed by a solution of cuprous chloride (1 g, 10 mmol) in acetone (10 mL) containing hydrochloric acid (20% aqueous solution, 2 mL). The mixture was stirred at 0 to 30° C. for 3 hours and then extracted three times with dichloromethane (100 mL). The combined organic layers were washed with a saturated aqueous solution of sodium bicarbonate followed by a saturated aqueous solution of sodium chloride. The organic layer was separated, dried over sodium sulfate, and evaporated to dryness to give a black viscous oil. The crude product was passed through a short silica gel column to give 12 g of crude product, which was used directly in the next step.

5-(2-Chloro-benzyl)-thiazol-2-ylamine A mixture of 2-chloro-3-(2-chloro-phenyl)-propionaldehyde (12 g, crude from above) and urea (6.0 g, 0.10 mol) in ethanol (120 mL) was heated at reflux overnight. The solvent was evaporated to dryness. The residue was diluted with dichloromethane (120 mL) and then washed with sodium hydroxide (10% aqueous solution, 50 mL) and water (30 mL). The organic layer was washed three times with hydrochloric acid (5% aqueous solution, 120 mL). The combined aqueous layer was adjusted to pH 9-10 with a 10% aqueous solution of sodium hydroxide and then extracted three times with dichloromethane (150 mL). The organic layers were combined, dried over sodium sulfate, evaporated to dryness, and purified by silica gel column chromatography to yield a yellow solid (5.2 g, 0.023 mol, 23% from 2-chloroaniline). ESI-MS m/z calc. 224.0. found 225.2 (M+1)$^+$; $^1$H NMR (CDCl$_3$) δ 4.07 (s, 2H), 4.90 (bs, 2H), 6.80 (s, 1H), 7.37-7.15 (m, 4H).

5-(2-methoxy-benzyl)-thioazol-2-ylamine 5-(2-Methoxy-benzyl)-thioazol-2-ylamine was prepared in a manner analogous to that of 5-(2-chloro-benzyl)-thiazol-2-ylamine. ESI-MS m/z calc. 220.1. found 221.2 (M+1)$^+$; $^1$H NMR (CDCl$_3$) δ 7.26-7.19 (m, 1H), 7.15 (d, J=6.8 Hz, 1H), 6.90-6.85 (m, 2H), 6.79 (s, 1H), 4.77 (bs, 2H), 3.93 (s, 2H), 3.84 (s, 3H).

5-(3-Chloro-benzyl)-thioxazol-2-ylamine 5-(3-Chloro-benzyl)-thioxazol-2-ylamine was prepared in a manner analogous to that of 5-(2-chloro-benzyl)-thiazol-2-ylamine. ESI-MS m/z calc. 224.0. found 225.2 (M+1)$^+$; $^1$H NMR (CDCl$_3$) δ 7.26-7.21 (m, 3H), 7.10 (d, J=6.8 Hz, 1H), 6.81 (s, 1H), 4.82 (bs, 2H), 3.93 (s, 2H).

5-(4-Chloro-benzyl)-thioxazol-2-ylamine 5-(4-Chloro-benzyl)-thioxazol-2-ylamine was prepared in a manner analogous to that of 5-(2-chloro-benzyl)-thiazol-2-ylamine. ESI-MS m/z calc. 224.0. found 225.2 (M+1)$^+$; $^1$H NMR (CDCl$_3$) δ 7.26 (d, J=8.4 Hz, 2H), 7.14 (d, J=8.4 Hz, 2H), 6.79 (s, 1H), 4.85 (bs, 2H), 3.92 (s, 2H).

5-(2-Cyano-benzyl)-thiazol-2-ylamine 5-(2-Cyano-benzyl)-thiazol-2-ylamine was prepared in a manner analogous to that of 5-(2-chloro-benzyl)-thiazol-2-ylamine (12 g, 56 mmol, 11% from 2-cyanoaniline). ESI-MS m/z calc. 215.05. found 216.16 (M+1)$^+$; $^1$H NMR (CDCl$_3$) δ 7.64 (d, 1H), 7.54 (t, 1H), 7.34 (m, 2H), 6.87 (s, 1H), 4.89 (br, 2H), 4.19 (s, 2H).

5-(2-Chloro-3-fluoro-benzyl)-thiazol-2-ylamine 5-(2-Chloro-3-fluoro-benzyl)-thiazol-2-ylamine was prepared in a manner analogous to that of 5-(2-chloro-benzyl)-thiazol-2-ylamine (4.0 g, 16 mmol, 12% from 2-chloro-6-fluoroaniline). ESI-MS m/z calc. 242.07. found 243.14 (M+1)$^+$; $^1$H NMR (CDCl$_3$) δ 7.17 (m, 1H), 7.04 (m, 2H), 6.82 (s, 1H), 4.86 (br, 2H), 4.09 (s, 2H).

5-(2-Chloro-4-fluoro-benzyl)-thiazol-2-ylamine 5-(2-Chloro-4-fluoro-benzyl)-thiazol-2-ylamine was prepared in a manner analogous to that of 5-(2-chloro-benzyl)-thiazol-2-ylamine (11.5 g, 47.4 mmol, 30% from 2-chloro-4-fluoroaniline). ESI-MS m/z calc. 242.01. found 243.27 (M+1)$^+$; $^1$H NMR (CDCl$_3$) δ 9.34 (br, 2H), 7.48 (m, 2H), 7.24 (m, 1H), 7.07 (s, 1H), 4.04 (s, 2H).

5-(2-Chloro-5-fluoro-benzyl)-thiazol-2-ylamine 5-(2-Chloro-5-fluoro-benzyl)-thiazol-2-ylamine was prepared in a manner analogous to that of 5-(2-chloro-benzyl)-thiazol-2-ylamine (7.8 g, 32 mmol, 20% from 2-chloro-5-fluoroaniline). ESI-MS m/z calc. 242.01. found 243.36 (M+1)$^+$; $^1$H NMR (DMSO-d$_6$) δ 9.25 (s, 2H), 7.52 (q, 1H), 7.36 (dd, 1H), 7.21 (dt, 1H), 7.10 (s, 1H), 4.05 (s, 2H).

Example 2

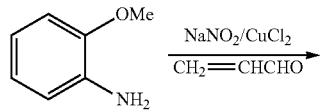

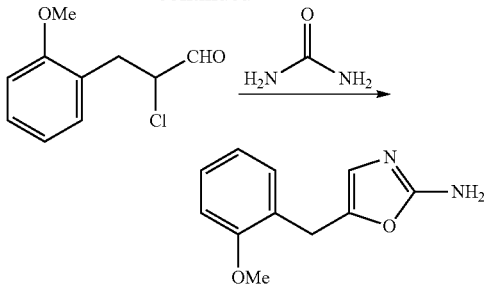

2-Chloro-3-(2-methoxy-phenyl)-propionaldehyde A solution of 2-methoxylaniline (24.6 g, 0.200 mol) in hydrochloric acid (20% aqueous solution, 80 mL) was slowly added to a solution of sodium nitrite (15 g, 0.22 mol) in water (40 mL) at 0 to 5° C. After stirring for 10 minutes, a cooled solution of acrolin (30 g, 0.56 mol) in acetone (200 mL) containing calcium oxide (4.0 g, 72 mmol) was added gradually, and then followed by a solution of cuprous chloride (2.0 g, 20 mmol) in acetone (20 mL) containing hydrochloric acid (20% aqueous solution, 4 mL). The mixture was stirred at 0 to 30° C. for 3 hours, and then extracted with three 150 mL portions of dichloromethane. The combined organic layers were washed with a saturated aqueous solution of sodium bicarbonate, a saturated aqueous solution of sodium chloride, dried over sodium sulfate, filtered, and concentrated to give a black viscous oil. The crude product was passed through a short silica column to give 10 g of crude product, which was used directly in the next procedure.

5-(2-Methoxy-benzyl)-oxazol-2-ylamine A mixture of 2-chloro-3-(2-methoxylphenyl)-propionaldehyde (10 g, crude from above) and urea (9.6 g, 0.16 mol) was dissolved in ethanol (250 mL) and then heated at reflux overnight. The solvent was evaporated to dryness. The residue was diluted with dichloromethane (250 mL) and then washed with sodium hydroxide (10% aqueous solution, 100 mL) and water (50 mL). The organic layer was extracted three times with hydrochloric acid (5% aqueous solution, 250 mL). The combined aqueous layers were adjusted to pH 9 to 10 with a 10% aqueous solution of sodium hydroxide and then extracted three times with dichloromethane (300 mL). The organic layer was separated, dried over sodium sulfate, and evaporated to dryness. The crude product was purified by silica gel column chromatography to yield the yellow-red solid product (0.72 g, 0.35% from 2-methoxyaniline). ESI-MS m/z calc. 204.1. found 205.1 (M+1)$^+$; $^1$H NMR (CDCl$_3$) δ 7.26-7.20 (m, 1H), 7.14 (d, J=7.2 Hz, 1H), 6.91-6.86 (m, 2H), 6.35 (s, 1H), 4.49 (bs, 2H), 3.85 (s, 2H), 3.82 (s, 3H).

5-(2-Chloro-benzyl)-oxazol-2-ylamine. 5-(2-Chloro-benzyl)-oxazol-2-ylamine was prepared in a manner analogous to that of the preparation of 5-(2-methoxy-benzyl)-oxazol-2-ylamine to yield the product as a yellow solid (3.5 g, 8.4% from 2-chloroaniline). ESI-MS m/z calc. 208.0, found 209.1 (M+1)$^+$; $^1$H NMR CDCl$_3$) δ 7.37-7.18 (m, 4H), 6.40 (s, 1H), 4.66 (bs, 2H), 3.97 (s, 2H).

5-(3-Chloro-benzyl)-oxazol-2-ylamine 5-(3-Chloro-benzyl)-oxazol-2-ylamine was prepared in a manner analogous to that of the preparation of 5-(2-methoxy-benzyl)-oxazol-2-ylamine to yield the product as a yellow solid (1.2 g, 2.9% from 3-chloroaniline). ESI-MS m/z calc. 208.0, found 209.2 (M+1)$^+$; $^1$H NMR (CDCl$_3$) δ 7.26-7.22 (m, 3H), 7.10 (d, J=6.0 Hz, 1H), 6.44 (s, 1H), 4.73 (bs, 2H), 3.82 (s, 2H).

5-(4-Chloro-benzyl)-oxazol-2-ylamine 5-(4-Chloro-benzyl)-oxazol-2-ylamine was prepared in a manner analogous to that of the preparation of 5-(2-methoxy-benzyl)-oxazol-2-ylamine to yield the product as a yellow solid (1.6 g, 4% from 4-chloroaniline). ESI-MS m/z calc. 208.0. found 209.1 (M+1)⁺; ¹H NMR (CDCl₃) δ 7.27 (d, J=8.4 Hz, 2H), 7.17 (d, J=8.0 Hz, 2H), 6.38 (s, 1H), 4.66 (bs, 2H), 3.81 (s, 2H).

Example 3

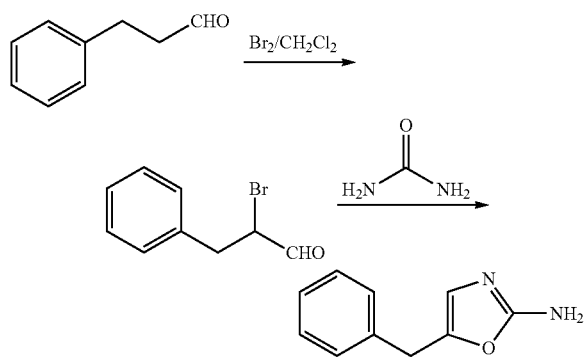

2-Bromo-3-phenylpropionaldehyde A solution of bromine (15.2 g, 95.1 mmol) in 30 mL of dichloromethane was added to a solution of 3-phenyl-propionaldehyde (13.4 g, 100 mmol) in dichloromethane (150 mL) at 0° C. over 20 minutes. The reaction mixture was allowed to stir for 2 hours and then a saturated aqueous solution of sodium bicarbonate (100 mL) was added to the mixture. The organic layer was separated and the aqueous layer was washed with dichloromethane (50 mL). The combined organic layers were washed with water, a saturated aqueous solution of sodium chloride, and then evaporated to dryness to give an orange oil (14.2 g), which was used directly in the next step.

5-Benzyl-oxazol-2-ylamine A mixture of 2-bromo-3-phenylpropionaldehyde (14.2 g, crude from above) and urea (7.2 g, 0.12 mol) were heated at reflux for 15 hours in 200 mL of ethanol. The solvent was evaporated to dryness and the residue was diluted with dichloromethane (250 mL) and then washed with sodium hydroxide (10% aqueous solution, 100 mL) and water (50 mL). The organic layer was washed three times with hydrochloric acid (5% aqueous solution, 250 mL). The combined aqueous layers were brought to pH 9 to 10 with a 10% aqueous solution of sodium hydroxide and then extracted three times with dichloromethane (300 mL). The organic layer was dried over sodium sulfate, evaporated to dryness, and purified by silica gel column chromatography to give a pale yellow solid (1.6 g, 9.2 mmol, 9.2% from 3-phenyl-propionaldehyde). ESI-MS m/z calc. 174.1. found 175.1 (M+1)⁺; ¹H NMR (CDCl₃) δ 7.32-7.22 (m, 5H), 6.39 (s, 1H), 4.72 (bs, 2H), 3.84 (s, 2H).

Example 4

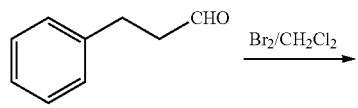

-continued

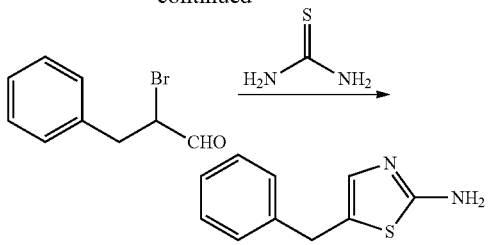

2-Bromo-3-phenylpropionaldehyde A solution of bromine (15.2 g, 95.1 mmol) in 30 mL of dichloromethane was added to a solution of 3-phenyl-propionaldehyde (13.4 g, 100 mmol) in dichloromethane (150 mL) at 0° C. over 20 minutes. The reaction mixture was allowed to stir for 2 hours and then a saturated aqueous solution of sodium bicarbonate (100 mL) was added to the mixture. The organic layer was separated and the aqueous layer was washed with dichloromethane (50 mL). The combined organic layers were washed with water, a saturated aqueous solution of sodium chloride, and then evaporated to dryness to give an orange oil (14.2 g), which was used directly in the next step.

5-Benzyl-thioxazol-2-ylamine A mixture of 2-bromo-3-phenylpropionaldehyde (14.2 g, crude from above) and urea (7.2 g, 0.12 mol) were heated at reflux for 15 hours in 200 mL of ethanol. The solvent was evaporated to dryness and the residue was diluted with dichloromethane (250 mL) and then washed with sodium hydroxide (10% aqueous solution, 100 mL) and water (50 mL). The organic layer was washed three times with hydrochloric acid (5% aqueous solution, 250 mL). The combined aqueous layers were brought to pH 9 to 10 with a 10% aqueous solution of sodium hydroxide and then extracted three times with dichloromethane (300 mL). The organic layer was dried over sodium sulfate, evaporated to dryness, and purified by silica gel column chromatography to give a pale yellow solid (5.2 g, 27 mmol, 27% from 3-phenyl-propionaldehyde). ESI-MS m/z calc. 190.1. found 191.2 (M+1)⁺; ¹H NMR (CDCl₃) δ 7.32-7.21 (m, 5H), 6.79 (s, 1H), 4.91 (bs, 2H), 3.95 (s, 2H).

Example 5

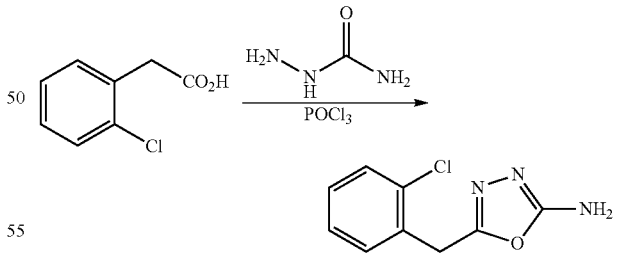

5-(2-Chloro-benzyl)-[1,3,4]oxadiazol-2-ylamine Semicarbazide (9.0 g, 120 mmol) was slowly added to a solution of (2-chlorophenyl)acetic acid (10 g, 60 mmol) in phosphorus oxychloride (50 mL). The mixture was stirred at room temperature for 16 hours and then poured into crushed ice (500 g). A viscous solid was decanted from the aqueous layer and then the aqueous layer was adjusted to pH 4 to 5 with sodium hydroxide (50% aqueous solution). The resulting precipitate was filtered and then washed with sodium carbonate (10% aqueous solution, 100 mL) to give the product as a white solid (5.9 g, 28 mmol, 47%). ESI-MS m/z calc. 209.0. found 210.1 (M+1)+; $^1$H NMR (DMSO) δ 7.44-7.30 (m, 4H), 6.88 (s, 2H), 4.13 (s, 2H).

Example 6

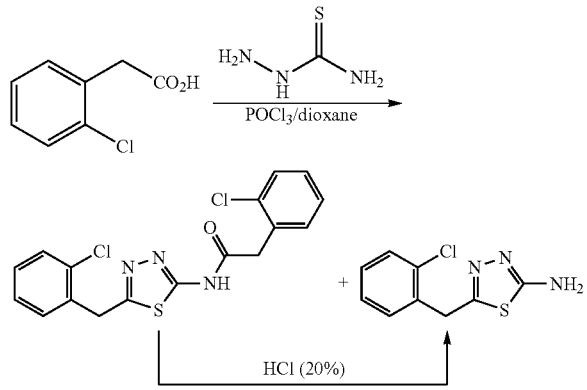

5-(2-Chloro-benzyl)-[1,3,4]thiadiazol-2-ylamine A solution of phosphorous oxychloride (16.6 g, 108 mmol) in 1,4-dioxane (50 mL) was added over a period of 30 minutes to a suspension of (2-chlorophenyl)acetic acid (25.0 g, 147 mmol) and thiosemicarbazide (13.3 g, 147 mmol) in 1,4-dioxane (350 mL) at 90° C. The mixture was stirred at 90° C. for an additional 1.5 hours and then the solvent was evaporated to dryness. The residue was treated with water (300 mL) and then made strongly basic with sodium hydroxide (30% aqueous solution). The solid was filtered and then washed with ethyl acetate. The ethyl acetate layer was evaporated to give a mixture of 5-(2-chloro-benzyl)-[1,3,4]thiadiazol-2-ylamine and N-[5-(2-chloro-benzyl)-[1,3,4]thiadiazol-2-yl]-2-(2-chloro-phenyl)-acetamide as a pale-yellow solid (13.2 g). The solid was refluxed in a mixture of hydrochloric acid (20% aqueous solution, 250 mL) and ethanol (50 mL) for 15 hours and then cooled to room temperature. The resulting precipitate was collected and then washed with sodium carbonate (10% aqueous solution, 50 mL) to give 5-(2-chloro-benzyl)-[1,3,4]thiadiazol-2-ylamine as a white solid (5.2 g, 23 mmol, 16%). ESI-MS m/z calc. 225.0. found 226.1 (M+1)+; $^1$H NMR (DMSO) δ 7.48-7.32 (m, 4H), 4.29 (s, 2H).

Example 7

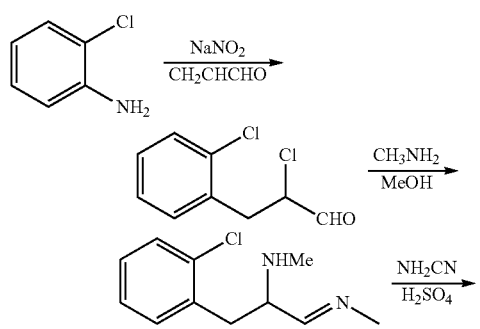

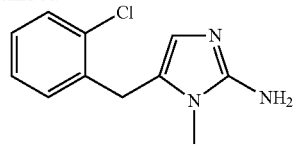

2-Chloro-3-(2-chloro-phenyl)-propionaldehyde A solution of sodium nitrite (15 g, 0.22 mol) in water (40 mL) was slowly added to a solution of 2-chloroaniline (25.5 g, 0.200 mol) in hydrochloric acid (20% aqueous solution, 100 mL) at 0 to 5° C. The mixture was stirred for ten minutes and then poured into a cooled solution of acrolein (30 g, 0.56 mol) in acetone (200 mL) containing calcium oxide (4.0 g, 72 mmol), followed by a solution of cuprous chloride (2.0 g, 20 mmol) in acetone (20 mL) containing hydrochloric acid (20% aqueous solution, 4 mL). The mixture was stirred for 3 hours at room temperature, and then extracted three times with dichloromethane (150 mL). The combined organic layers were washed with a solution of saturated aqueous sodium chloride, dried over sodium sulfate, filtered, and evaporated to dryness to give a black viscous oil that was used directly in the next procedure.

[2-(2-Chloro-phenyl)-1-methyliminomethyl-ethyl]-methyl-amine A solution of methylamine in methanol (27%, 69 g) was slowly added to a solution of 2-chloro-3-(2-chlorophenyl)-propionaldehyde in dichloromethane (20 mL). The reaction mixture was allowed to stir for 12 hours and then used immediately in the next procedure.

5-(2-Chloro-benzyl)-1-methyl-1H-imidazol-2-ylamine A solution of cyanamide in water (50%, 150 mL) was added to a boiling solution of [2-(2-chloro-phenyl)-1-methyliminomethyl-ethyl]-methyl-amine in methanol and dichloromethane. The pH was brought to 4.5 by continual addition of an aqueous solution of sulfuric acid (9M). The mixture was refluxed for 2 hours, allowed to cool to room temperature, and adjusted to pH 9 through the addition of powdered sodium bicarbonate. The mixture was washed three times with dichloromethane (200 mL) and the combined organic layers were extracted three times with hydrochloric acid (20% aqueous solution, 150 mL). The aqueous solution was adjusted to pH 10 with sodium hydroxide (10% aqueous solution) and extracted three times with dichloromethane (150 mL). The combined organic layers were washed with a saturated aqueous solution of sodium chloride, dried over sodium sulfate, filtered, and evaporated to dryness to give a black solid which was purified by column chromatography to yield the product (5.0 g, 0.23 mmol, 11% from 2-chloroaniline) as a brown solid. ESI-MS m/z calc. 221.1. found 222.3 (M+1)+; $^1$H NMR (CDCl$_3$) δ 7.30-7.37 (m, 1H), 7.15-7.18 (m, 2H), 7.03-7.06 (m, 1H), 6.43 (s, 1H), 3.94 (s, 2H), 3.80 (br, 2H), 3.15 (s, 3H).

Example 8

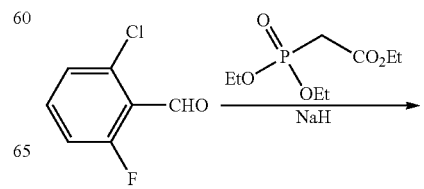

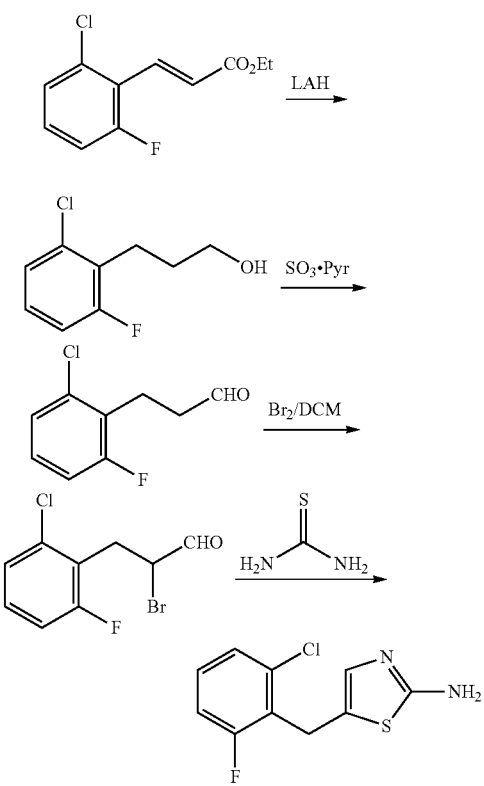

3-(2-Chloro-6-fluoro-phenyl)-acrylic acid ethyl ester A solution of (diethoxyphosphoryl)-acetic acid ethyl ester (87 g, 0.39 mol) in tetrahydrofuran (100 mL) was slowly added to a suspension of sodium hydride (60% in mineral oil, 15 g, 0.39 mol) in tetrahydrofuran (200 mL) at 0° C. After stirring for 20 minutes, a solution of 2-chloro-6-fluoro-benzaldehyde (40 g, 0.26 mol) in tetrahydrofuran (100 mL) was added while maintaining the temperature at 0° C. The mixture was heated at 50° C. for 1 hour and then cooled to room temperature. The reaction was quenched by addition of a saturated aqueous solution of ammonium chloride (300 mL). The layers were separated and the aqueous layer was extracted with ether. The combined organic layers were washed with a saturated aqueous solution of sodium chloride, dried over sodium sulfate, and evaporated to dryness to give 3-(2-chloro-6-fluoro-phenyl)-acrylic acid ethyl ester, which was used directly in the next step. $^1$H NMR (CDCl$_3$) δ 7.89 (d, 1H, J=16.4 Hz), 7.26-7.06 (m, 2H), 7.06-7.02 (m, 1H), 6.72 (d, 1H, J=16.4 Hz), 4.28 (q, 2H, J=7.6 Hz), 1.34 (t, 3H, J=7.6 Hz).

3-(2-Chloro-6-fluoro-phenyl)-propan-1-ol A solution of 3-(2-chloro-6-fluoro-phenyl)-acrylic acid ethyl ester in dried tetrahydrofuran (300 mL) was added to a suspension of lithium aluminum hydride (30 g, 0.78 mol) in anhydrous tetrahydrofuran (200 mL) at 0° C. The reaction mixture was stirred for 3 hours, and then cooled to 0° C. and quenched by the addition of water (30 g) and a 10% aqueous solution of sodium hydroxide (30 mL). The resulting solid was filtered, washed with tetrahydrofuran, and then purified by silica gel column chromatography to afford 3-(2-chloro-6-fluoro-phenyl)-propan-1-ol (21 g, 0.11 mol, 43% from 2-chloro-6-fluoro-benzaldehyde).

3-(2-Chloro-6-fluoro-phenyl)-propionaldehyde A solution of pyridine complex with sulfur trioxide (40.4 g, 0.225 mol) in dimethylsulfoxide (50 mL) was slowly added to a solution of 3-(2-chloro-6-fluoro-phenyl)-propan-1-ol (20.6 g, 0.109 mol) and triethylamine (25.8 g, 0.225 mol) in dichloromethane (250 mL) at 0° C. The reaction was allowed to stir for 30 minutes, and then it was poured into a saturated aqueous solution of sodium chloride and extracted with ethyl acetate. The combined organic layers were washed twice with water and then with a saturated aqueous solution of sodium chloride, dried over magnesium sulfate and evaporated to dryness. The crude product was purified by silica gel chromatography to afford 3-(2-chloro-6-fluoro-phenyl)-propionaldehyde (15 g, 80 mmol, 74%), $^1$H NMR (CDCl$_3$) δ 9.83 (s, 1H), 7.24-7.00 (m, 2H), 6.99-6.94 (m, 1H), 3.13-3.09 (m, 2H), 2.75-2.71 (m, 2H).

2-Bromo-3-(2-chloro-6-fluoro-phenyl)-propionaldehyde A solution of bromine (11 g, 0.081 mol) in dichloromethane (50 mL) was slowly added to a solution of 3-(2-chloro-6-fluoro-phenyl)-propionaldehyde (15 g, 0.081 mol) in dichloromethane (250 mL) at 0° C. The mixture was stirred overnight at room temperature and then the solvent was removed to give the crude product which was used directly in the next step.

5-(2-Chloro-6-fluoro-benzyl)-thiazol-2-ylamine A mixture of 2-bromo-3-(2-chloro-6-fluoro-phenyl)-propionaldehyde (crude from last step) and thiourea (6.4 g, 0.084 mol) in ethanol (250 mL) was refluxed overnight. The reaction mixture was evaporated to dryness and dichloromethane (50 mL) was added to the residue. The mixture was acidified to pH 2-3 with concentrated hydrochloric acid. The precipitated solid was filtered, and washed with dichloromethane to give the product as the hydrochloride salt (7.7 g, 34.1%). ESI-MS m/z calc. 242.0. found 243.2 (M+1)$^+$; $^1$H NMR (CDCl$_3$) δ 8.62 (s, 2H), 7.37-7.36 (m, 2H), 7.29-7.26 (m, 1H), 6.98 (s, 1H), 4.05 (s, 2H).

Example 9

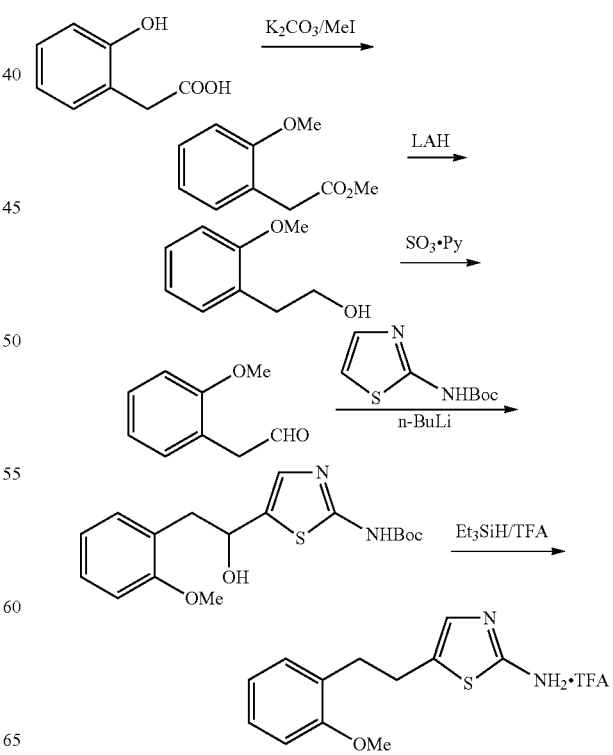

(2-Methoxy-phenyl)-acetic acid methyl ester A solution of methyl iodide (188 g, 1.33 mole) in acetonitrile (200 mL) was slowly added to a mixture of (2-hydroxy-phenyl)-acetic acid (80 g, 0.53 mol) and potassium carbonate (254 g, 1.84 mol) in acetonitrile (800 mL) at reflux. The reaction was heated at reflux for 15 hours. The reaction mixture was cooled and the precipitate was removed by filtration. The filtrate was evaporated to dryness to give the crude product (90 g, 0.50 mol, 94%).

2-(2-Methoxy-phenyl)-ethanol Lithium aluminum hydride (21 g, 0.55 mol) was added to a solution of (2-methoxy-phenyl)-acetic acid methyl ester (90 g, 0.50 mol) in anhydrous tetrahydrofuran (500 mL) at 0° C. After stirred at 0° C. for 30 minutes, the mixture was treated with sodium hydroxide (5% aqueous solution, 180 g). The mixture was extracted three times with ethyl acetate (400 mL) and the combined organic layers were washed with a saturated aqueous solution of sodium chloride, dried over sodium sulfate, filtered, and evaporated to dryness to give 2-(2-methoxy-phenyl)-ethanol (43 g, 0.28 mol, 57%), which was used directly in the next step.

(2-Methoxy-phenyl)-acetaldehyde A solution of pyridine complex with sulfur trioxide (134 g, 0.842 mol) in dimethylsulfoxide (150 mL) was slowly added to a solution of 2-(2-methoxy-phenyl)-ethanol (43 g, 0.28 mol) and triethylamine (86 g, 0.85 mol) in dichloromethane (500 mL) at 0° C. After being stirred 30 min, the mixture was poured into a saturated aqueous solution of sodium chloride and the organic layer was washed with dilute hydrochloric acid, a saturated aqueous solution of sodium chloride, dried over sodium sulfate and evaporated to dryness to give (2-methoxy-phenyl)-acetaldehyde (36 g, 0.24 mol, 86%) which was used in the next step directly.

{5-[1-Hydroxy-2-(2-methoxy-phenyl)-ethyl]-thiazol-2-yl}-carbamic acid tert-butyl ester A solution of n-butyl lithium (2.5 M, 250 mL, 0.62 mol) was added to a solution of N-Boc-2-aminothiazole (56 g, 0.28 mol) in anhydrous tetrahydrofuran (500 mL) was added at −78° C. After the addition was completed, the mixture was allowed to stir at −78° C. for one hour. A solution of (2-methoxy-phenyl)-acetaldehyde (36 g, 0.24 mol) in tetrahydrofuran (100 mL) was slowly added to the reaction mixture while maintaining a temperature of −78° C. The mixture was allowed to warm to room temperature and stirred for 15 hours. The reaction was quenched with a saturated aqueous solution of ammonium chloride (1000 mL) and extracted three times with ethyl acetate (400 mL). The combined organic layers were washed with a saturated aqueous solution of sodium chloride, dried over sodium sulfate, and evaporated to dryness. The crude product was purified by column chromatography to give the pure product (28 g, 0.080 mol, 28%).

5-[2-(2-Methoxy-phenyl)-ethyl]-thiazol-2-ylamine A mixture of {5-[1-hydroxy-2-(2-methoxy-phenyl)-ethyl]-thiazol-2-yl}-carbamic acid tert-butyl ester (28 g, 0.080 mol), triethylsilane (130 g, 1.12 mol) and trifluoroacetic acid (250 g, 2.24 mol) in dichloromethane (500 mL) was stirred at room temperature for 15 hours. The mixture was evaporated to dryness and then stirred in water. The solid was filtered and washed with ether to give 5-[2-(2-methoxy-phenyl)-ethyl]-thiazol-2-ylamine as the trifluoracetic acid salt (11 g, 0.033 mol, yield 42%). ESI-MS m/z cacl. 234.08, found 235.16 (M+1)⁺; ¹H NMR (CDCl₃) δ 8.81 (br, 2H), 7.20 (t, 1H), 7.12 (d, 1H), 6.95 (m, 2H), 6.85 (t, 1H), 3.76 (s, 3H), 2.83 (d, 2H), 2.80 (d, 2H).

Example 10

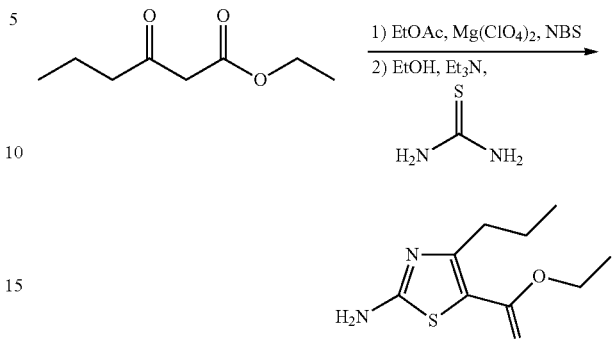

2-Bromo-3-oxo-hexanoic acid ethyl ester 3-Oxo-hexanoic acid ethyl ester (4.0 mL, 25 mmol) and magnesium perchlorate (1.7 g, 7.6 mmol) were placed in 500 mL of ethyl acetate and allowed to stir for 5 minutes. N-Bromosuccinimide (4.7 g, 26 mmol) was added and the reaction mixture was allowed to stir for 15 minutes, at which time thin-layer chromatography (10% ethyl acetate in hexanes, SiO₂, 254 nm irradiation) indicated the reaction was complete. The reaction mixture was diluted with 500 mL of ethyl ether and washed three times with an equal volume of saturated aqueous sodium chloride. The organic layer was then dried over sodium sulfate and evaporated to dryness. This material was used in the next step without further purification.

2-Amino-4-propyl-thiazole-5-carboxylic acid ethyl ester 2-Bromo-3-oxo-hexanoic acid ethyl ester (5.9 g, 25 mmol), was dissolved in 60 mL of ethanol containing triethylamine (4.2 mL, 30 mmol) and thiourea (1.9 g, 25 mmol). The colorless solution was protected from light and allowed to stir for 16 hours. The resulting red suspension was evaporated to dryness and dissolved in a minimum of dichloromethane. This solution was washed three times with an equal volume of a saturated aqueous solution of sodium bicarbonate, followed by a saturated aqueous solution of sodium chloride. The organic layer was separated and filtered to remove a fine red precipitate which remained suspended in the organic phase. The solvent was removed and then the solid was dissolved in a minimum of 50/50 (v/v) ethyl acetate and 1 N aqueous solution of hydrochloric acid. The layers were separated and the aqueous layer was washed with an equal volume of ethyl acetate. After discarding the organic layers, the aqueous layer was then placed in an ice bath with an equal volume of ethyl acetate. Sodium hydroxide (1N) was then slowly added with vigorous swirling until the aqueous phase was basic. The layers were separated and the aqueous layer was washed two additional times with ethyl acetate. The combined organic layers were washed three times with an equal volume of a solution of saturated aqueous sodium bicarbonate followed by a solution of saturated aqueous sodium chloride. The organic layer was then dried over sodium sulfate and evaporated to dryness to yield a pale yellow solid (1.8 g, 8.4 mmol, 34%). ESI-MS m/z calc. 214.1, found 215.3 (M+1)⁺. Retention time 1.90 minutes.

Example 11

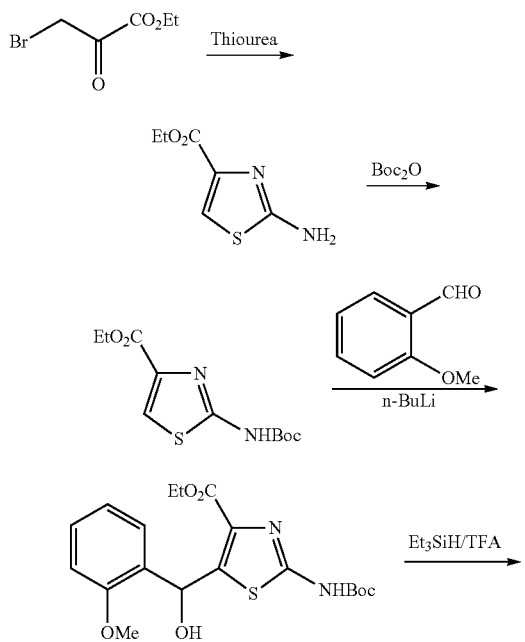

2-Amino-thiazole-4-carboxylic acid ethyl ester A mixture of ethyl bromopyruvate (100 g, 80% purity, 0.41 mol), thiourea (31 g, 0.41 mol) and ethanol (500 mL) was heated at reflux for 12 hours. The solvent was evaporated to dryness and the residue was washed with ether. The solid was suspended in a saturated aqueous solution of sodium bicarbonate (500 mL) for 30 minutes. The solid was filtered, washed with water, and dried over sodium sulfate to give 2-amino-thiazole-4-carboxylic acid ethyl ester (45 g, 0.26 mol, 63%) as an off-white solid.

2-tert-Butoxycarbonylamino-thiazole-4-carboxylic acid ethyl ester Di-tert-butyl dicarbonate (57 g, 0.26 mol) in dichloromethane (100 mL) was slowly added to a solution of 2-amino-thiazole-4-carboxylic acid ethyl ester (45 g, 0.26 mole) and dimethyl-pyridin-4-yl-amine (1 g, 0.008 mol) in dichloromethane (500 mL) at 0° C. The mixture was stirred at room temperature overnight and then diluted with water. The organic layer was washed with a saturated aqueous solution of sodium chloride, dried over sodium sulfate, filtered, and evaporated to dryness to give a crude product. The product was purified by column chromatography to afford the pure product (43 g, 0.16 mol, 62%) as a white solid.

2-tert-Butoxycarbonylamino-5-[hydroxy-(2-methoxyphenyl)-methyl]-thiazole-4-carboxylic acid ethyl ester Butyl lithium (2.5 M, 53 mL, 130 mmol) was slowly added to a solution of 2-tert-butoxycarbonylamino-thiazole-4-carboxylic acid ethyl ester (16.4 g, 60 mmol) in anhydrous tetrahydrofuran (250 mL) at −78° C. under a nitrogen atmosphere. A solution of 2-methoxybenzaldehyde (10.89 g, 79.99 mmol) in tetrahydrofuran (50 mL) was then added dropwise at −78° C. The mixture was warmed slowly to room temperature and stirred for 15 hours. The reaction mixture was quenched with a saturated aqueous solution of ammonium chloride (500 mL). The separated aqueous layer was extracted with ethyl acetate and the combined organic layers were washed with a saturated aqueous solution of sodium chloride, dried over sodium sulfate, filtered, and evaporated to dryness. The crude product was then purified by column chromatography to yield the pure product (12 g, 29 mmol, 48%).

2-Amino-5-(2-methoxy-benzyl)-thiazole-4-carboxylic acid ethyl ester A mixture of 2-tert-butoxycarbonylamino-5-[hydroxy-(2-methoxy-phenyl)-methyl]-thiazole-4-carboxylic acid ethyl ester (12 g, 29 mmol), triethylsilane (52 g, 45 mmol), and trifluoroacetic acid (100 g, 89.6 mmol) in dichloromethane (150 ml) was stirred for 15 hours. The mixture was evaporated to dryness and then diluted with water. The precipitated solid was filtered and washed with water, diethyl ether, and petroleum ether to give the pure target molecule as the trifluoroacetic acid salt (7.6 g, 19 mmol, 64%). ESI-MS m/z calc. 292.09. found 292.25 (M+1)$^+$; $^1$H NMR (CDCl$_3$) δ 7.7 (br, 2H), 7.24 (t, 1H), 7.17 (d, 1H), 6.99 (d, 1H), 6.88 (t, 1H), 4.22-4.25 (m, 4H), 3.78 (s, 3H), 1.26 (t, 3H).

Example 12

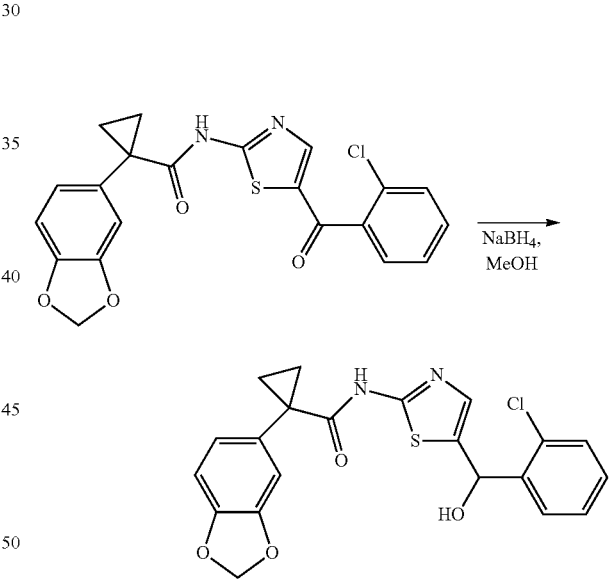

1-Benzo[1,3]dioxol-5-yl-cyclopropanecarboxylic acid {5-[(2-chloro-phenyl)-hydroxy-methyl]-thiazol-2-yl}-amide 1-Benzo[1,3]dioxol-5-yl-cyclopropanecarboxylic acid [5-(2-chloro-benzoyl)-thiazol-2-yl]-amide (1.0 g, 2.3 mmol) was suspended in 150 mL of anhydrous methanol. Sodium borohydride (1.3 g, 35 mmol) was slowly added and the resulting pale yellow solution was allowed to stir for 1 hour at room temperature. The crude product was evaporated to dryness and then dissolved in a minimum of ethyl acetate. The organic was washed three times with an equal volume of 1N hydrochloric acid, saturated aqueous sodium bicarbonate, and saturated aqueous sodium chloride. The organic layer was then dried over sodium sulfate, filtered, and evaporated to dryness to yield the product as a beige solid (0.64 g, 1.5 mmol, 63%). ESI-MS m/z calc. 428.1, found; 429.5 (M+1)+. Retention time 3.17 minutes.

Example 13

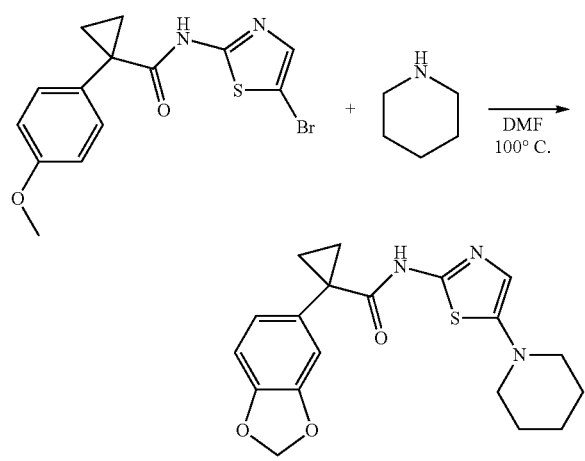

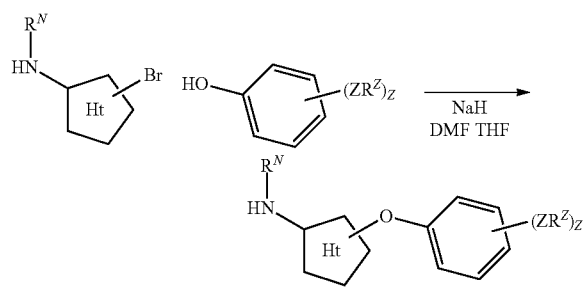

1-Benzo[1,3]dioxol-5-yl-cyclopropanecarboxylic acid (5-piperidin-1-yl-thiazol-2-yl)-amide 1-(4-Methoxy-phenyl)-cyclopropanecarboxylic acid (5-bromo-thiazol-2-yl)-amide (110.4 mg, 0.3125 mmol) was dissolved in 3 mL of N,N-dimethylformamide containing piperidine (148.2 µL, 1.500 mmol). The reaction mixture was placed in a sealed tube and subjected to microwave irradiation for 5 minutes at 100° C. The resulting crude product was purified by reverse-phase preparative liquid chromatography to give the pure product (3.44 mg, 0.00926 mmol, 3%) ESI-MS m/z calc. 371.1. found 372.3 (M+1)+. Retention time 3.29 minutes.

Example 14

General Procedure: The appropriate alcohol (2 equivalents) was dissolved in a solution of 10% N,N-dimethylformamide (DMF) in tetrahydrofuran (THF). Sodium hydride (2.1 equivalents) was added and the reaction was stirred for 5 minutes under an atmosphere of nitrogen. A solution of the appropriate halide (1 equivalent) in a solution of 10% DMF/THF was slowly added to the reaction mixture. The mixture was allowed to stir for 10 minutes and then ether was added. The reaction mixture was washed with 1N sodium hydroxide. The organic layer was dried over sodium sulfate, filtered, and evaporated to dryness. The crude product was purified on silica gel to yield the pure product.

Specific Example

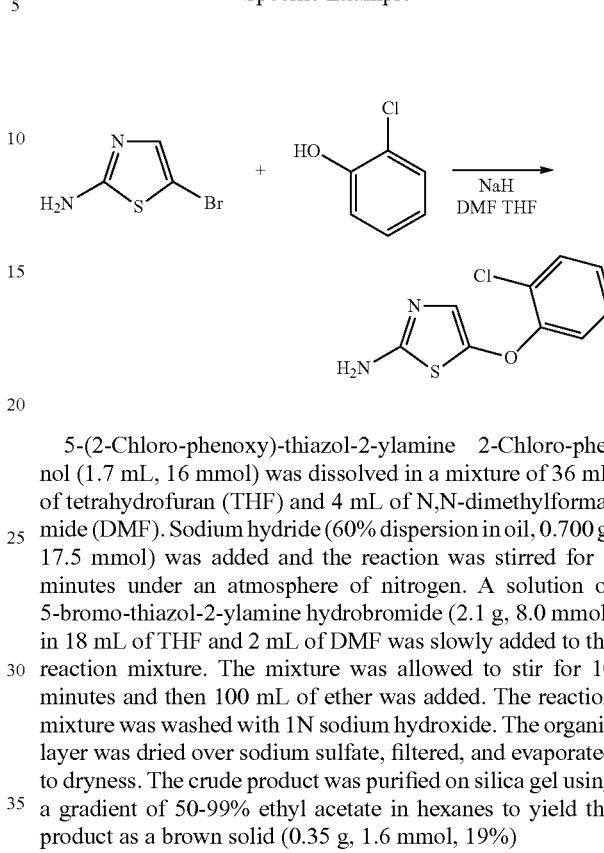

5-(2-Chloro-phenoxy)-thiazol-2-ylamine 2-Chloro-phenol (1.7 mL, 16 mmol) was dissolved in a mixture of 36 mL of tetrahydrofuran (THF) and 4 mL of N,N-dimethylformamide (DMF). Sodium hydride (60% dispersion in oil, 0.700 g, 17.5 mmol) was added and the reaction was stirred for 5 minutes under an atmosphere of nitrogen. A solution of 5-bromo-thiazol-2-ylamine hydrobromide (2.1 g, 8.0 mmol) in 18 mL of THF and 2 mL of DMF was slowly added to the reaction mixture. The mixture was allowed to stir for 10 minutes and then 100 mL of ether was added. The reaction mixture was washed with 1N sodium hydroxide. The organic layer was dried over sodium sulfate, filtered, and evaporated to dryness. The crude product was purified on silica gel using a gradient of 50-99% ethyl acetate in hexanes to yield the product as a brown solid (0.35 g, 1.6 mmol, 19%)

Example 15

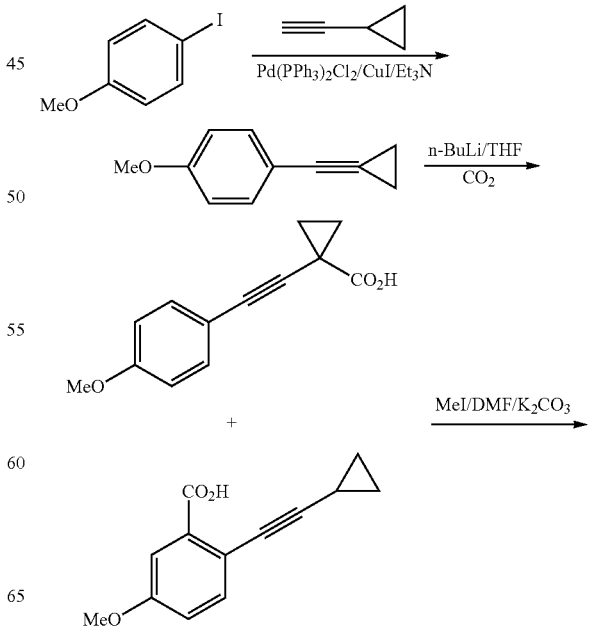

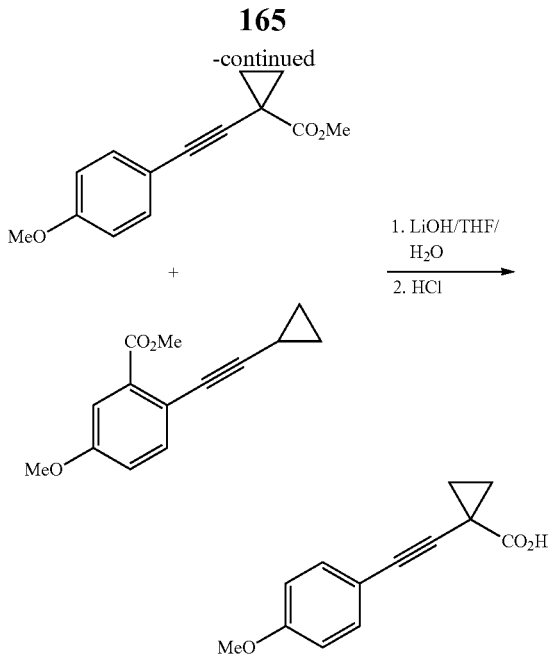

1-Cyclopropylethynyl-4-methoxy-benzene Cyclopropylethyne (15 g, 0.22 mol) was slowly added to a mixture of 4-iodoanisole (30 g, 0.13 mol), copper (I) iodide (1.2 g, 0.0063 mol), and triethylamine (30 g, 0.30 mol) in tetrahydrofuran (THF, 400 mL). After being stirred for 4 hours, the resulting precipitate was filtered and washed with THF. The combined filtrate was evaporated to dryness and the residue was purified by column chromatography to afford 1-cyclopropylethynyl-4-methoxy-benzene as a yellow oil (15 g, 0.087 mol, 67%). NMR (CDCl$_3$) δ 7.31 (d, J=8.8 Hz, 2 H), 6.80 (d, J=8.8 Hz, 2H), 3.79 (s, 3H), 1.43 (m, 1H), 0.85 (m, 2H), 0.78 (m, 2H).

1-(4-Methoxy-phenylethynyl)-cyclopropanecarboxylic acid and 2-cyclopropylethynyl-5-methoxy-benzoic acid To a solution of 1-cyclopropylethynyl-4-methoxy-benzene (7.5 g, 0.043 mol) in THF (250 mL) was added dropwise n-butyl lithium (n-BuLi, 21 mL, 0.052 mol) at −78° C. under nitrogen. After being stirring for 15 minutes, the solution was warmed to room temperature and stirred for another hour. The solution was cooled to −78° C. and gaseous carbon dioxide was introduced to the solution for 1 hour. The mixture was warmed to −20° C. and quenched with water (100 mL). The solution was washed with ether and the separated aqueous layer was acidified to pH 4. The mixture was extracted with ether and the combined organic layer was washed with a saturated aqueous solution of sodium chloride, dried with sodium sulfate, and evaporated to dryness to afford a mixture of 1-(4-methoxy-phenylethynyl)-cyclopropanecarboxylic acid and 2-cyclopropylethynyl-5-methoxy-benzoic acid as a yellow solid (5.0 g, 0.023 mmol).

1-(4-Methoxy-phenylethynyl)-cyclopropanecarboxylic acid methyl ester and 2-cyclopropylethynyl-5-methoxybenzoic acid methyl ester Iodomethane (3.6 g, 0.026 mol) was slowly added to a mixture of 1-(4-methoxy-phenylethynyl)-cyclopropanecarboxylic acid, 2-cyclopropylethynyl-5-methoxy-benzoic acid (5.0 g) and potassium carbonate (4.8 g, 0.034 mol) in DMF (100 mL). After stirring for 4 hours, the mixture was diluted with ether (200 mL) and washed with water. The ether layer was dried over sodium sulfate, evaporated to dryness, and the residue was purified by column chromatography to yield 1-(4-methoxy-phenylethynyl)-cyclopropanecarboxylic acid methyl ester as a yellow oil (2.2 g). $^1$H NMR (CDCl$_3$) δ 7.36 (d, J=8.8 Hz, 2H), 6.81 (d, J=8.8 Hz, 2H), 3.79 (s, 3H), 3.76 (s, 3H), 1.62 (m, 2H), 1.41 (m, 2H). 2-cyclopropylethynyl-5-methoxy-benzoic acid methyl ester (1.0 g). $^1$H NMR (CDCl$_3$) δ 7.89 (d, J=2.4 Hz, 1H), 7.46 (dd, J$_1$=8.4 Hz, J$_2$=2.4 Hz, 1H), 6.8 (d, J=8.4 Hz, 1H), 3.88 (s, 3H), 3.87 (s, 3H), 1.43 (m, 1H), 0.86 (m, 2H), 0.78 (m, 2H).

1-(4-Methoxy-phenylethynyl)-cyclopropanecarboxylic acid A mixture of 1-(4-methoxy-phenylethynyl)-cyclopropanecarboxylic acid methyl ester (2.2 g, 9.4 mmol), lithium hydroxide (0.60 g, 14 mmol) in THF (30 mL), and water (30 mL) was stirred for 6 hours. The solution was washed with ether and the aqueous layer was acidified to pH=4 and then extracted with ether. The organic layer was dried over sodium sulfate, and evaporated to dryness to yield 1-(4-methoxy-phenylethynyl)-cyclopropanecarboxylic acid as a white solid (2.0 g, 0.0092 mmol, 98%). ESI-MS m/z calc. 216.1, found; 217.2 (M+1)$^+$; $^1$H NMR (CDCl$_3$) δ 7.35 (d, J=8.8 Hz, 2H), 6.80 (d, J=8.8 Hz, 2H), 3.79 (s, 3H), 1.69 (m, 2H), 1.47 (m, 2H).

Example 16

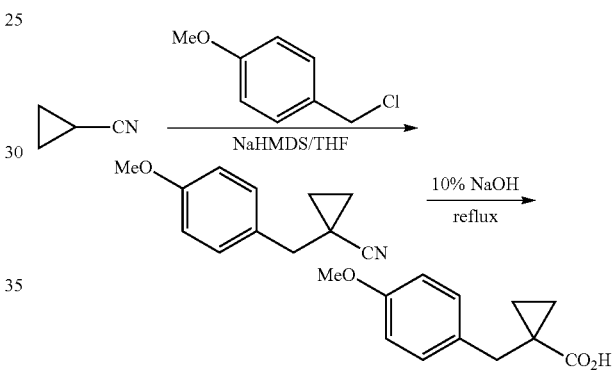

1-(4-Methoxy-benzyl)-cyclopropanecarbonitrile Sodium bis(trimethylsilyl)amide (2 M in tetrahydrofuran, 37.5 mL, 75.0 mmol) was slowly added to a solution of cyclopropanecarbonitrile (3.35 g, 49.9 mmol) in THF (30 mL) at room temperature. The reaction mixture was stirred for 20 minutes and then a solution 1-chloromethyl-4-methoxy-benzene (7.83 g, 50.0 mmol) in THF was added. The mixture was heated at reflux for 3 hours and then quenched with a saturated aqueous solution of ammonium chloride (50 mL). The separated aqueous layer was extracted three times with ethyl acetate (50 mL). The combined organic layers were washed with a saturated aqueous solution of sodium bicarbonate and a saturated aqueous solution of sodium chloride, dried over sodium sulfate, filtered, and evaporated to dryness to give crude 1-(4-methoxy-benzyl)-cyclopropanecarbonitrile, which was used directly in the next step.

1-(4-Methoxy-benzyl)-cyclopropanecarboxylic acid The crude 1-(4-methoxybenzyl)-cyclopropanecarbonitrile was refluxed in sodium hydroxide (10% aqueous solution, 30 mL) overnight. The mixture was diluted with water (30 mL) and then washed with ethyl ether. The aqueous phase was acidified with 2 M hydrochloric acid to pH 5 and extracted three times with ethyl acetate (50 mL). The combined organic layer was washed with a saturated aqueous solution of sodium chloride, dried over sodium sulfate, filtered, and evaporated to dryness to give the pure product (5.6 g, 54% from cyclopropanecarbonitrile). ESI-MS m/z calc. 206.1. found 206.9

(M+1)$^+$; $^1$H NMR (DMSO) δ 12.15 (s, 1H), 7.13 (d, J=8.4, 2H), 6.80 (d, J=8.4, 2H), 3.69 (s, 3H), 2.78 (s, 2H), 1.07-1.04 (m, 2H), 0.76-0.74 (m, 2H).

Example 17

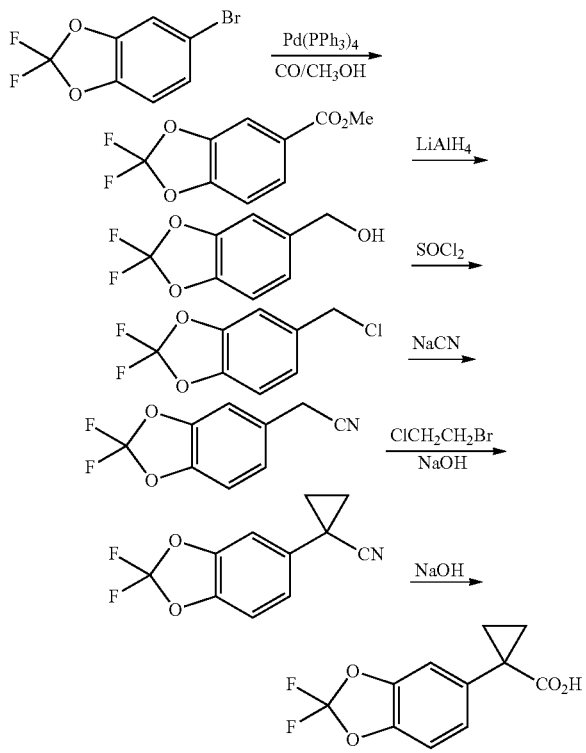

2,2-Difluoro-benzo[1,3]dioxole-5-carboxylic acid methyl ester A solution of 5-bromo-2,2-difluoro-benzo[1,3]dioxole (11.8 g, 50.0 mmol) and tetrakis(triphenylphosphine)palladium (0) [(Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give 2,2-difluoro-benzo[1,3]dioxole-5-carboxylic acid methyl ester (11.5 g), which was used directly in the next step.

(2,2-Difluoro-benzo[1,3]dioxol-5-yl)-methanol 2,2-Difluoro-benzo[1,3]dioxole-5-carboxylic acid methyl ester (11.5 g) dissolved in 20 mL of anhydrous tetrahydrofuran (20 mL) was slowly added to a suspension of lithium aluminum hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 g), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 38 mmol, 76% over two steps) as a colorless oil.

5-Chloromethyl-2,2-difluoro-benzo[1,3]dioxole Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the combined organic layers were dried over sodium sulfate, filtered, and evaporated to dryness to give crude 5-chloromethyl-2,2-difluoro-benzo[1,3]dioxole (4.4 g) which was used directly in the next step.

(2,2-Difluoro-benzo[1,3]dioxol-5-yl)-acetonitrile A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The combined organic layers were dried over sodium sulfate and evaporated to dryness to give crude (2,2-difluoro-benzo[1,3]dioxol-5-yl)-acetonitrile (3.3 g) which was used directly in the next step.

1-(2,2-Difluoro-benzo[1,3]dioxol-5-yl)-cyclopropanecarbonitrile Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C. The mixture was stirred overnight at 70° C. and the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

1-(2,2-Difluoro-benzo[1,3]dioxol-5-yl)-cyclopropanecarboxylic acid The 1-(2,2-difluoro-benzo[1,3]dioxol-5-yl)-cyclopropanecarbonitrile (crude from the last step) was refluxed in 10% aqueous sodium hydroxide (50 mL) for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 0.62 mmol, 2% over four steps). ESI-MS m/z calc. 242.04, found 241.58 (M-1)$^-$; $^1$H NMR (CDCl$_3$) δ 7.14-7.04 (m, 2H), 6.98-6.96 (m, 1H), 1.74-1.64 (m, 2H), 1.26-1.08 (m, 2H).

Example 18

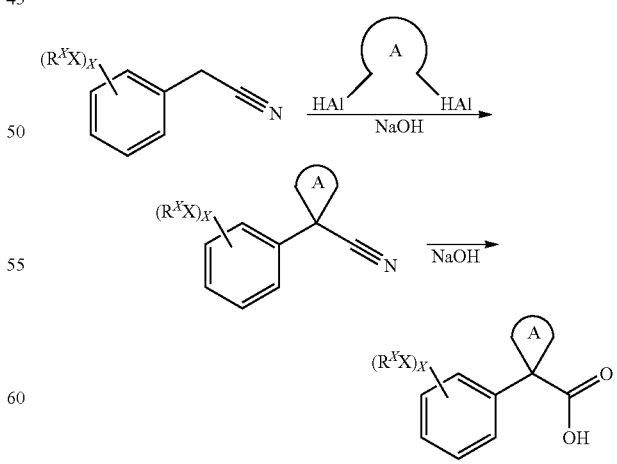

Hal = Cl, Br, I

General procedure: Sodium hydroxide (50% aqueous solution, 7.4 equivalents) was slowly added to a mixture of the appropriate phenyl acetonitrile, benzyltriethylammonium chloride (1.1 equivalents), and the appropriate dihalo compound (2.3 equivalents) at 70° C. The mixture was stirred overnight at 70° C. and the reaction mixture was diluted with water (30 mL) and extracted with ethyl acetate. The combined organic layers were dried over sodium sulfate and evaporated to dryness to give the crude cyclopropanecarbonitrile, which was used directly in the next step.

The crude cyclopropanecarbonitrile was refluxed in 10% aqueous sodium hydroxide (7.4 equivalents) for 2.5 hours. The cooled reaction mixture was washed with ether (100 mL) and the aqueous phase was acidified to pH 2 with 2M hydrochloric acid. The precipitated solid was filtered to give the cyclopropanecarboxylic acid as a white solid.

Specific Example

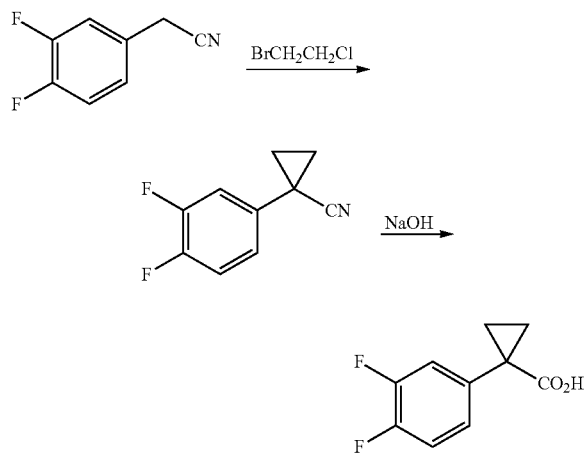

1-(3,4-Difluoro-phenyl)-cyclopropanecarbonitrile A 50% aqueous solution of sodium hydroxide (18 g, 46 mmol) was slowly added to a mixture of (3,4-difluoro-phenyl)-acetonitrile (7.1 g, 46 mmol), benzyltriethylammonium chloride (0.26 g, 1.2 mmol) and 1-bromo-2-chloroethane (15 g, 105 mmol) at 70° C. The mixture was stirred overnight at 70° C. The cooled reaction mixture was diluted with water (50 mL) and extracted three times with ethyl acetate (50 mL). The combined organic layers were washed with a saturated aqueous solution of sodium chloride, dried over sodium sulfate, and evaporated to dryness to give crude 1-(3,4-difluoro-phenyl)-cyclopropanecarbonitrile which was used directly in the next step. NMR (CDCl$_3$) δ 7.18-7.03 (m, 3H), 1.79-1.69 (m, 2H), 1.43-1.38 (m, 2H).

1-(3,4-Difluoro-phenyl)-cyclopropanecarboxylic acid 1-(3,4-Difluoro-phenyl)-cyclopropanecarbonitrile (4.9 g crude from last step) was refluxed in sodium hydroxide (10% aqueous solution, 100 mL) for 2.5 hours. The reaction mixture was washed twice with ethyl ether (100 mL). The aqueous phase was cooled to 0° C. and brought to pH 2 to 3 with concentrated hydrochloric acid. The aqueous layer was then extracted twice with ethyl acetate (100 mL). The combined organic layers were dried with anhydrous sodium sulfate, filtered, and evaporated to dryness to give a white solid (4.0 g, 20 mmol, 44%, two steps). ESI-MS m/z calc. 198.05, found 197.05 (M-H$^+$); $^1$H NMR (CDCl$_3$) δ 10.9 (br s, 1H), 7.16-7.02 (m, 3H), 1.66-1.60 (m, 2H), 1.27-1.21 (m, 2H).

Example 19

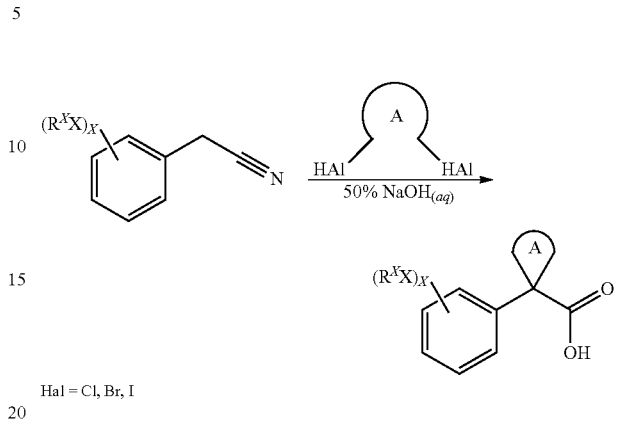

Hal = Cl, Br, I

General procedure: Benzyltriethylammonium chloride (0.025 equivalents) and the appropriate dihalo compound (2.5 equivalents) were added to a substituted phenyl acetonitrile. The mixture was heated at 70° C. and then 50% sodium hydroxide (10 equivalents) was added dropwise. The reaction was stirred at 70° C. for 12-24 hours to insure complete formation of the cycloalkyl moity and then heated at 150° C. for 24-48 hours to insure complete conversion from the nitrile to the carboxylic acid. The dark brown/black reaction mixture was diluted with water and washed with dichloromethane three times to remove side products. The basic aqueous solution was acidified with concentrated hydrochloric acid to pH less than one and the precipitate which began to form at pH 4 was filtered and washed with 1M hydrochloric acid two times. The solid material was dissolved in dichloromethane and washed two times with 1M hydrochloric acid and one time with a saturated aqueous solution of sodium chloride. The organic solution was dried over sodium sulfate and evaporated to dryness to give the cycloalkylcarboxylic acid a white solid. Yields and purities were typically greater than 90%.

Specific Example

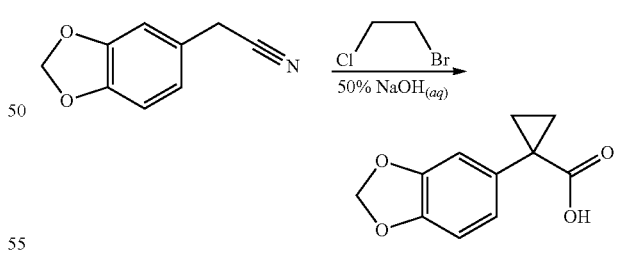

1-Benzo[1,3]dioxol-5-yl-cyclopropanecarboxylic acid A mixture of benzo[1,3]dioxole-5-carbonitrile (5.10 g, 31.7 mmol), 1-bromo-2-chloro-ethane (9.000 mL 108.6 mmol), and benzyltriethylammonium chloride (0.181 g 0.795 mmol) was heated at 70° C. and then 50% (wt./wt.) aqueous sodium hydroxide (26 mL) was slowly added. The reaction was stirred at 70° C. for 16 hours and then heated at 130° C. for 48 hours. The dark brown/black reaction mixture was diluted with water (400 mL) and washed twice with equal volumes ethyl acetate and dichloromethane. The basic aqueous solution was acidified with concentrated hydrochloric acid to pH less than one and the precipitate was filtered and washed with 1 M hydrochloric acid. The solid material was dissolved in dichloromethane (400 mL) and washed twice with equal volumes of 1 M hydrochloric acid and once with a saturated aqueous solution of sodium chloride. The organic solution was dried over sodium sulfate and evaporated to dryness to give a white to slightly off-white solid (5.23 g, 25.4 mmol, 80%. ESI-MS m/z calc. 206.06. found 207.1 (M+1)$^+$. Retention time of 2.37 minutes. $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H).

Example 20

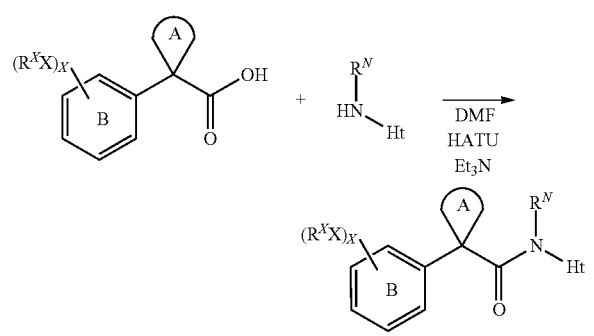

General Procedure: One equivalent of the appropriate carboxylic acid and one equivalent of the appropriate amine were dissolved in N,N-dimethylformamide (DMF) containing triethylamine (3 equivalents). O-(7-Azabenzotriazol-1-yl)-N,N,N',N'-tetramethyluronium hexafluorophosphate (HATU) was added and the solution was allowed to stir. The crude product was purified by reverse-phase preparative liquid chromatography to yield the pure product.

Specific Examples

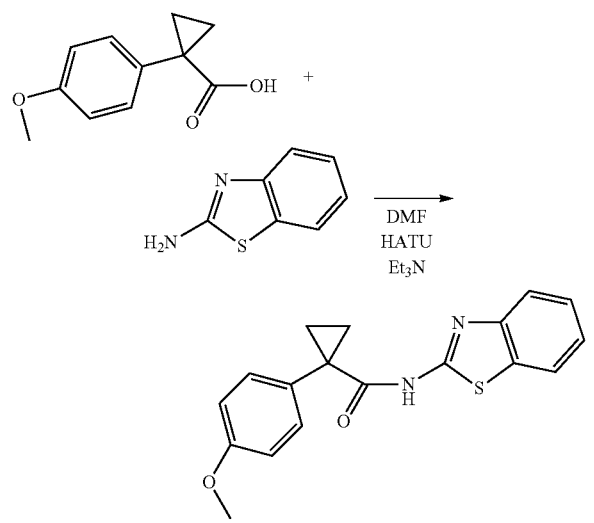

1-(4-Methoxy-phenyl)-cyclopropanecarboxylic acid benzothiazol-2-ylamide Benzothiazol-2-ylamine (30 mg, 0.20 mmol) and 1-(4-methoxy-phenyl)-cyclopropanecarboxylic acid (38 mg, 0.20 mmol) were dissolved in N,N-dimethylformamide (1 mL) containing triethylamine (84 μL, 0.60 mmol). O-(7-Azabenzotriazol-1-yl)-N,N,N',N'-tetramethyluronium hexafluorophosphate (HATU, 80 mg, 0.21 mmol) was added and the solution was allowed to stir at room temperature for 16 hours. The crude product was purified by reverse-phase preparative liquid chromatography to yield the pure product (17 mg, 0.052 mmol, 26%). ESI-MS m/z calc. 324.1. found 325.0 (M+1)$^+$. Retention time of 3.48 minutes.

Example 21

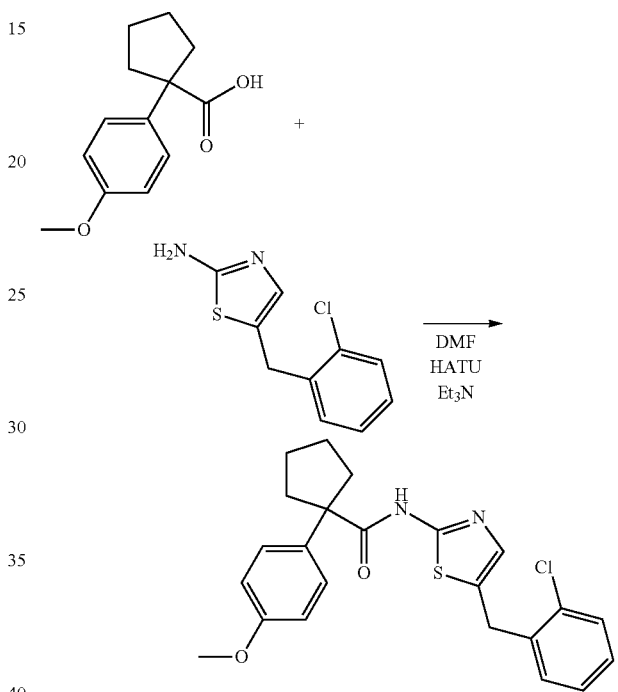

1-(4-Methoxy-phenyl)-cyclopentanecarboxylic acid [5-(2-chloro-benzyl)-thiazol-2-yl]-amide 5-(2-Chloro-benzyl)-thiazol-2-ylamine (45 mg, 0.20 mmol) and 1-(4-methoxy-phenyl)-cyclopentanecarboxylic acid (44 mg, 0.20 mmol) were dissolved in N,N-dimethylformamide (2 mL) containing triethylamine (84.1 μL, 0.600 mmol). O-(7-Azabenzotriazol-1-yl)-N,N,N',N'-tetramethyluronium hexafluorophosphate (HATU, 84 mg, 0.22 mmol) was added and the solution was allowed to stir for 16 hours. The crude product was purified by reverse-phase preparative liquid chromatography. ESI-MS m/z calc. 426.1, found; 427.2 (M+1)$^+$; Retention time 3.97 minutes. $^1$H NMR (400 MHz, MeOD) δ 1.62-1.84 (m, 4H), 1.95-2.17 (m, 2H), 2.41-2.62 (m, 2H), 3.78 (s, 3H), 4.22 (s, 2H), 6.90 (d, J=8.8 Hz, 2H), 7.03-7.49 (m, 7H).

Example 22

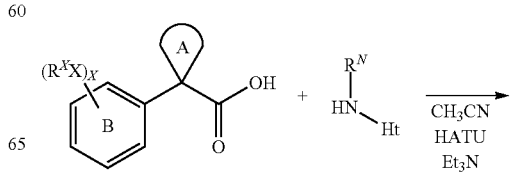

(m, 5H), 1.50-1.68 (m, 4H), 2.91 (t, J=7.5 Hz, 2H), 4.28 (q, J=7.1 Hz, 2H), 6.00 (s, 2H), 6.81 (d, J=7.7 Hz, 1H), 6.95-6.98 (m, 2H), 9.22 (s, 1H).

Example 23

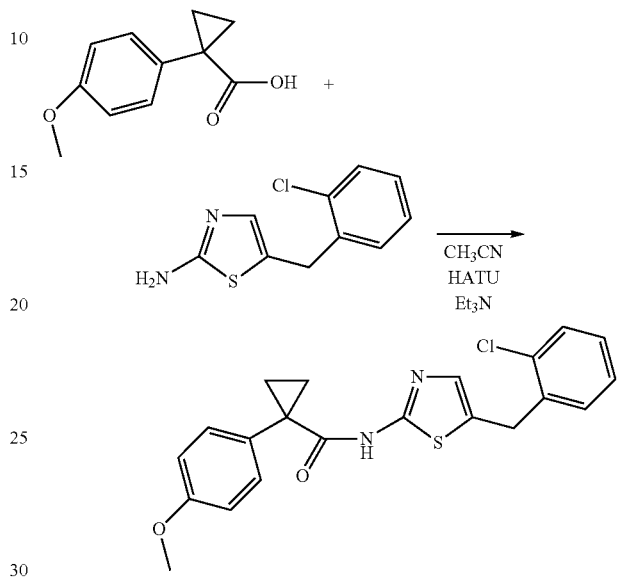

1-(4-Methoxy-phenyl)-cyclopropanecarboxylic acid [5-(2-chloro-benzyl)-thiazol-2-yl]-amide 5-(2-Chloro-benzyl)-thiazol-2-ylamine (0.250 g, 1.11 mmol) and 1-(4-methoxy-phenyl)-cyclopropanecarboxylic acid (0.213 g, 1.11 mmol) were dissolved in acetonitrile (20 mL) containing triethylamine (0.28 mL, 2.0 mmol). O-(7-Azabenzotriazol-1-yl)-N,N,N',N'-tetramethyluronium hexafluorophosphate (HATU, 0.494 g, 1.3 mmol) was added and the solution was allowed to stir for 16 hours. The crude product was evaporated to dryness and purified by column chromatography on silica gel using a gradient of 5-40% ethyl acetate in hexanes. The pure fractions were combined and evaporated to dryness to yield a white solid (0.24 g, 0.60 mmol, 54%). ESI-MS m/z calc. 398.1, found 399.0 (M+1)$^+$. Retention time of 3.77 minutes. $^1$H NMR (400 MHz, CD$_3$CN) δ 1.21 (q, J=3.6 Hz, 2H), 1.59 (q, J=3.6 Hz, 2H), 3.78 (s, 3H), 4.19 (s, 2H), 6.88-6.96 (m, 2H), 7.07 (s, 1H), 7.23-7.46 (m, 6H).

Example 24

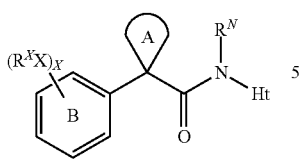

General Procedure: One equivalent of the appropriate carboxylic acid and one equivalent of the appropriate amine were dissolved in acetonitrile containing triethylamine (3 equivalents). O-(7-Azabenzotriazol-1-yl)-N,N,N',N'-tetramethyluronium hexafluorophosphate (HATU) was added and the solution was allowed to stir. The crude product was purified by reverse-phase preparative liquid chromatography to yield the pure product.

Specific Examples

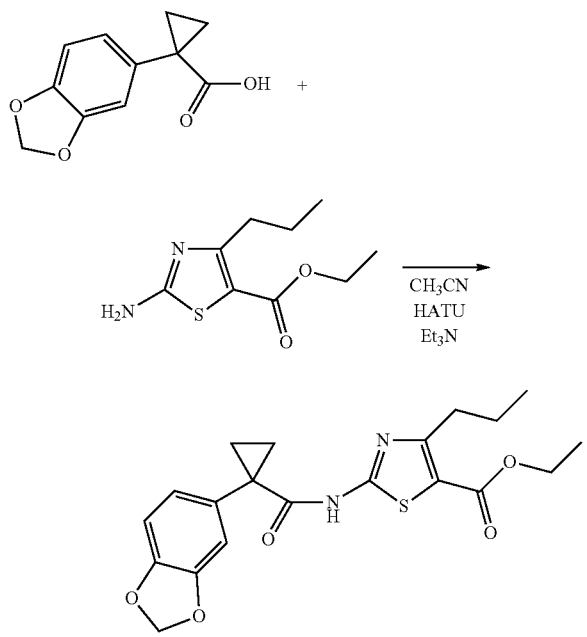

2-[(1-Benzo[1,3]dioxol-5-yl-cyclopropanecarbonyl)-amino]-4-propyl-thiazole-5-carboxylic acid ethyl ester 2-Amino-4-propyl-thiazole-5-carboxylic acid ethyl ester (0.50 g, 2.3 mmol) and 1-benzo[1,3]dioxol-5-yl-cyclopropanecarboxylic acid (0.48 g, 2.3 mmol) were dissolved in acetonitrile (15 mL) containing triethylamine (0.66 mL, 4.7 mmol). O-(7-Azabenzotriazol-1-yl)-N,N,N',N'-tetramethyluronium hexafluorophosphate (HATU, 0.89 g, 2.3 mmol) was added and the solution was allowed to stir at 65° C. for four hours. The crude product was evaporated to dryness and purified by column chromatography on silica gel using a gradient of 10-99% ethyl acetate in hexanes. The pure fractions were combined and evaporated to dryness to yield a white solid (0.58 g, 1.4 mmol, 61%). ESI-MS m/z calc. 402.1. found 403.3 (M+1)$^+$. Retention time of 3.78 minutes. $^1$H NMR (400 MHz, CD$_3$CN) δ 0.84 (t, J=7.4 Hz, 3H), 1.25-1.35

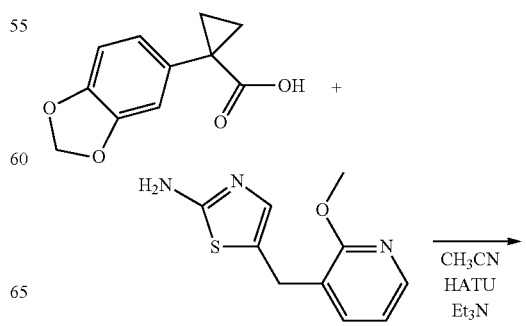

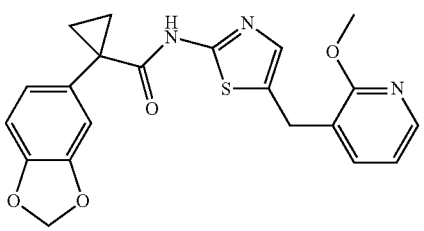

1-Benzo[1,3]dioxol-5-yl-cyclopropanecarboxylic acid [5-(2-methoxy-pyridin-3-ylmethyl)-thiazol-2-yl]-amide 5-(2-Methoxy-pyridin-3-ylmethyl)-thiazol-2-ylamine (221 mg, 1.00 mmol) and 1-benzo[1,3]dioxol-5-yl-cyclopropanecarboxylic acid (206 g, 1.00 mmol) were dissolved in acetonitrile (5 mL) containing triethylamine (0.421 mL, 3.00 mmol). O-(7-Azabenzotriazol-1-yl)-N,N,N',N'-tetramethyluronium hexafluorophosphate (HATU, 760 mg, 2.0 mmol) was added and the solution was allowed to stir at 78° C. for 12 hours. An aliquot of the crude product was purified by reverse-phase preparative liquid chromatography. ESI-MS m/z calc. 409.1, found; 410.3 (M+1)$^+$. Retention time 3.23 minutes.

Example 25

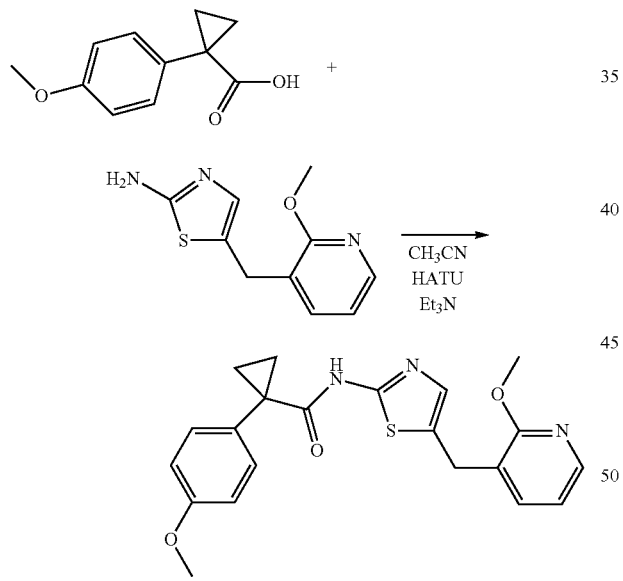

1-(3-Methoxy-phenyl)-cyclopropanecarboxylic acid [5-(2-methoxy-pyridin-3-ylmethyl)-thiazol-2-yl]-amide 5-(2-Methoxy-pyridin-3-ylmethyl)-thiazol-2-ylamine (221 mg, 1.00 mmol) and 1-(4-methoxy-phenyl)-cyclopropanecarboxylic acid (192 g, 1.00 mmol) were dissolved in acetonitrile (5 mL) containing triethylamine (0.421 mL, 3.00 mmol). O-(7-Azabenzotriazol-1-yl)-N,N,N',N'-tetramethyluronium hexafluorophosphate (HATU, 760 mg, 2.0 mmol) was added and the solution was allowed to stir at 78° C. for 12 hours. An aliquot of the crude product was purified by reverse-phase preparative liquid chromatography. ESI-MS m/z calc. 395.1. found 396.3 (M+1)$^+$. Retention time 3.27 minutes.

Example 26

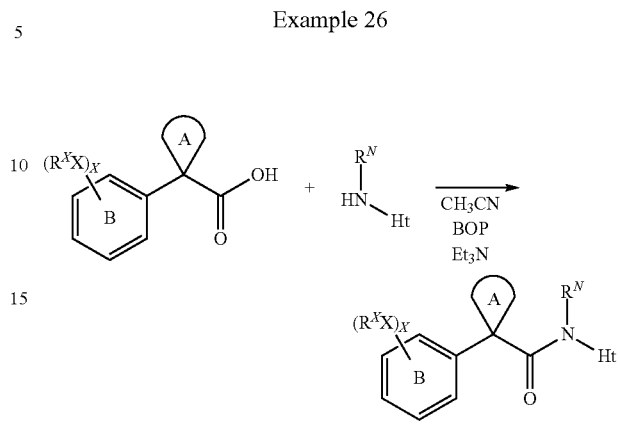

General Procedure: One equivalent of the appropriate carboxylic acid and one equivalent of the appropriate amine were dissolved in acetonitrile containing triethylamine (3 equivalents). Benzotriazol-1-yloxytris(dimethylamino)phosphonium hexafluorophosphate (BOP) was added and the solution was allowed to stir. The crude product was purified by reverse-phase preparative liquid chromatography to yield the pure product.

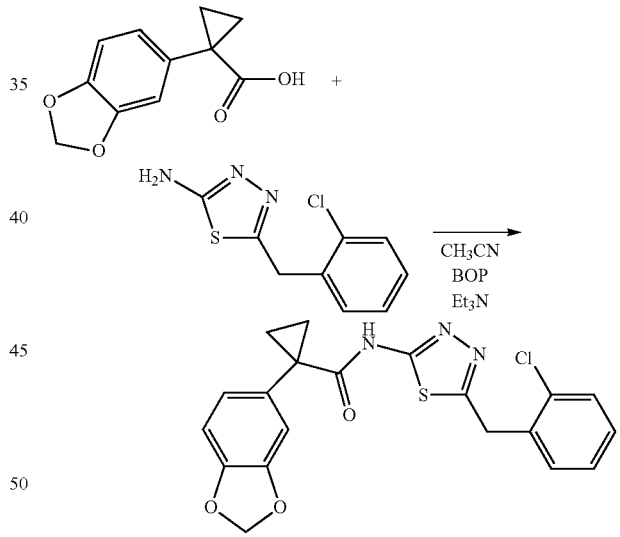

1-Benzo[1,3]dioxol-5-yl-cyclopropanecarboxylic acid [5-(2-chloro-benzyl)-[1,3,4]thiadiazol-2-yl]-amide 5-(2-Chloro-benzyl)-[1,3,4]thiadiazol-2-ylamine (23 mg, 0.10 mmol) and 1-benzo[1,3]dioxol-5-yl-cyclopropanecarboxylic acid (21 mg, 0.10 mmol) were dissolved in acetonitrile (1.5 mL) containing triethylamine (42 µL, 0.30 mmol). Benzotriazol-1-yloxytris(dimethylamino)phosphonium hexafluorophosphate (BOP, 49 mg, 0.11 mmol) was added and the solution was allowed to stir for 16 hours. The crude product was purified by reverse-phase preparative liquid chromatography to yield the pure product (5.7 mg, 0.014 mmol, 14%). ESI-MS m/z calc. 413.1. found 414.3 (M+1)$^+$. Retention time 3.38 minutes.

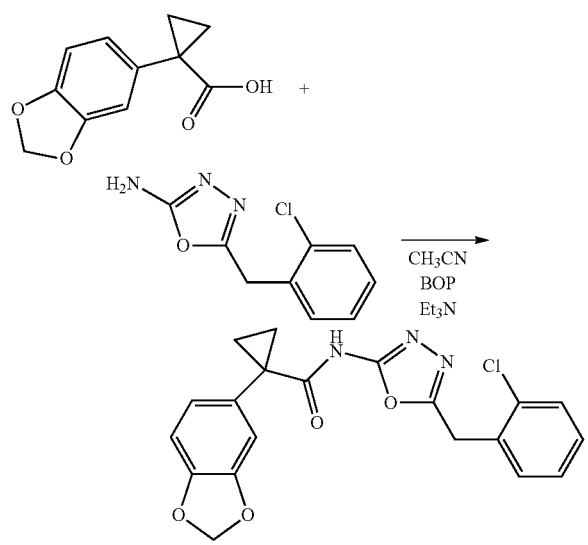

1-Benzo[1,3]dioxol-5-yl-cyclopropanecarboxylic acid [5-(2-chloro-benzyl)-[1,3,4]oxadiazol-2-yl]-amide 5-(2-Chloro-benzyl)-[1,3,4]oxadiazol-2-ylamine (21 mg, 0.10 mmol) and 1-benzo[1,3]dioxol-5-yl-cyclopropanecarboxylic acid (21 mg, 0.10 mmol) were dissolved in acetonitrile (1.5 mL) containing triethylamine (42 μL, 0.30 mmol). Benzotriazol-1-yloxytris(dimethylamino)phosphonium hexafluorophosphate (BOP, 49 mg, 0.11 mmol) was added and the solution was allowed to stir for 16 hours. The crude product was purified by reverse-phase preparative liquid chromatography to yield the pure product (6.0 mg, 0.015 mmol, 15%). ESI-MS m/z calc. 397.1. found 398.3 (M+1)$^+$. Retention time 2.96 minutes.

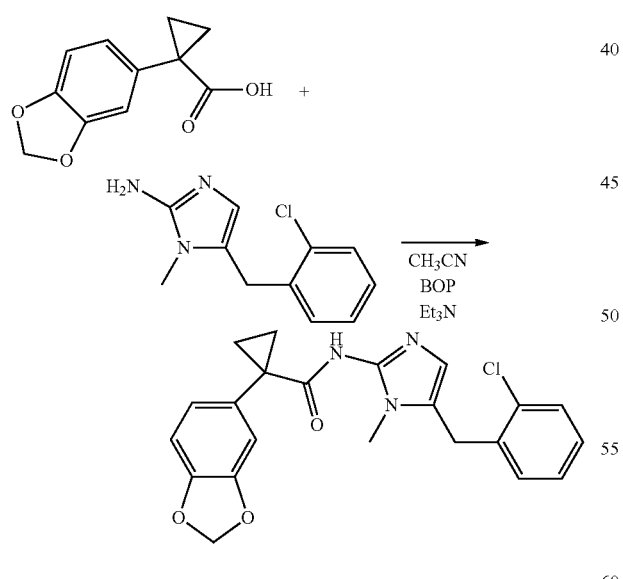

1-Benzo[1,3]dioxol-5-yl-cyclopropanecarboxylic acid [5-(2-chloro-benzyl)-1-methyl-1H-imidazol-2-yl]-amide 5-(2-Chloro-benzyl)-1-methyl-1H-imidazol-2-ylamine (21 mg, 0.10 mmol) and 1-benzo[1,3]dioxol-5-yl-cyclopropanecarboxylic acid (22 mg, 0.10 mmol) were dissolved in acetonitrile (1.5 mL) containing triethylamine (42 μL, 0.30 mmol). Benzotriazol-1-yloxytris(dimethylamino)phosphonium hexafluorophosphate (BOP, 49 mg, 0.11 mmol) was added and the solution was allowed to stir for 16 hours. The crude product was purified by reverse-phase preparative liquid chromatography to yield the pure product as a trifluoroacetic acid salt (11 mg, 0.022 mmol, 22%). ESI-MS m/z calc. 409.1. found 410.1 (M+1)$^+$. Retention time 2.40 minutes.

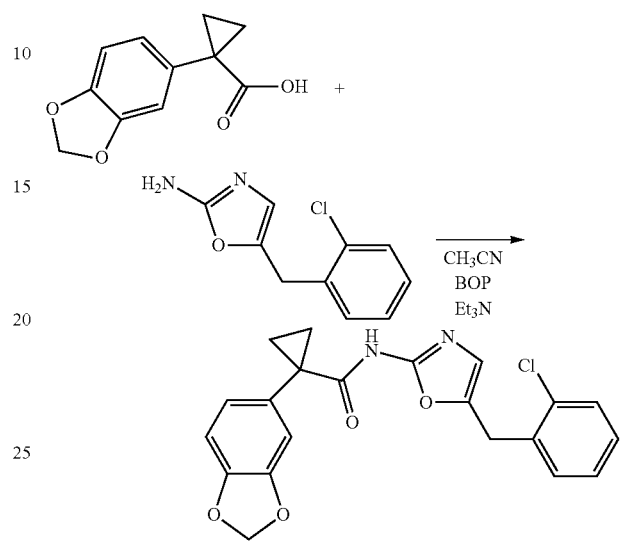

1-Benzo[1,3]dioxol-5-yl-cyclopropanecarboxylic acid [5-(2-chloro-benzyl)-oxazol-2-yl]-amide 5-(2-Chloro-benzyl)-oxazol-2-ylamine (21 mg, 0.10 mmol) and 1-benzo[1,3]dioxol-5-yl-cyclopropanecarboxylic acid (22 mg, 0.10 mmol) were dissolved in acetonitrile (1.5 mL) containing triethylamine (42 μL, 0.30 mmol). Benzotriazol-1-yloxytris(dimethylamino)phosphonium hexafluorophosphate (BOP, 49 mg, 0.11 mmol) was added and the solution was allowed to stir for 16 hours. The crude product was purified by reverse-phase preparative liquid chromatography to yield the pure product (15 mg, 0.037 mmol, 37%). ESI-MS m/z calc. 396.1. found 396.6 (M+1)$^+$. Retention time 3.17 minutes.

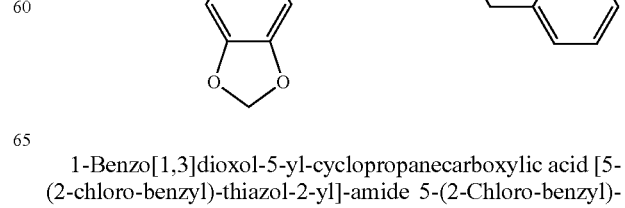

1-Benzo[1,3]dioxol-5-yl-cyclopropanecarboxylic acid [5-(2-chloro-benzyl)-thiazol-2-yl]-amide 5-(2-Chloro-benzyl)- thiazol-2-ylamine (22 mg, 0.10 mmol) and 1-benzo[1,3]dioxol-5-yl-cyclopropanecarboxylic acid (22 mg, 0.10 mmol) were dissolved in acetonitrile (1.5 mL) containing triethylamine (42 µL, 0.30 mmol). Benzotriazol-1-yloxytris(dimethylamino)phosphonium hexafluorophosphate (BOP, 49 mg, 0.11 mmol) was added and the solution was allowed to stir for 16 hours. The crude product was purified by reverse-phase preparative liquid chromatography to yield the pure product (4.1 mg, 0.0098 mmol, 9.8%). ESI-MS m/z calc. 412.1. found 413.3 (M+1)$^+$. Retention time 3.12 minutes.

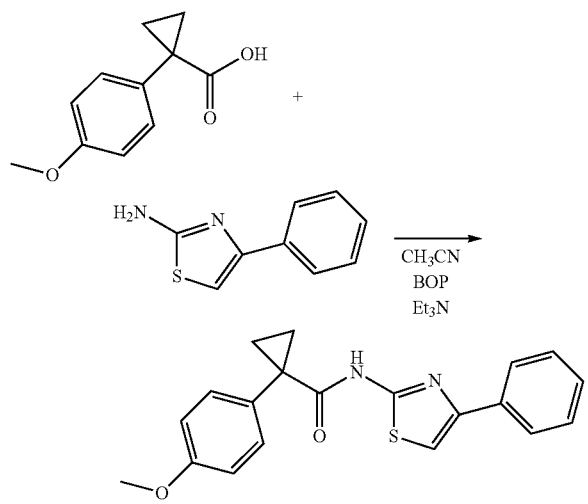

1-(4-Methoxy-phenyl)-cyclopropanecarboxylic acid (4-phenyl-thiazol-2-yl)-amide 1-(4-Methoxy-phenyl)-cyclopropanecarboxylic acid (2.18 g, 11.4 mmol) and 4-phenyl-thiazol-2-ylamine (2.00 g, 11.4 mmol) were dissolved in acetonitrile (50 mL) containing triethylamine (3.17 mL, 22.8 mmol). Benzotriazol-1-yloxy tris(dimethylamino)-phosphonium hexafluorophosphate (BOP, 4.95 g, 11.4 mmol) was added and the solution was allowed to stir for 64 hours. The reaction mixture was evaporated to dryness and purified by column chromatography on silica gel using a gradient of 5-20% ethyl acetate in hexanes. The pure fractions were combined and evaporated to dryness to yield a white solid (1.9 g, 5.43 mmol, 47.5%). ESI-MS m/z calc. 350.1. found 351.1 (M+1)$^+$. Retention time of 3.68 minutes. $^1$H NMR (400 MHz, CD$_3$CN) δ 1.27 (q, J=3.6 Hz, 2H), 1.66 (q, J=3.6 Hz, 2H), 3.87 (s, 3H), 7.04 (m, 2H), 7.40 (m, 6H), 7.82 (m, 2H), 8.79 (s, 1H).

Example 27

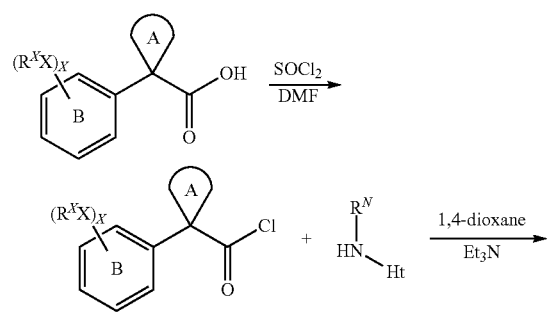

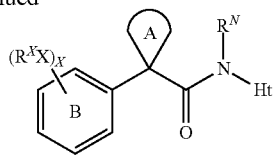

General Procedure: One equivalent of the appropriate carboxylic acid was placed in an oven-dried flask under nitrogen. A minimum of thionyl chloride and a catalytic amount of and N,N-dimethylformamide was added and the solution was allowed to stir for 30 minutes at room temperature. The excess thionyl chloride was removed under vacuum and the resulting solid was suspended in a minimum of anhydrous 1,4-dioxane. This solution was slowly added to a stirred solution of one equivalent the appropriate aminoheterocycle dissolved in a minimum of anhydrous 1,4-dioxane containing three equivalents of triethylamine. The resulting mixture was allowed to stir at room temperature for several hours. The mixture was filtered, evaporated to dryness, and then purified by column chromatography.

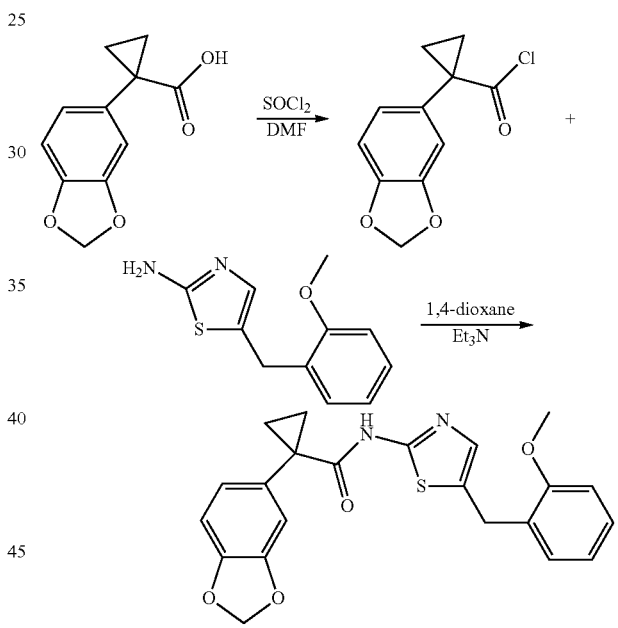

1-Benzo[1,3]dioxol-5-yl-cyclopropanecarboxylic acid [5-(2-methoxy-benzyl)-thiazol-2-yl]-amide 1-Benzo[1,3]dioxol-5-yl-cyclopropanecarboxylic acid (1.87 g, 9.08 mmol) was dissolved in thionyl chloride (5 mL) under nitrogen for 30 minutes. A catalytic amount of N,N-dimethylformamide was added and stirring was continued for an additional 30 minutes. The excess thionyl chloride was evaporated and the resulting residue was dissolved in 1,4 dioxane (15 mL). This solution was slowly added under nitrogen to 5-(2-methoxy-benzyl)-thiazol-2-ylamine (2.00 g, 9.08 mmol) dissolved in 1,4 dioxane (20 mL) containing triethylamine (3.5 mL, 25 mmol). The solution was allowed to stir for 2 hours. The reaction mixture was filtered, the precipitate was washed three times with 1,4 dioxane (20 mL), and the combined filtrate was evaporated to dryness and purified by column chromatography on silica gel using a gradient of 0-30% ethyl acetate in hexanes. The pure fractions were combined and evaporated to dryness to yield an off-white solid. The product was recrystallized twice from ethyl acetate/hexanes to yield the pure product (2.01 g, 4.92 mmol, 54.2%). ESI-MS m/z calc. 408.11. found 409.3 (M+1)⁺. Retention time of 3.48 minutes. ¹H NMR (400 MHz, DMSO-$d_6$) δ 1.11 (m, 2H), 1.43 (m, 2H), 3.80 (s, 3H), 3.97 (s, 2H), 6.01 (s, 2H), 6.87 (m, 3H), 6.98 (m, 2H), 7.16 (m, 2H), 7.22 (m, 1H), 10.76 (s, 1H).

Example 28

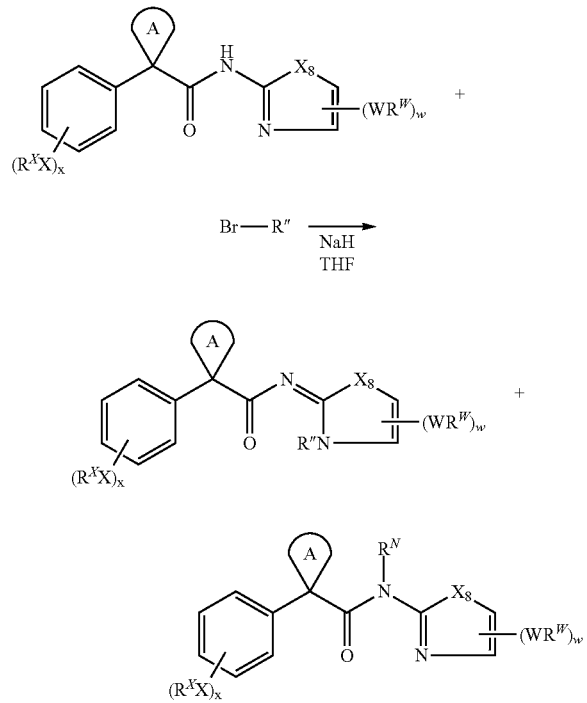

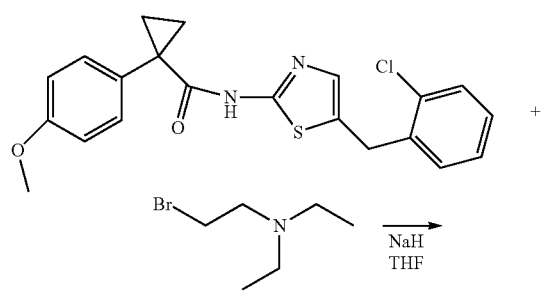

General Procedure: One equivalent of the appropriate halide is mixed with one equivalent of the appropriate nitrogen containing heterocyclic amide with one equivalent of sodium hydride in anhydrous tetrahydrofuran (THF). The reaction mixture was then subjected to microwave irradiation for 10 minutes at 100° C. The solvent was evaporated to dryness and the crude mixture was purified by reverse-phase preparative liquid chromatography to yield the pure product.

Specific Example

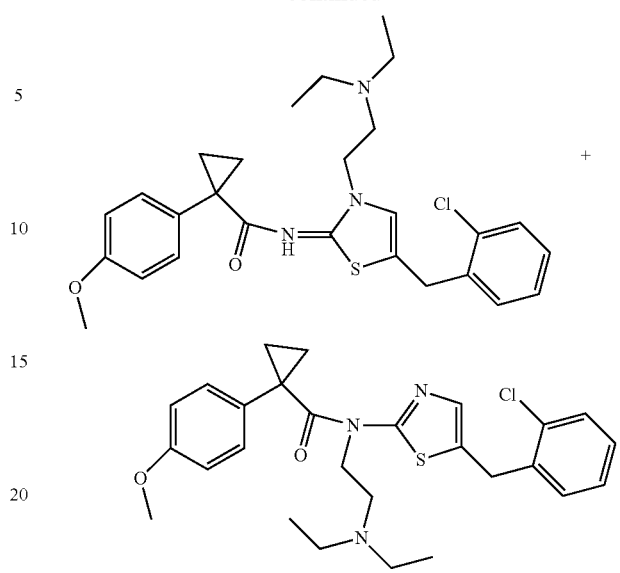

1-(4-Methoxy-phenyl)-cyclopropanecarboxylic acid [5-(2-chloro-benzyl)-3-(2-diethylamino-ethyl)-3H-thiazol-2-ylidene]-amide and 1-(4-methoxy-phenyl)-cyclopropanecarboxylic acid [5-(2-chloro-benzyl)-thiazol-2-yl]-(2-diethylamino-ethyl)-amide 1-(4-Methoxy-phenyl)-cyclopropanecarboxylic acid [5-(2-chloro-benzyl)-thiazol-2-yl]-amide (39.9 mg, 0.100 mmol) and (2-bromo-ethyl)-diethyl-amine hydrobromide (26.1 mg, 0.100 mmol) were dissolved in 1 mL of tetrahydrofuran. Sodium hydride (60% dispersion in oil, 8.8 mg, 0.22 mmol) was added and the reaction was subjected to microwave irradiation for 10 minutes at 100° C. The solvent was evaporated to dryness and the crude mixture was purified by reverse-phase preparative liquid chromatography to yield 1-(4-methoxy-phenyl)-cyclopropanecarboxylic acid [5-(2-chloro-benzyl)-3-(2-diethylamino-ethyl)-3H-thiazol-2-ylidene]-amide (10 mg, 0.020 mmol, 20%) ESI-MS m/z calc. 497.2. found 498.3 (M+1)⁺. Retention time of 2.64 minutes. ¹H NMR (400 MHz, CD₃CN) δ 1.07-1.17 (m, 8H), 1.54-1.59 (m, 2H), 2.88-2.94 (m, 4H), 3.19-3.24 (m, 2H), 3.80 (s, 3H), 4.07 (s, 2H), 4.24 (t, J=6.4 Hz, 2H), 6.86-6.91 (m, 2H), 6.97 (s, 1H), 7.26-7.47 (m, 6H) and 1-(4-methoxy-phenyl)-cyclopropanecarboxylic acid [5-(2-chloro-benzyl)-thiazol-2-yl]-(2-diethylamino-ethyl)-amide (14 mg, 0.028 mmol, 28%) ESI-MS m/z calc. 497.2. found 498.3 (M+1)⁺. Retention time of 2.65 minutes. ¹H NMR (400 MHz, CD₃CN) δ 1.08-1.17 (m, 6H), 1.30-1.37 (m, 2H), 1.51-1.57 (m, 2H), 2.55-2.59 (m, 2H), 3.00-3.05 (m, 4H), 3.79 (s, 3H), 4.26 (s, 2H), 4.42 (t, J=3.0 Hz, 2H), 6.90-6.95 (m, 2H), 7.16-7.23 (m, 2H), 7.27-7.50 (m, 5H).

Example 29

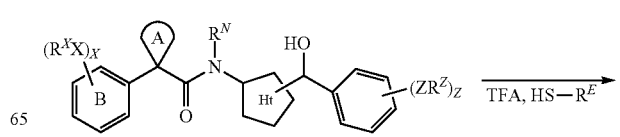

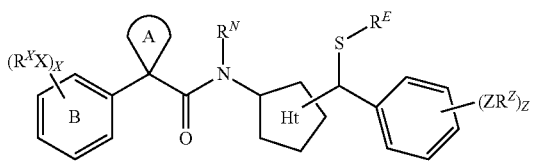

General Procedure: The appropriate alcohol (one equivalent) was placed in a minimum of trifluoroacetic acid. One equivalent of the appropriate thiol was added and the reaction was allowed to stir for 16 hours. The mixture was then evaporated to dryness and purified by reverse-phase preparative liquid chromatography to yield the pure product.

Specific Example

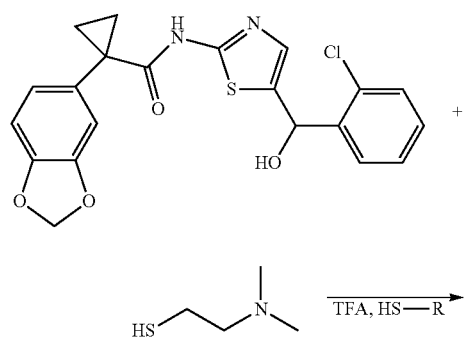

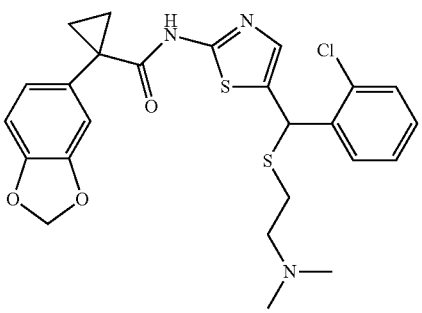

1-Benzo[1,3]dioxol-5-yl-cyclopropanecarboxylic acid {5-[(2-chloro-phenyl)-(2-dimethylamino-ethylsulfanyl)-methyl]-thiazol-2-yl}-amide 1-Benzo[1,3]dioxol-5-yl-cyclopropanecarboxylic acid [5-[(2-chloro-phenyl)-hydroxy-methyl]-thiazol-2-yl]-amide (42 mg, 0.10 mmol) was placed in 1 mL of trifluoroacetic acid. 2-Dimethylamino-ethanethiol hydrochloride (14 mg, 0.10 mmol) was added and the solution was allowed to stir for 16 hours at room temperature. The mixture was then evaporated to dryness and purified by reverse-phase preparative liquid chromatography to yield the pure product as the trifluoroacetic acid salt (35 mg, 0.056 mol, 56%). ESI-MS m/z calc. 515.1. found 516.3 (M+1)$^+$. Retention time 2.81 minutes. $^1$H NMR (400 MHz, CD$_3$CN) δ 1.21-1.25 (m, 2H), 1.57-1.61 (m, 2H), 2.74 (s, 6H), 2.86 (t, J=7.9 Hz, 2H), 3.15-3.31 (m, 2H), 5.90 (s, 1H), 5.97 (s, 2H), 6.79 (d, J=7.9 Hz, 1H), 6.93-6.97 (m, 2H), 7.24 (s, 1H), 7.34 (t, J=6.8 Hz, 1H), 7.41 (t, J=6.9 Hz, 1H), 7.46 (d, J=1.3 Hz, 1H), 7.73 (d, J=7.7 Hz, 1H).

Example 30

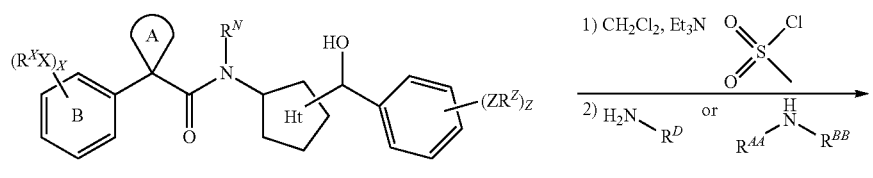

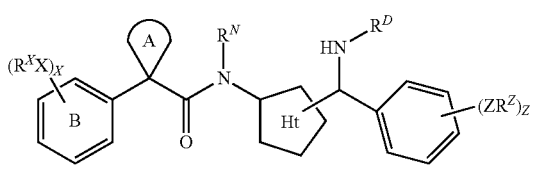

or

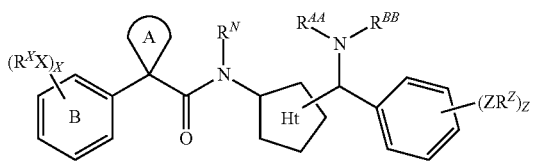

General Procedure: The appropriate alcohol (one equivalent) was placed in a minimum of anhydrous dichloromethane containing triethylamine (2 equivalents). Methanesulfonyl chloride (one equivalent) was added and the solution was stirred at room temperature for 1 hour. The appropriate amine (5 equivalents) was added and the solution was allowed to stir for 16 hours at room temperature. The solution was then evaporated to dryness and purified by reverse-phase preparative liquid chromatography to yield the pure product.

Specific Example

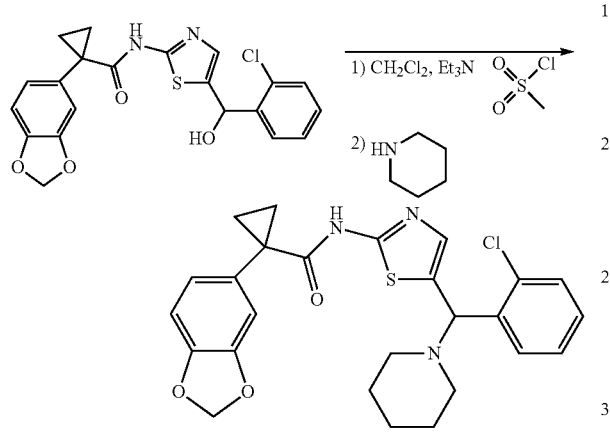

1-Benzo[1,3]dioxol-5-yl-cyclopropanecarboxylic acid {5-[(2-chloro-phenyl)-piperidin-1-yl-methyl]-thiazol-2-yl}-amide 1-Benzo[1,3]dioxol-5-yl-cyclopropanecarboxylic acid [5-[(2-chloro-phenyl)-hydroxy-methyl]-thiazol-2-yl]-amide (43 mg, 0.10 mmol) was placed in 1 mL of anhydrous dichloromethane containing triethylamine (28 µL, 0.20 mmol). Methanesulfonyl chloride (11 mg, 0.10 mmol) was added and the solution was stirred at room temperature for 1 hour. Piperidine (43 mg, 0.50 mmol) was added and the solution was allowed to stir for 16 hours at room temperature. The solution was then evaporated to dryness and purified by reverse-phase preparative liquid chromatography to yield the pure product as the trifluoracetic acid salt (11 mg, 0.018 mol, 18%). ESI-MS m/z calc. 495.1. found 496.3 (M+1)⁺. Retention time 2.52 minutes.

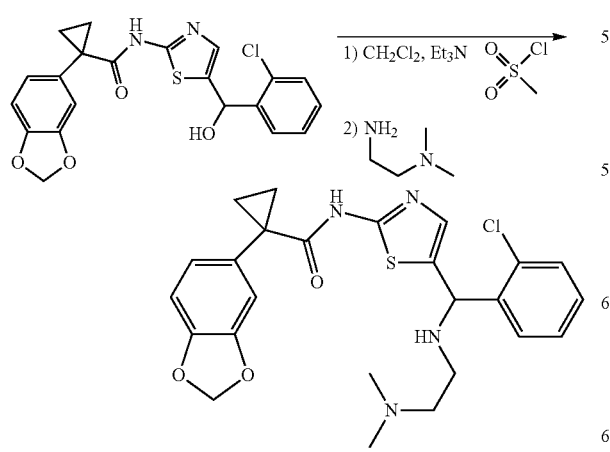

1-Benzo[1,3]dioxol-5-yl-cyclopropanecarboxylic acid {5-[(2-chloro-phenyl)-(2-dimethylamino-ethylamino)-methyl]-thiazol-2-yl}-amide 1-Benzo[1,3]dioxol-5-yl-cyclopropanecarboxylic acid [5-[(2-chloro-phenyl)-hydroxy-methyl]thiazol-2-yl]-amide (43 mg, 0.10 mmol) was placed in 1 mL of anhydrous dichloromethane containing triethylamine (28 µL, 0.20 mmol). Methanesulfonyl chloride (11 mg, 0.10 mmol) was added and the solution was stirred at room temperature for 1 hour. N,N-Dimethyl-ethane-1,2-diamine (44 mg, 0.50 mmol) was added and the solution was allowed to stir for 16 hours at room temperature. The solution was then evaporated to dryness and purified by reverse-phase preparative liquid chromatography to yield the pure product as the trifluoracetic acid salt (20 mg, 0.040 mol, 40%). ESI-MS m/z calc. 498.2. found 499.3 (M+1)⁺. Retention time 2.43 minutes.

Example 31

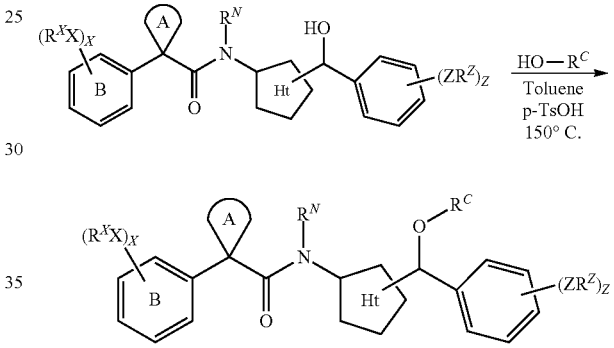

General Procedure: The appropriate alcohol (one equivalent) was placed in a minimum of toluene containing p-toluenesulfonic acid (1.2 equivalents). The appropriate alcohol (1.3 equivalents) was added and the mixture was subjected to microwave irradiation for 5 minutes at 150° C. The mixture was then evaporated to dryness and purified by reverse-phase preparative liquid chromatography to yield the pure product.

Specific Example

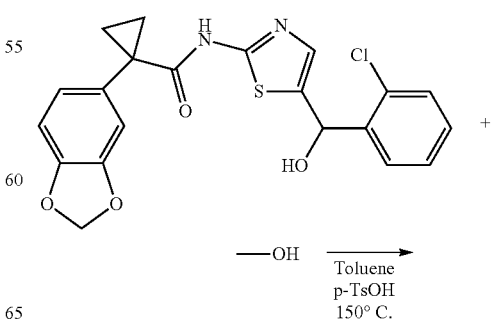

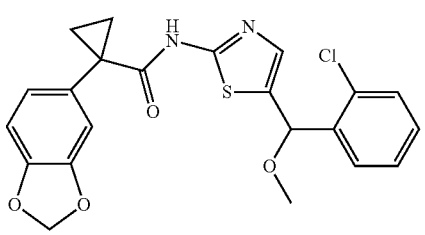

1-Benzo[1,3]dioxol-5-yl-cyclopropanecarboxylic acid {5-[(2-chloro-phenyl)-methoxy-methyl]-thiazol-2-yl}-amide 1-Benzo[1,3]dioxol-5-yl-cyclopropanecarboxylic acid [5-[(2-chloro-phenyl)-hydroxy-methyl]-thiazol-2-yl]-amide (25 mg, 0.058 mmol) was placed in 1 mL of toluene with p-toluenesulfonic acid (14 mg, 0.073 mmol). Methanol (3.0 pt, 0.075 mmol) was added and the solution was subjected to microwave irradiation for 5 minutes at 150° C. The mixture was then evaporated to dryness and purified by reverse-phase preparative liquid chromatography to yield the pure product. (6.0 mg, 0.013 mol, 22%). ESI-MS m/z calc. 515.1. found 443.3 (M+1)⁺. Retention time 3.72 minutes. $^1$H NMR (400 MHz, CD$_3$CN) δ 1.23-1.30 (m, 2H), 1.56-1.67 (m, 2H), 3.38 (s, 3H), 5.88 (s, 1H), 5.99 (s, 2H), 6.84 (d, J=6.2 Hz, 1H), 6.92-6.98 (m, 2H), 7.26 (s, 1H), 7.33-7.38 (m, 1H), 7.41-7.48 (m, 2H), 7.62-7.71 (m, 1H).

Example 32

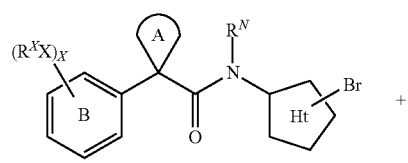

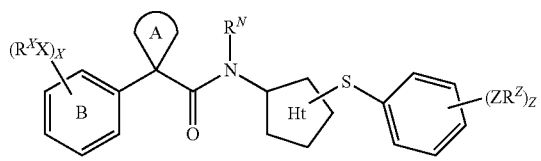

General Procedure: The appropriate aryl halide (1 equivalent) was dissolved in a minimum of ethanol containing potassium hydroxide (2 equivalents). The appropriate thiol (1 equivalent) was added and the mixture is subjected to microwave irradiation for 15 minutes at 115° C. The crude reaction mixture was then separated by reverse-phase preparative liquid chromatography to yield the pure product.

Specific Example

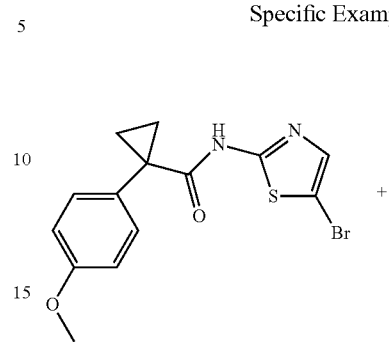

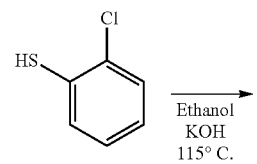

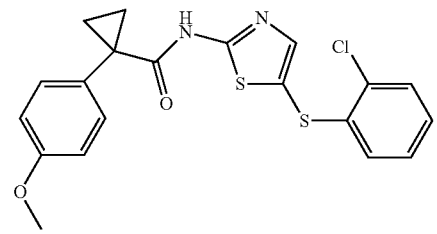

1-(4-Methoxy-phenyl)-cyclopropanecarboxylic acid [5-(2-chloro-phenylsulfanyl)-thiazol-2-yl]-amide 1-(4-Methoxy-phenyl)-cyclopropanecarboxylic acid (5-bromo-thiazol-2-yl)-amide (35 mg, 0.10 mmol) was dissolved in ethanol (0.50 mL) containing potassium hydroxide (11 mg, 0.20 mmol). 2-Chloro-benzenethiol (11 µL, 0.10 mmol) was added and the mixture was subjected to microwave irradiation for 15 minutes at 115° C. The crude reaction mixture was then separated by reverse-phase preparative liquid chromatography to yield the pure product (11 mg, 0.026 mmol, 26%). ESI-MS m/z calc. 416.0. found 417.1 (M+1)⁺. Retention time 4.03 minutes.

Example 33

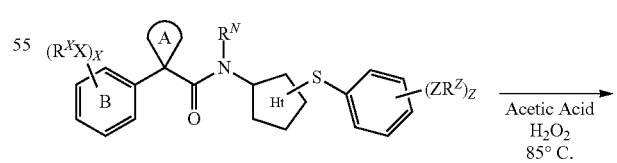

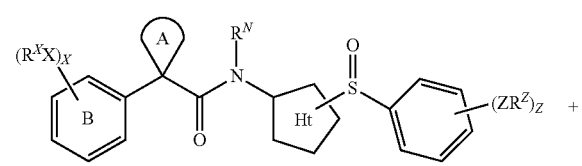

-continued

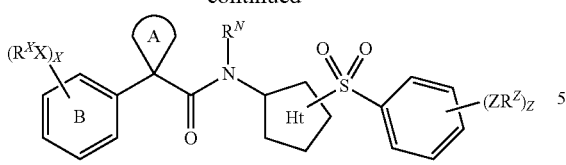

General Procedure: The appropriate sulfide (1 equivalent) was dissolved in a minimum of acetic acid containing hydrogen peroxide (3 equivalents). The mixture was heated at 85° C. and carefully monitored by liquid chromatography/mass spectrometry (LC/MS). After the starting material was consumed, ether and water was added to the mixture. The layers were separated, and the organic layer was dried over sodium sulfate, filtered, and evaporated to dryness. The crude reaction mixture was then separated by reverse-phase preparative liquid chromatography to yield the pure product.

Specific Examples

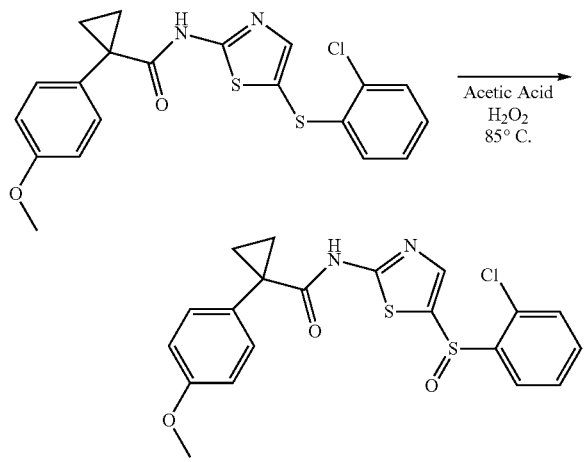

1-(4-Methoxy-phenyl)-cyclopropanecarboxylic acid [5-(2-chloro-benzenesulfinyl)-thiazol-2-yl]-amide 1-(4-Methoxy-phenyl)-cyclopropanecarboxylic acid [5-(2-chloro-phenylsulfanyl)-thiazol-2-yl]-amide (50.0 mg, 0.120 mmol) was dissolved in 3 mL of acetic acid containing hydrogen peroxide (30% aqueous solution, 40.8 mg, 0.360 mmol). The mixture was heated at 85° C. for 1 hour. Ether (1.5 mL) and water (1.5 mL) were added and the layers were separated. the organic layer was dried over sodium sulfate, filtered, and evaporated to dryness. The crude reaction mixture was then separated by reverse-phase preparative liquid chromatography to yield the pure product (20.9 mg, 0.0483 mmol, 40.2%). ESI-MS m/z calc. 432.0. found 433.3 (M+1)$^+$. Retention time 3.34 minutes.

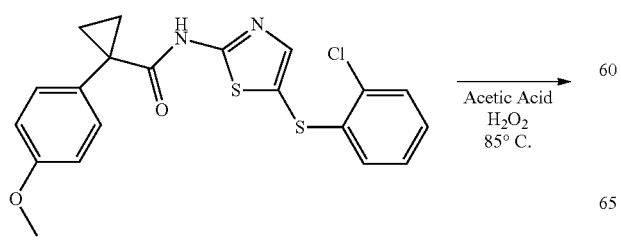

-continued

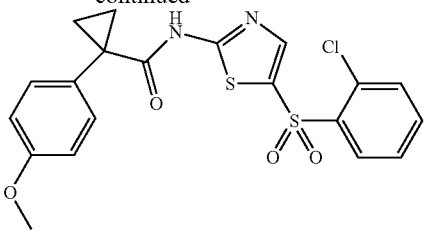

1-(4-Methoxy-phenyl)-cyclopropanecarboxylic acid [5-(2-chloro-benzenesulfinyl)-thiazol-2-yl]-amide 1-(4-Methoxy-phenyl)-cyclopropanecarboxylic acid [5-(2-chloro-phenylsulfanyl)-thiazol-2-yl]-amide (50.0 mg, 0.120 mmol) was dissolved in 3 mL of acetic acid containing hydrogen peroxide (30% aqueous solution, 40.8 mg, 0.360 mmol). The mixture was heated at 85° C. for 1 hour. Ether (1.5 mL) and water (1.5 mL) were added and the layers were separated. The organic layer was dried over sodium sulfate, filtered, and evaporated to dryness. The crude reaction mixture was then separated by reverse-phase preparative liquid chromatography to yield the pure product (19.7 mg, 0.0439 mmol, 36.6%). ESI-MS m/z calc. 448.0. found 449.1 (M+1)$^+$. Retention time 3.53 minutes. $^1$H NMR (400 MHz, CD$_3$CN) δ 1.23-1.35 (m, 2H), 1.61-1.68 (m, 2H), 3.80 (s, 3H), 6.90-7.00 (m, 2H), 7.34-7.41 (m, 2H), 7.54-7.68 (m, 3H), 8.03-8.10 (m, 1H), 8.22-8.30 (m, 1H), 9.32 (s, 1H).

Table 2 below provides analytical data for compounds of Table 1.

TABLE 2

| Cmpd # | LC/MS (M + 1) | LC/MS RT (min) |
|---|---|---|
| 1 | 322.10 | 2.16 |
| 2 | 350.00 | 2.58 |
| 3 | 321.20 | 1.98 |
| 4 | 399.20 | 3.74 |
| 5 | 369.20 | 3.71 |
| 6 | 397.20 | 3.95 |
| 7 | 293.00 | 2.96 |
| 8 | 427.20 | 3.97 |
| 9 | 441.10 | 4.12 |
| 10 | 325.00 | 3.48 |
| 11 | 383.00 | 3.20 |
| 12 | 399.00 | 3.80 |
| 13 | 399.00 | 3.79 |
| 14 | 364.80 | 3.57 |
| 15 | 394.80 | 3.55 |
| 16 | 351.20 | 4.69 |
| 17 | 351.20 | 4.59 |
| 18 | 385.10 | 3.84 |
| 19 | 437.10 | 3.80 |
| 20 | 427.30 | 3.94 |
| 21 | 431.30 | 4.07 |
| 22 | 411.10 | 3.77 |
| 23 | 415.30 | 3.94 |
| 24 | 411.10 | 3.75 |
| 25 | 415.30 | 3.92 |
| 26 | 423.10 | 3.69 |
| 27 | 411.10 | 3.64 |
| 28 | 415.30 | 3.82 |
| 29 | 407.10 | 3.85 |
| 30 | 411.30 | 4.02 |
| 31 | 399.10 | 3.69 |
| 32 | 403.50 | 3.85 |
| 33 | 378.90 | 3.69 |
| 34 | 383.10 | 3.89 |
| 35 | 417.10 | 4.03 |
| 36 | 417.30 | 4.10 |
| 37 | 417.30 | 4.11 |
| 38 | 413.30 | 3.76 |

TABLE 2-continued

| Cmpd # | LC/MS (M + 1) | LC/MS RT (min) |
|---|---|---|
| 39 | 307.10 | 3.28 |
| 40 | 303.10 | 3.10 |
| 41 | 318.10 | 3.31 |
| 42 | 390.30 | 3.82 |
| 43 | 413.00 | 3.83 |
| 44 | 415.00 | 3.85 |
| 45 | 403.30 | 3.10 |
| 46 | 359.10 | 3.82 |
| 47 | 359.10 | 3.74 |
| 48 | 355.10 | 3.47 |
| 49 | 339.30 | 3.75 |
| 50 | 433.30 | 3.34 |
| 51 | 449.10 | 3.53 |
| 52 | 401.30 | 3.83 |
| 53 | 443.30 | 2.90 |
| 54 | 429.30 | 3.02 |
| 55 | 413.30 | 3.12 |
| 56 | 439.30 | 2.71 |
| 57 | 425.30 | 2.78 |
| 58 | 409.30 | 2.95 |
| 59 | 434.30 | 2.48 |
| 60 | 420.30 | 2.58 |
| 61 | 404.50 | 2.75 |
| 62 | 396.10 | 2.34 |
| 63 | 289.30 | 2.88 |
| 64 | 399.00 | 3.42 |
| 65 | 399.00 | 3.47 |
| 66 | 395.00 | 3.25 |
| 67 | 390.00 | 3.00 |
| 68 | 390.00 | 3.05 |
| 69 | 395.00 | — |
| 70 | 413.30 | 3.59 |
| 71 | 471.30 | 3.60 |
| 72 | 498.30 | 2.64 |
| 73 | 498.30 | 2.64 |
| 74 | 498.30 | 2.80 |
| 75 | 408.00 | 2.83 |
| 76 | 365.10 | 3.62 |
| 77 | 385.10 | 3.70 |
| 78 | 381.30 | 3.37 |
| 79 | 365.10 | 3.32 |
| 80 | 399.10 | 3.50 |
| 81 | 379.30 | 3.53 |
| 82 | 399.10 | 3.63 |
| 83 | 395.30 | 3.30 |
| 84 | 302.90 | 2.58 |
| 85 | 365.10 | 3.32 |
| 86 | 429.30 | 3.00 |
| 87 | 445.10 | 3.20 |
| 88 | 417.30 | 3.70 |
| 89 | 417.30 | 3.73 |
| 90 | 336.10 | 2.74 |
| 91 | 332.30 | 2.57 |
| 92 | 415.30 | 3.72 |
| 93 | 411.30 | 3.43 |
| 94 | 398.30 | 3.17 |
| 95 | 398.30 | 2.38 |
| 96 | 427.30 | 3.05 |
| 97 | 412.10 | 3.12 |
| 98 | 427.30 | 3.45 |
| 99 | 412.30 | 2.36 |
| 100 | 441.30 | 2.88 |
| 101 | 431.30 | 3.84 |
| 102 | 431.30 | 3.82 |
| 103 | 427.10 | 3.20 |
| 104 | 397.10 | 3.77 |
| 105 | 441.30 | 3.25 |
| 106 | 344.90 | 3.21 |
| 107 | 403.10 | 3.97 |
| 108 | 403.10 | 3.94 |
| 109 | 390.90 | 3.93 |
| 110 | 433.10 | 4.09 |
| 111 | 394.90 | 3.84 |
| 112 | 425.10 | 3.80 |
| 113 | 395.10 | 3.77 |
| 114 | 399.10 | 4.04 |
| 115 | 409.10 | 3.77 |
| 116 | 433.10 | 4.25 |
| 117 | 434.10 | 3.87 |
| 118 | 443.30 | 3.38 |
| 119 | 436.10 | 2.79 |
| 120 | 381.30 | 3.89 |
| 121 | 381.30 | 3.85 |
| 122 | 385.10 | 4.14 |
| 123 | 419.10 | 4.34 |
| 124 | 429.10 | 3.40 |
| 125 | 433.10 | 4.05 |
| 126 | 392.90 | 3.82 |
| 127 | 425.10 | 3.60 |
| 128 | 419.10 | 4.19 |
| 129 | 394.90 | 3.64 |
| 130 | 517.30 | 3.44 |
| 131 | 517.30 | 3.34 |
| 132 | 546.30 | 2.57 |
| 133 | 517.10 | 3.66 |
| 134 | 503.30 | 3.27 |
| 135 | 427.30 | 3.46 |
| 136 | 429.50 | 3.17 |
| 137 | 544.30 | 2.95 |
| 138 | 516.30 | 2.81 |
| 139 | 532.10 | 2.75 |
| 140 | 488.20 | 2.87 |
| 141 | 530.10 | 3.16 |
| 142 | 497.30 | 2.53 |
| 143 | 456.30 | 2.43 |
| 144 | 511.50 | 2.87 |
| 145 | 503.10 | 3.37 |
| 146 | 489.10 | 3.29 |
| 147 | 375.10 | 2.87 |
| 148 | 361.10 | 2.90 |
| 149 | 417.30 | 3.77 |
| 150 | 349.10 | 3.00 |
| 151 | 417.30 | 3.75 |
| 152 | 383.30 | 3.20 |
| 153 | 400.30 | 3.40 |
| 154 | 383.30 | 3.23 |
| 155 | 379.10 | 3.05 |
| 156 | 379.10 | 3.52 |
| 157 | 413.30 | 3.72 |
| 158 | 431.30 | 3.72 |
| 159 | 413.30 | 3.71 |
| 160 | 431.50 | 3.74 |
| 161 | 363.30 | 2.98 |
| 162 | 431.50 | 3.69 |
| 163 | 396.90 | 3.17 |
| 164 | 431.30 | 3.69 |
| 165 | 397.30 | 3.18 |
| 166 | 414.30 | 3.38 |
| 167 | 397.10 | 3.20 |
| 168 | 392.90 | 3.03 |
| 169 | 410.10 | 2.40 |
| 170 | 398.30 | 2.96 |
| 171 | 449.00 | 3.80 |
| 172 | 411.00 | 3.69 |
| 173 | 453.00 | 3.98 |
| 174 | 415.00 | 3.90 |
| 175 | 396.30 | 3.27 |
| 176 | 410.30 | 3.23 |
| 177 | 395.00 | 3.58 |
| 178 | 413.00 | 3.64 |
| 179 | 395.00 | 3.54 |
| 180 | 409.00 | 3.54 |
| 181 | 427.00 | 3.60 |
| 182 | 409.00 | 3.48 |
| 183 | 389.30 | 3.94 |
| 184 | 496.30 | 2.52 |
| 185 | 510.50 | 2.62 |
| 186 | 499.30 | 2.43 |
| 187 | 541.50 | 2.41 |
| 188 | 382.30 | 2.47 |
| 189 | 357.30 | 2.86 |
| 190 | 375.00 | 3.07 |
| 191 | 402.00 | 3.11 |
| 192 | 413.30 | 3.62 |

TABLE 2-continued

| Cmpd # | LC/MS (M + 1) | LC/MS RT (min) |
| --- | --- | --- |
| 193 | 409.50 | 3.67 |
| 194 | 467.30 | 3.84 |
| 195 | 427.10 | 3.58 |
| 196 | 423.10 | 3.64 |
| 197 | 401.10 | 3.60 |
| 198 | 405.10 | 3.75 |
| 199 | 409.30 | 3.47 |
| 200 | 413.30 | 3.63 |
| 201 | 481.00 | 3.78 |
| 202 | 498.30 | 2.92 |
| 203 | 418.10 | 2.63 |
| 204 | 430.10 | 3.30 |
| 205 | 445.30 | 2.28 |
| 206 | 487.50 | 2.29 |
| 207 | 366.70 | 2.71 |
| 208 | 381.10 | 2.68 |
| 209 | 422.90 | 3.63 |
| 210 | 496.30 | 2.60 |
| 211 | 496.30 | 2.60 |
| 212 | 541.30 | 2.50 |
| 213 | 486.30 | 2.68 |
| 214 | 482.30 | 2.76 |
| 215 | 372.30 | 3.29 |
| 216 | 526.10 | 3.57 |
| 217 | 482.30 | 3.00 |
| 218 | 526.30 | 3.03 |
| 219 | 516.30 | 2.71 |
| 220 | 526.30 | 2.88 |
| 221 | 470.30 | 2.85 |
| 222 | 526.30 | 2.83 |
| 223 | 512.30 | 2.78 |
| 224 | 539.30 | 3.22 |
| 225 | 526.10 | 3.07 |
| 226 | 498.10 | 2.76 |
| 227 | 554.30 | 3.05 |
| 228 | 512.10 | 2.81 |
| 229 | 512.30 | 2.81 |
| 230 | 525.30 | 2.86 |
| 231 | 510.30 | 3.02 |
| 232 | 498.10 | 3.05 |
| 233 | 526.30 | 2.97 |
| 234 | 539.50 | 2.86 |
| 235 | 555.30 | 2.61 |
| 236 | 485.30 | 2.76 |
| 237 | 555.30 | 2.81 |
| 238 | 537.50 | 2.90 |
| 239 | 457.30 | 3.86 |
| 240 | 478.90 | 2.55 |
| 241 | 395.90 | 2.21 |
| 242 | 420.90 | 3.69 |
| 243 | 410.30 | 2.19 |
| 244 | 435.30 | 3.67 |
| 245 | 417.30 | 3.50 |
| 246 | 514.34 | 2.81 |
| 247 | 419.00 | 3.86 |
| 248 | 542.00 | 2.73 |
| 249 | 556.20 | 2.90 |
| 250 | 469.20 | 4.09 |
| 251 | 471.20 | 4.25 |
| 252 | 540.40 | 2.81 |
| 253 | 500.00 | 2.71 |
| 254 | 526.20 | 2.76 |
| 255 | 526.20 | 3.30 |
| 256 | 526.20 | 3.08 |
| 257 | 513.10 | 4.00 |
| 258 | 513.30 | 4.09 |
| 259 | 443.30 | 3.72 |
| 260 | 471.30 | 4.02 |
| 261 | 400.30 | 3.02 |
| 262 | 396.30 | 2.40 |
| 263 | 401.30 | 3.63 |
| 264 | 414.30 | 2.96 |
| 265 | 410.30 | 2.38 |
| 266 | 413.10 | 3.33 |
| 267 | 413.10 | 3.33 |
| 268 | 415.30 | 3.58 |
| 269 | 399.10 | 3.32 |
| 270 | 570.30 | 2.82 |
| 271 | 473.10 | 3.19 |
| 272 | 487.30 | 3.62 |
| 273 | 487.30 | 3.27 |
| 274 | 501.30 | 3.34 |
| 275 | 514.10 | 2.66 |
| 276 | 556.30 | 2.54 |
| 277 | 570.10 | 2.61 |
| 278 | 584.30 | 2.67 |
| 279 | 379.10 | 3.72 |
| 280 | 393.10 | 3.65 |
| 281 | 397.30 | 3.74 |
| 282 | 411.10 | 3.70 |
| 283 | 443.00 | 3.66 |
| 284 | 364.11 | 2.65 |
| 285 | 395.10 | 2.81 |
| 286 | 429.11 | 2.98 |
| 287 | 429.06 | 3.26 |
| 288 | 427.05 | 3.16 |
| 289 | 344.08 | 2.72 |
| 290 | 386.13 | 3.12 |
| 291 | 437.17 | 2.69 |
| 292 | 303.09 | 2.37 |
| 293 | 365.08 | 2.73 |
| 294 | 378.10 | 2.92 |
| 295 | 375.16 | 2.66 |
| 296 | 380.12 | 3.06 |
| 297 | 375.16 | 2.49 |
| 298 | 429.10 | 3.15 |
| 299 | 365.08 | 2.15 |
| 300 | 359.10 | 2.66 |
| 301 | 407.10 | 3.11 |
| 302 | 416.05 | 3.01 |
| 303 | 425.10 | 1.36 |
| 304 | 423.09 | 2.33 |
| 305 | 428.11 | 3.13 |
| 306 | 428.11 | 3.06 |
| 307 | 435.09 | 2.33 |
| 308 | 461.06 | 2.37 |
| 309 | 446.05 | 2.37 |
| 310 | 498.30 | 2.33 |
| 311 | 498.30 | 2.35 |
| 312 | 468.14 | 1.40 |
| 313 | 453.13 | 2.75 |
| 314 | 466.16 | 1.46 |
| 315 | 453.13 | 2.76 |
| 316 | 384.07 | 2.44 |
| 317 | 384.07 | 2.42 |
| 318 | 455.30 | 1.95 |
| 319 | 388.30 | 1.90 |
| 320 | 388.30 | 1.92 |
| 321 | 540.10 | 2.62 |
| 322 | 429.30 | 3.15 |
| 323 | 429.30 | 3.15 |
| 324 | 526.34 | 3.03 |
| 325 | 512.34 | 2.82 |
| 326 | 525.14 | 2.81 |
| 327 | 482.30 | 2.98 |
| 328 | 482.33 | 2.96 |
| 329 | 498.30 | 2.88 |
| 330 | 512.30 | 2.90 |
| 331 | 526.30 | 3.04 |
| 332 | 496.30 | 3.01 |
| 333 | 525.10 | 2.80 |
| 334 | 498.33 | 2.93 |
| 335 | 498.30 | 3.01 |
| 336 | 456.30 | 2.88 |
| 337 | 496.33 | 3.02 |
| 338 | 456.32 | 2.88 |
| 339 | 484.33 | 2.95 |
| 340 | 526.30 | 3.11 |
| 341 | 484.30 | 3.04 |
| 342 | 526.34 | 3.02 |
| 343 | 498.33 | 2.85 |
| 344 | 492.33 | 2.88 |
| 345 | 522.34 | 2.93 |
| 346 | 494.33 | 2.76 |

TABLE 2-continued

| Cmpd # | LC/MS (M + 1) | LC/MS RT (min) |
|---|---|---|
| 347 | 492.33 | 2.86 |
| 348 | 508.34 | 2.68 |
| 349 | 492.33 | 2.89 |
| 350 | 451.92 | 2.75 |
| 351 | 478.33 | 2.79 |
| 352 | 494.33 | 2.65 |
| 353 | 522.34 | 2.92 |
| 354 | 478.33 | 2.82 |
| 355 | 492.33 | 2.85 |
| 356 | 421.91 | 2.70 |
| 357 | 479.93 | 2.80 |
| 358 | 522.34 | 2.93 |
| 359 | 447.92 | 2.79 |
| 360 | 508.34 | 2.68 |
| 361 | 492.33 | 2.92 |
| 362 | 477.93 | 2.79 |
| 363 | 522.34 | 2.95 |
| 364 | 452.32 | 2.70 |
| 365 | 480.33 | 2.86 |
| 366 | 452.32 | 2.72 |
| 367 | 494.33 | 2.68 |
| 368 | 463.92 | 2.63 |
| 369 | 464.32 | 2.72 |
| 370 | 521.14 | 2.72 |
| 371 | 462.32 | 2.78 |
| 372 | 449.92 | 2.79 |
| 373 | 478.33 | 2.80 |
| 374 | 494.33 | 2.76 |
| 375 | 570.36 | 2.65 |
| 376 | 527.94 | 2.62 |
| 377 | 569.15 | 2.52 |
| 378 | 542.35 | 2.49 |
| 379 | 570.36 | 2.66 |
| 380 | 555.95 | 2.48 |
| 381 | 500.33 | 2.51 |
| 382 | 542.35 | 2.59 |
| 383 | 442.32 | 2.84 |
| 384 | 471.53 | 2.72 |
| 385 | 526.34 | 2.55 |
| 386 | 329.08 | 3.51 |
| 387 | 472.33 | 2.93 |
| 388 | 540.35 | 2.62 |
| 389 | 472.33 | 2.89 |
| 390 | 444.32 | 2.59 |
| 391 | 428.31 | 2.75 |
| 392 | 458.32 | 2.59 |
| 393 | 430.31 | 2.81 |
| 394 | 444.32 | 2.68 |
| 395 | 402.31 | 2.63 |
| 396 | 430.31 | 2.22 |
| 397 | 400.30 | 2.36 |
| 398 | 416.31 | 2.33 |
| 399 | 494.33 | 2.72 |
| 400 | 494.33 | 2.73 |
| 401 | 444.32 | 2.69 |
| 402 | 416.31 | 2.42 |
| 403 | 414.31 | 2.46 |
| 404 | 444.32 | 2.63 |
| 405 | 539.15 | 2.49 |
| 406 | 525.14 | 2.75 |
| 407 | 513.14 | 2.80 |
| 408 | 536.35 | 2.46 |
| 409 | 524.34 | 3.25 |
| 410 | 499.93 | 2.82 |
| 411 | 510.34 | 3.06 |
| 412 | 508.34 | 2.92 |
| 413 | 524.34 | 3.16 |
| 414 | 496.33 | 2.95 |
| 415 | 468.33 | 2.76 |
| 416 | 472.33 | 2.68 |
| 417 | 482.33 | 2.95 |
| 418 | 539.15 | 2.73 |
| 419 | 487.93 | 2.82 |
| 420 | 484.33 | 2.76 |
| 421 | 472.33 | 2.79 |
| 422 | 468.33 | 2.96 |
| 423 | 453.92 | 2.73 |
| 424 | 486.33 | 2.75 |
| 425 | 514.34 | 3.02 |
| 426 | 514.34 | 2.89 |
| 427 | 536.35 | 3.32 |
| 428 | 512.34 | 3.22 |
| 429 | 540.35 | 2.95 |
| 430 | 533.14 | 2.65 |
| 431 | 516.34 | 2.63 |
| 432 | 456.32 | 2.77 |
| 433 | 502.34 | 2.64 |
| 434 | 512.34 | 2.89 |
| 435 | 524.34 | 3.16 |
| 436 | 513.14 | 2.70 |
| 437 | 486.30 | 2.70 |
| 438 | 528.34 | 3.05 |
| 439 | 486.33 | 2.86 |
| 440 | 514.30 | 2.90 |
| 441 | 522.34 | 3.02 |
| 442 | 522.34 | 2.92 |
| 443 | 484.33 | 2.79 |
| 444 | 468.32 | 2.86 |
| 445 | 522.34 | 3.05 |
| 446 | 487.93 | 2.92 |
| 447 | 472.33 | 2.75 |
| 448 | 472.33 | 2.75 |
| 449 | 487.93 | 2.96 |
| 450 | 468.32 | 2.93 |
| 451 | 514.34 | 2.66 |
| 452 | 484.33 | 2.79 |
| 453 | 496.33 | 2.80 |
| 454 | 510.34 | 2.88 |
| 455 | 540.35 | 2.95 |
| 456 | 540.35 | 2.93 |
| 457 | 470.33 | 2.72 |
| 458 | 539.15 | 2.69 |
| 459 | 498.33 | 2.82 |
| 460 | 526.34 | 2.65 |
| 461 | 512.34 | 2.75 |
| 462 | 512.34 | 2.65 |
| 463 | 492.30 | 2.89 |
| 464 | 531.90 | 2.78 |
| 465 | 466.30 | 2.69 |
| 466 | 478.30 | 2.65 |
| 467 | 515.90 | 3.02 |
| 468 | 516.30 | 2.90 |
| 469 | 462.30 | 2.76 |
| 470 | 531.90 | 2.85 |
| 471 | 483.90 | 2.72 |
| 472 | 482.30 | 2.53 |
| 473 | 508.30 | 2.73 |
| 474 | 500.30 | 2.62 |
| 475 | 428.30 | 2.35 |
| 476 | 538.35 | 3.02 |
| 477 | 508.34 | 2.94 |
| 478 | 524.34 | 2.86 |
| 479 | 493.93 | 3.00 |
| 480 | 529.94 | 2.89 |
| 481 | 547.95 | 2.92 |
| 482 | 512.34 | 2.87 |
| 483 | 498.33 | 2.72 |
| 484 | 516.34 | 2.77 |
| 485 | 514.34 | 2.86 |
| 486 | 500.33 | 2.71 |
| 487 | 486.33 | 2.65 |
| 488 | 528.34 | 2.93 |
| 489 | 514.34 | 2.85 |
| 490 | 528.34 | 3.04 |
| 491 | 528.34 | 2.99 |
| 492 | 534.30 | 2.61 |
| 493 | 559.95 | 2.98 |
| 494 | 527.94 | 2.89 |
| 495 | 528.34 | 2.92 |
| 496 | 544.35 | 2.81 |
| 497 | 528.34 | 2.96 |
| 498 | 574.36 | 3.01 |

Example 34

B) Assays for Detecting and Measuring ΔF508-CFTR Correction Properties of Compounds

I) Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3x with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hoursB) Electrophysiological Assays for assaying ΔF508-CFTR modulation properties of compounds 1. Ussing Chamber Assay Ussing chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

Identification of Correction Compounds

Typical protocol utilized a basolateral to apical membrane concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 µM) and all test compounds were added to both sides of the cell culture inserts. The efficacy of the putative ΔF508-CFTR potentiators was compared to that of the known potentiator, genistein.

Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

Cell Culture

Fisher rat epithelial (FRT) cells expressing ΔF508-CFTR ($FRT^{\Delta F508-CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 mL/min using a gravity-driven perfusion system.

Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≦2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Compounds of the invention are useful as modulators of ATP binding cassette transporters. FIG. 2 illustrates the EC50 and relative efficacy of exemplary embodiments of the present invention.

In FIG. 2, the following meanings apply:
EC50. "+++" means <10 uM; "++" means between 10 uM to 25 uM; "+" means between 25 uM to 60 uM.
% Efficacy: "+" means <25%; "++" means between 25% to 100%; "+++" means >100%.

The invention claimed is:

1. A method of increasing the number of functional ABC transporters in a membrane of a cell, comprising the step of contacting said cell with a compound having formula IIIB:

IIIB

[Chemical structure]

wherein:
$X_9$ is $CH_2$, $CF_2$, $CH_2-CH_2$, or $CF_2-CF_2$;
m is 0 to 4;
$Ht_1$ is a 5-membered heteroaromatic ring containing 1-4 heteroatoms selected from O, S, N, or NH;
x, q, and z is independently 0-5;
Q-$R^Q$, X—$R^X$ and Z—$R^Z$ each is independently R';
L is a bond, O, S, SO, $SO_2$, C(O), NR', $C_{1-4}$ aliphatic, or CHR$^L$;
$R^L$ is —OR', —SR', —SOR', —$SO_2$R', or —N(R')$_2$; or L is [structure with A'];

wherein ring A' is a 3-7 membered monocyclic ring having 0-3 heteroatoms selected from O, S, N, or NH, wherein ring A' is optionally substituted with q occurrences of -QR$^Q$;

Ar is phenyl or a six-membered heteroaromatic ring;
R' is independently selected from hydrogen or an optionally substituted group selected from a $C_1-C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; or
R' is independently $R^1$, $R^2$, $R^3$, $R^4$, or $R^5$;
$R^1$ is oxo, $R^6$ or ((C1-C4)aliphatic)$_n$-Y; or two $R^1$ on adjacent ring atoms, taken together, form 1,2-methylenedioxy, 1,2-difluoromethylenedioxy, 1,2-ethylenedioxy, or 1,2-tetrafluoroethylenedioxy;
n is 0 or 1;
Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
$R^2$ is aliphatic, wherein each $R^2$ optionally comprises up to 2 substituents independently selected from $R^1$, $R^4$, or $R^5$;
$R^3$ is a cycloaliphatic, aryl, heterocyclic, or heteroaryl ring optionally comprising up to 3 substituents, independently selected from $R^1$, $R^2$, $R^4$ or $R^5$;
$R^4$ is $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $SR^6$, $SR^5$, $S(O)R^6$, $S(O)R^5$, $SO_2R^6$, $SO_2R^5$, $SO_2N(R^6)_2$, $SO_2N(R^5)_2$, $SO_2NR^5R^6$, $SO_3R^6$, $SO_3R^5$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^6$, $NR^5SO_2R^5$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;
$R^5$ is a cycloaliphatic, aryl, heterocyclic, or heteroaryl ring, optionally comprising up to 3 $R^1$ substituents;
$R^6$ is H or aliphatic, wherein $R^6$ optionally comprises a $R^7$ substituent;
$R^7$ is a cycloaliphatic, aryl, heterocyclic, or heteroaryl ring, and each $R^7$ optionally comprises up to 2 substituents independently chosen from H, (C1-C6)-straight or branched alkyl, ($C_2-C_6$) straight or branched alkenyl or alkynyl, 1,2-methylenedioxy, 1,2-ethylenedioxy, or $(CH_2)_n$—Z';
Z' is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, N(aliphatic)$R^8$, $NHR^8$, COOH, C(O)O(-aliphatic), or O-aliphatic; and
$R^8$ is an amino protecting group.

2. The method of claim 1, wherein the ABC transporter is CFTR.

3. A method of treating a condition, disease, or disorder in a patient implicated by CFTR transporter activity wherein the condition, disease, or disorder is cystic fibrosis, comprising the step of administering to said patient a compound having formula IIIB:

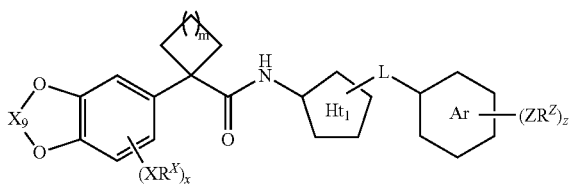

IIIB wherein:
$X_9$ is $CH_2$, $CF_2$, $CH_2$—$CH_2$, or $CF_2$—$CF_2$;
m is 0 to 4;
$Ht_1$ is a 5-membered heteroaromatic ring containing 1-4 heteroatoms selected from O, S, N, or NH;
x, q, and z is independently 0-5;
Q-$R^Q$, X—$R^x$ and Z—$R^Z$ each is independently R';
L is a bond, O, S, SO, $SO_2$, C(O), NR', $C_{1-4}$ aliphatic, or CH$R^L$;
$R^L$ is —OR', —SR', —SOR', —$SO_2$R', or —N(R')$_2$; or L is

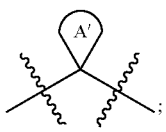

wherein ring A' is a 3-7 membered monocyclic ring having 0-3 heteroatoms selected from O, S, N, or NH, wherein ring A' is optionally substituted with q occurrences of -Q$R^Q$;
Ar is phenyl or a six-membered heteroaromatic ring;
R' is independently selected from hydrogen or an optionally substituted group selected from a $C_1$-$C_8$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; or
R' is independently $R^1$, $R^2$, $R^3$, $R^4$, or $R^5$;
$R^1$ is oxo, $R^6$ or ((C1-C4)aliphatic)$_n$-Y; or two $R^1$ on adjacent ring atoms, taken together, form 1,2-methylenedioxy, 1,2-difluoromethylenedioxy, 1,2-ethylenedioxy, or 1,2-tetrafluoroethylenedioxy;
n is 0 or 1;
Y is halo, CN, $NO_2$, $CF_3$, $OCF_3$, OH, $SR^6$, S(O)$R^6$, $SO_2R^6$, $NH_2$, NH$R^6$, N($R^6$)$_2$, $NR^6R^8$, COOH, COO$R^6$ or O$R^6$;
$R^2$ is aliphatic, wherein each $R^2$ optionally comprises up to 2 substituents independently selected from $R^1$, $R^4$, or $R^5$;
$R^3$ is a cycloaliphatic, aryl, heterocyclic, or heteroaryl ring optionally comprising up to 3 substituents, independently selected from $R^1$, $R^2$, $R^4$ or $R^5$;
$R^4$ is O$R^5$, O$R^6$, OC(O)$R^6$, OC(O)$R^5$, OC(O)O$R^6$, OC(O)O$R^5$, OC(O)N($R^6$)$_2$, OC(O)N($R^5$)$_2$, OC(O)N($R^6R^5$), S$R^6$, S$R^5$, S(O)$R^6$, S(O)$R^5$, $SO_2R^6$, $SO_2R^5$, $SO_2N(R^6)_2$, $SO_2N(R^5)_2$, $SO_2NR^5R^6$, $SO_3R^6$, $SO_3R^5$, C(O)$R^5$, C(O) O$R^5$, C(O)$R^6$, C(O)O$R^6$, C(O)N($R^6$)$_2$, C(O)N($R^5$)$_2$, C(O)N($R^5R^6$), C(O)N(O$R^6$)$R^6$, C(O)N(O$R^5$)$R^6$, C(O) N(O$R^6$)$R^5$, C(O)N(O$R^5$)$R^5$, C(NO$R^6$)$R^6$, C(NO$R^6$)$R^5$, C(NO$R^5$)$R^6$, C(NO$R^5$)$R^5$, N($R^6$)$_2$, N($R^5$)$_2$, N($R^5R^6$), $NR^5C(O)R^5$, $NR^6C(O)R^6$, $NR^6C(O)R^5$, $NR^5C(O)R^6$, $NR^6C(O)OR^6$, $NR^5C(O)OR^5$, $NR^6C(O)OR^5$, $NR^5C(O)$ O$R^5$, $NR^6C(O)N(R^6)_2$, $NR^6C(O)NR^5R^6$, $NR^6C(O)N$ ($R^5$)$_2$, $NR^5C(O)N(R^6)_2$, $NR^5C(O)NR^5R^6$, $NR^5C(O)N$ ($R^5$)$_2$, $NR^6SO_2R^6$, $NR^6SO_2R^5$, $NR^5SO_2R^6NR^5SO_2R^5$, $NR^6SO_2N(R^6)_2$, $NR^6SO_2NR^5R^6$, $NR^6SO_2N(R^5)_2$, $NR^5SO_2N(R^6)_2$, $NR^5SO_2NR^5R^6$, $NR^5SO_2N(R^5)_2$, N(O$R^6$)$R^6$, N(O$R^6$)$R^5$, N(O$R^5$)$R^5$, or N(O$R^5$)$R^6$;
$R^5$ is a cycloaliphatic, aryl, heterocyclic, or heteroaryl ring, optionally comprising up to 3 $R^1$ substituents;
$R^6$ is H or aliphatic, wherein $R^6$ optionally comprises a $R^7$ substituent;
$R^7$ is a cycloaliphatic, aryl, heterocyclic, or heteroaryl ring, and each $R^7$ optionally comprises up to 2 substituents independently chosen from H, (C1-C6)-straight or branched alkyl, ($C_2$-$C_6$) straight or branched alkenyl or alkynyl, 1,2-methylenedioxy, 1,2-ethylenedioxy, or ($CH_2$)$_n$—Z';
Z' is selected from halo, CN, $NO_2$, $CF_3$, $OCF_3$, OH, S-aliphatic, S(O)-aliphatic, $SO_2$-aliphatic, $NH_2$, NH-aliphatic, N(aliphatic)$_2$, N(aliphatic)$R^8$, NH$R^8$, COOH, C(O)O(-aliphatic), or O-aliphatic; and
$R^8$ is an amino protecting group.

4. The method of claim 3, wherein two R' in N(R')$_2$ taken together with the nitrogen atom, form an optionally substituted 3-7 membered heterocyclic ring containing up to 4 heteroatoms selected from O, N, or S.

5. The method of claim 3, wherein m is 0.

6. The method of claim 3, wherein $Ht_1$ is a thiazolyl ring, wherein Ht is optionally substituted with up to three substituents.

7. The method of claim 3, wherein $X_9$ is $CH_2$.

8. The method of claim 3, wherein $X_9$ is $CF_2$.

9. The method of claim 3, wherein L is —$CH_2$—.

10. The method of claim 3, wherein L is —CH—$R^L$, wherein $R^L$ is —OH, —NHR$^D$, or NR$^{AA}$R$^{BB}$; wherein
each of R$^{AA}$, R$^{BB}$, and R$^D$ is independently hydrogen, C1-C6 aliphatic, C3-C7 cycloalkyl, (C3-C7-cycloalkyl)-C1-C6 aliphatic, (C3-C7-cycloalkenyl)-C1-C6-aliphatic, 3-7-membered heterocyclyl, (3-7-membered heterocyclyl)-C1-C6-aliphatic, 3-6 membered heteroaryl, (3-6-membered heteroaryl)-C1-C6 aliphatic, wherein said aliphatic, cycloalkyl, cycloalkenyl, heterocyclyl, or heteroaryl is optionally substituted with up to three substituents selected from OH, —O($C_{1-4}$-aliphatic), or (C1-C4 aliphatic)$_p$-Y; wherein
p is 0 or 1;
Y is OR or NHC(O)R;
R is hydrogen or $C_{1-4}$ aliphatic; or
R$^{AA}$ and R$^{BB}$, taken together with the nitrogen atom, is a 3-7 membered heterocyclic ring containing up to 4 heteroatoms selected from 0, wherein said ring is optionally substituted with up to 2 substituents selected from oxo or (C1-C4 aliphatic)$_p$—Y; and
wherein up to two methylene groups in any said aliphatic above are optionally and independently replaced with O, C(O), or NH.

11. The method of claim 10, wherein R$^D$ is hydrogen.

12. The method of claim 10, wherein R$^D$ is optionally substituted $C_1$-$C_6$ aliphatic.

13. The compound according to claim 10, wherein R$^D$ is selected from C1-C6 alkyl, optionally substituted with up two substituents selected from OH, —O(C1-C4 alkyl), acetamido, $NH_2$, NH(C1-C4 alkyl), or N(C1-C4 alkyl)$_2$.

14. The method of claim 10, wherein $R^D$ is selected from an optionally substituted C3-C6 cycloalkyl, or (C3-C6 cycloalkyl or cycloalkenyl ring)-C1-C6 aliphatic.

15. The method of claim 10, wherein $R^D$ is selected from cyclopropyl, cyclobutyl, cyclopentyl, cyclohexyl, cyclohexenylethyl or cyclohexylmethyl.

16. The method of claim 10, wherein $R^D$ is selected from optionally substituted 3-7 membered heterocyclyl or (3-7 membered heterocyclyl)-C1-C6 aliphatic, wherein said heterocyclyl contains up to 2 heteroatoms selected from O, S, or N.

17. The method of claim 10, wherein $R^D$ is selected from (N-methyl-pyrrolidin-2-yl)-ethyl, pyrrolidin-1-yl-ethyl, tetrahydrofuran-2-yl-methyl, morpholin-4-yl-ethyl, or morpholin-4-yl-propyl.

18. The method of claim 10, wherein $R^D$ is selected from optionally substituted 5-6 membered heteroaryl or (5-6-membered heteroaryl)-C1-C6 aliphatic, wherein said heteroaryl contains up to 2 heteroatoms selected from O, S, or N.

19. The method of claim 10, wherein $R^D$ is selected from imidazolylpropyl, furanylmethyl, or pyridinylethyl.

20. The method of claim 10, wherein $R^D$ is selected from $C_{1-4}$ alkyl optionally substituted with —OH, or —O($C_{1-4}$ alkyl).

21. The method of claim 10, wherein $R^D$ is selected from $C_{1-4}$ alkyl optionally substituted with 5-6 membered heterocyclic ring containing up to 2 heteroatoms selected from O, N, or S, wherein said ring is optionally substituted with up to 2 substituents selected from ($C_{1-4}$ aliphatic)-Y, wherein Y is halo, —OH, or —O($C_{1-4}$ alkyl).

22. The method of claim 10, wherein $R^D$ is selected from $C_{1-6}$ alkyl optionally substituted with —OH or —O($C_{1-4}$ alkyl).

23. The method of claim 10, wherein one of $R^{AA}$ and $R^{BB}$ is C1-C4 alkyl, and the other of $R^{AA}$ and $R^{BB}$ is selected from C1-C4 alkyl, C2-C4 alkenyl, C3-C6 cycloalkyl, (C3-C6 cycloalkyl)-C1-C4 alkyl, wherein said alkyl, alkenyl, or cycloalkenyl has up to 2 substituents selected from OH or —O(C1-C4 alkyl).

24. The method of claim 10, wherein $R^{AA}$ and $R^{BB}$, taken together with the nitrogen atom, forms a ring selected from pyrrolidinyl, piperidinyl, or morpholinyl, wherein said ring is optionally substituted with up to two substituents selected from hydroxy, COOH, acetoxy, hydroxymethyl, methoxymethyl, hydroxyethyl, methoxyethyl, or ethylenedioxy.

25. The method of claim 10, wherein said compound has formula VB-3-i:

VB-3-i

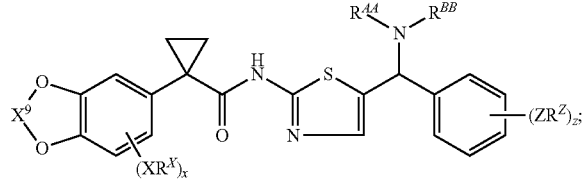

wherein $X^9$ is $CH_2$ or $CF_2$;
$R^{AA}$ and $R^{BB}$ are selected from hydrogen, C1-C6 alkyl, or —CH(C1-C6 alkyl)-CH$_2$OH; or
$R^{AA}$ and $R^{BB}$ taken together form a pyrrolidinyl ring optionally substituted with (C1-C4 aliphatic)$_p$-Y.

26. The method of claim 25, wherein $R^{AA}$ and $R^{BB}$ taken together is 3-acetoxy-pyrrolidin-1-yl, 2-methoxymethyl-pyrrolidin-1-yl, 2-hydroxymethyl-pyrrolidin-1-yl, (2-carboxy-pyrrolidin-1-yl), pyrrolidin-1-yl, or 3-hydroxy-pyrrolidin-1-yl.

27. The method of claim 25, wherein $R^{AA}$ is hydrogen, and $R^{BB}$ is —CH(C1-C6 alkyl)-CH$_2$OH.

28. The method of claim 27, wherein said alkyl is methyl, ethyl, n-propyl, isopropyl, n-butyl, t-butyl, or isobutyl.

29. The method of claim 3, wherein the compound selected from the following table:

| Cmpd # | Compound |
|---|---|
| 321 | ![structure] |
| 322 | ![structure] |
| 323 | ![structure] |
| 324 | ![structure] |

| Cmpd # | Compound |
|---|---|
| 325 | 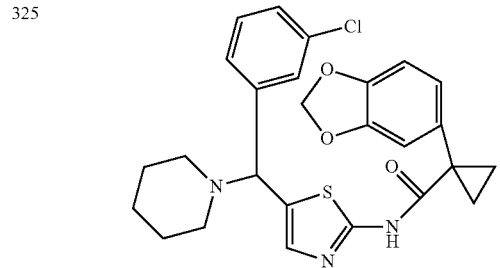 |
| 326 | 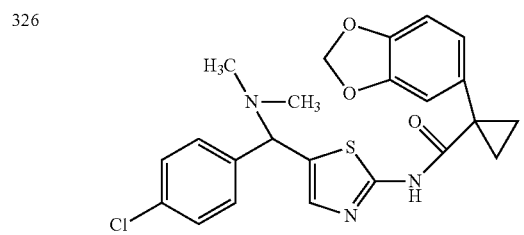 |
| 327 | 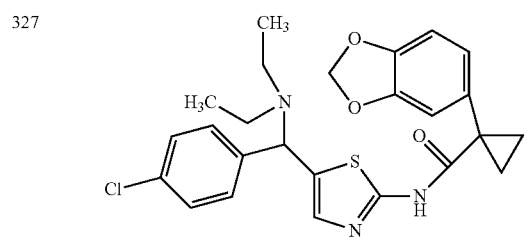 |
| 328 | 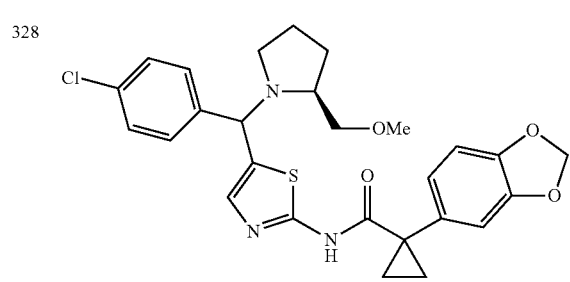 |
| 329 | 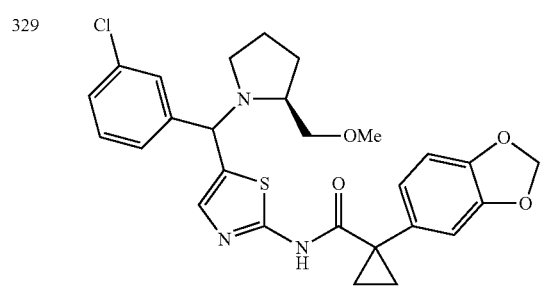 |
| 330 | 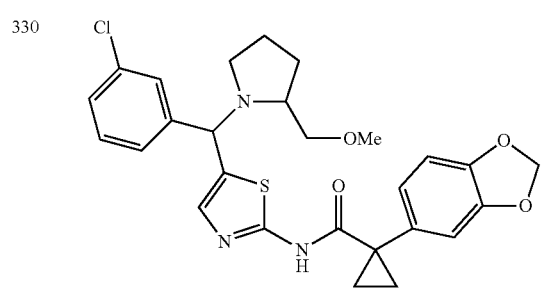 |
| Cmpd # | Compound |
|---|---|
| 331 | 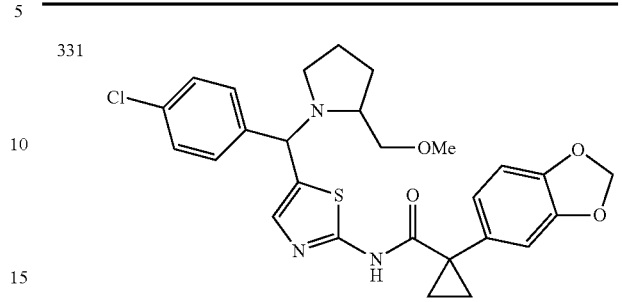 |
| 332 | 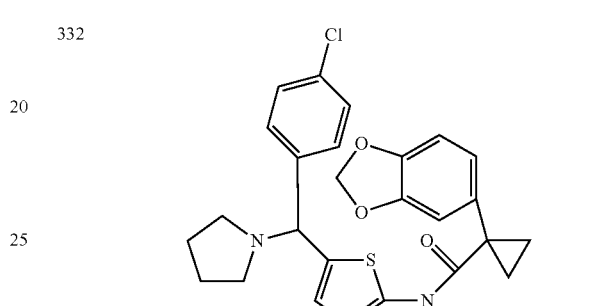 |
| 333 | 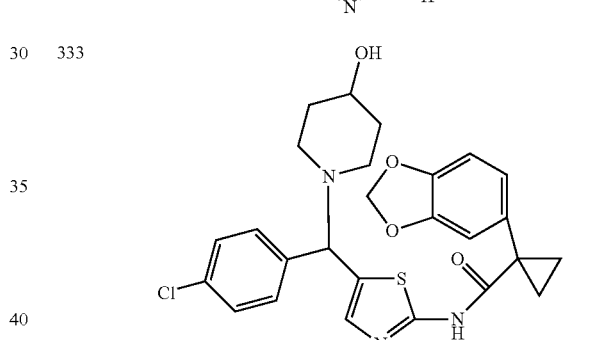 |
| 334 | 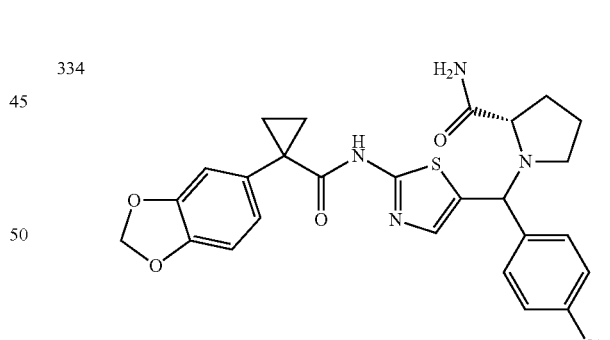 |
| 335 | 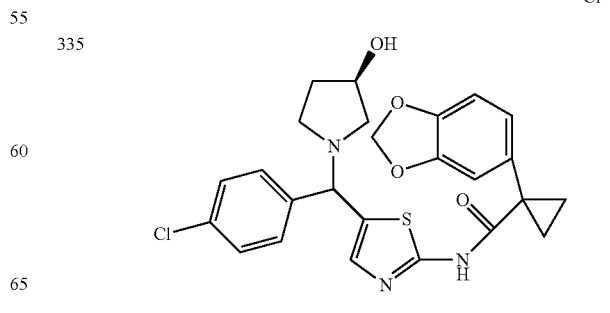 |

| Cmpd # | Compound |
|---|---|
| 336 | 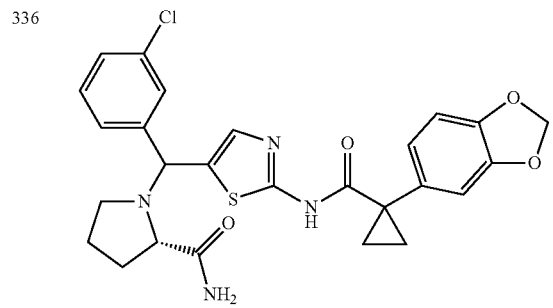 |
| 337 | 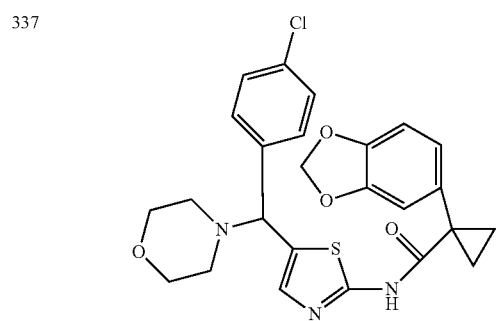 |
| 338 | 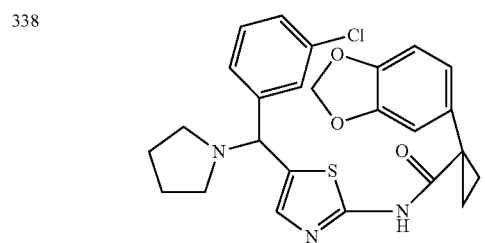 |
| 339 | 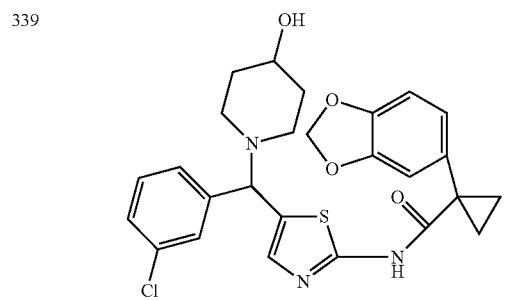 |
| 340 | 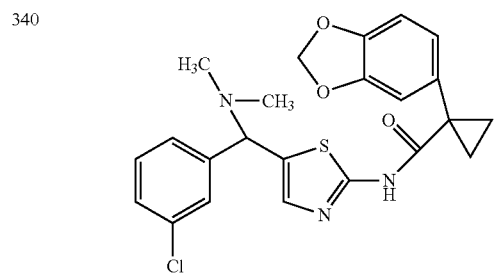 |
| Cmpd # | Compound |
|---|---|
| 341 | 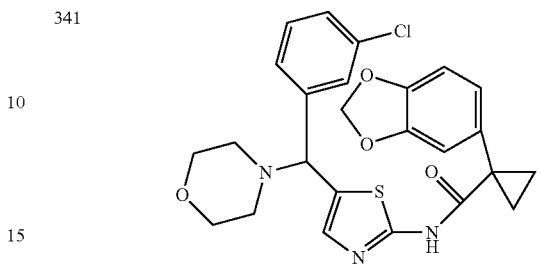 |
| 342 | 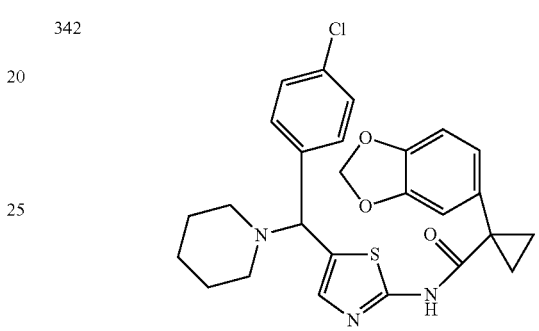 |
| 343 | 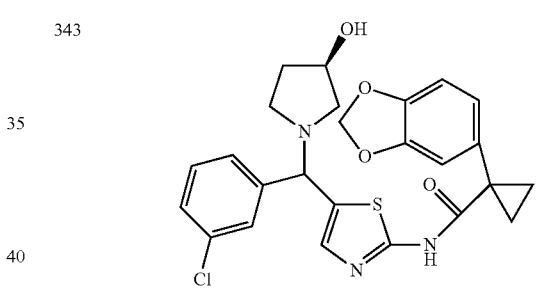 |
| 344 | 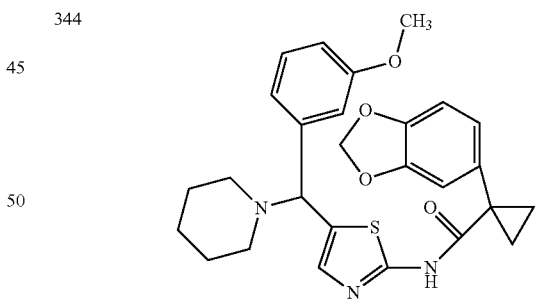 |
| 345 | 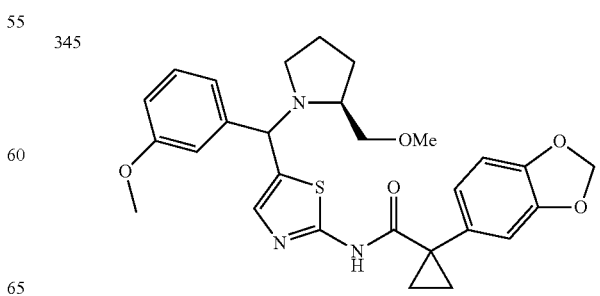 |

211
-continued

| Cmpd # | Compound |
|---|---|
| 346 | |
| 347 | |
| 348 | |
| 349 | |
| 350 | |

212
-continued

| Cmpd # | Compound |
|---|---|
| 351 | |
| 352 | |
| 353 | |
| 354 | |
| 355 | |

| Cmpd # | Compound |
|---|---|
| 356 | 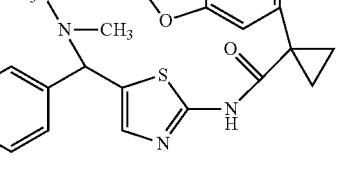 |
| 357 | 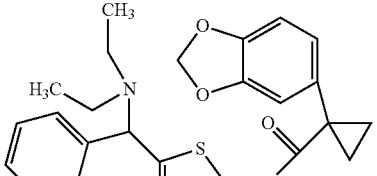 |
| 358 | 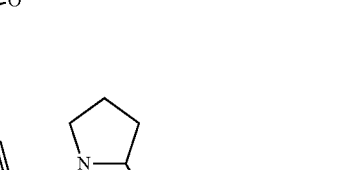 |
| 359 | 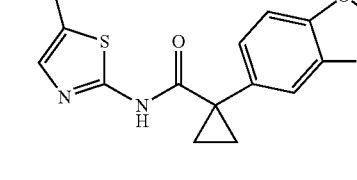 |
| 360 | 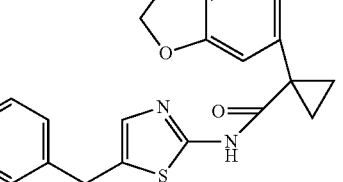 |
| Cmpd # | Compound |
|---|---|
| 361 | 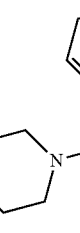 |
| 362 |  |
| 363 | 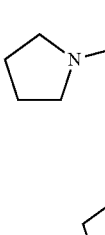 |
| 364 | 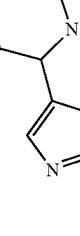 |
| 365 | 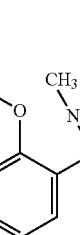 |

| Cmpd # | Compound |
|---|---|
| 366 | |
| 367 | |
| 368 | |
| 369 | |
| 370 | |

| Cmpd # | Compound |
|---|---|
| 371 | |
| 372 | |
| 373 | |
| 374 | |
| 375 | |

217
-continued
| Cmpd # | Compound |
|---|---|
| 376 | 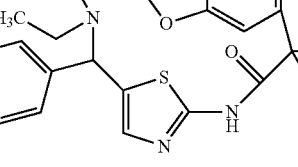 |
| 377 | 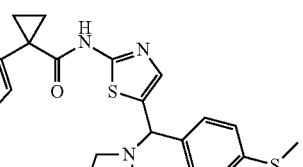 |
| 378 | 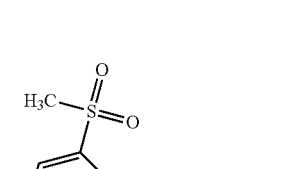 |
| 379 | 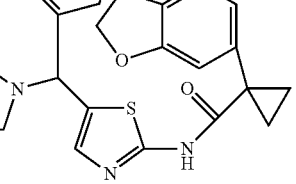 |
| 380 | 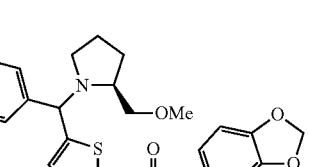 |
218
-continued
| Cmpd # | Compound |
|---|---|
| 381 | 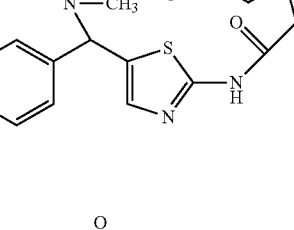 |
| 382 | 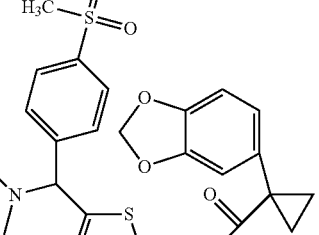 |
| 383 | 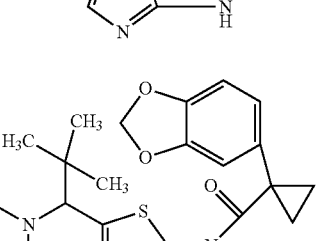 |
| 384 | 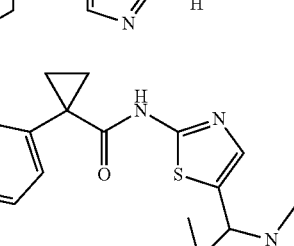 |
| 385 | 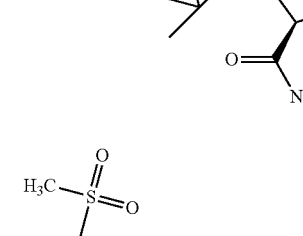 |

| Cmpd # | Compound |
|---|---|
| 386 | 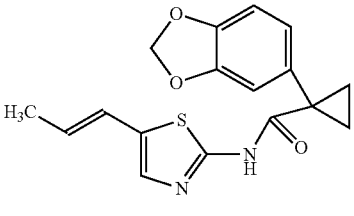 [SMILES: C/C=C/c1cnc(NC(=O)C2(c3ccc4c(c3)OCO4)CC2)s1] |
| 387 | 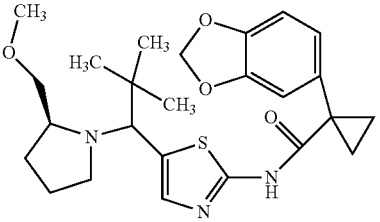 [SMILES: COC[C@@H]1CCCN1C(c1cnc(NC(=O)C2(c3ccc4c(c3)OCO4)CC2)s1)C(C)(C)C] |
| 388 | 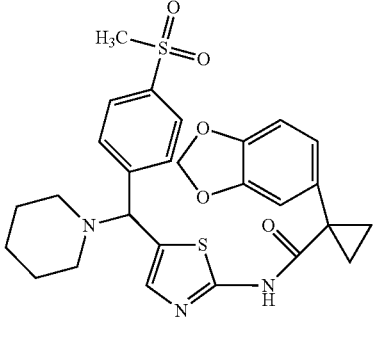 [SMILES: CS(=O)(=O)c1ccc(C(c2cnc(NC(=O)C3(c4ccc5c(c4)OCO5)CC3)s2)N2CCCCC2)cc1] |
| 389 | 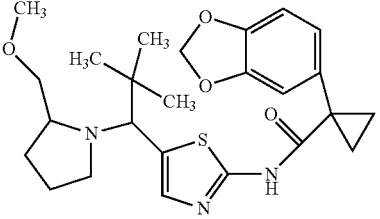 [SMILES: COCC1CCCN1C(c1cnc(NC(=O)C2(c3ccc4c(c3)OCO4)CC2)s1)C(C)(C)C] |
| 390 | 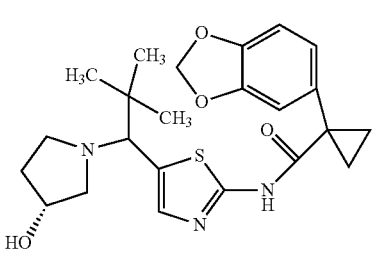 [SMILES: CC(C)(C)C(c1cnc(NC(=O)C2(c3ccc4c(c3)OCO4)CC2)s1)N1CC[C@@H](O)C1] |
| 391 | 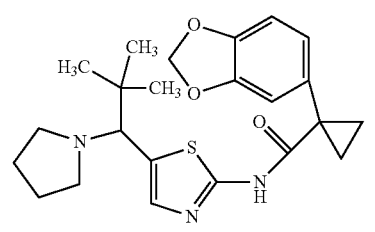 [SMILES: CC(C)(C)C(c1cnc(NC(=O)C2(c3ccc4c(c3)OCO4)CC2)s1)N1CCCC1] |
| 392 | 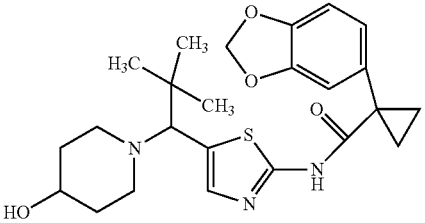 [SMILES: CC(C)(C)C(c1cnc(NC(=O)C2(c3ccc4c(c3)OCO4)CC2)s1)N1CCC(O)CC1] |
| 393 | 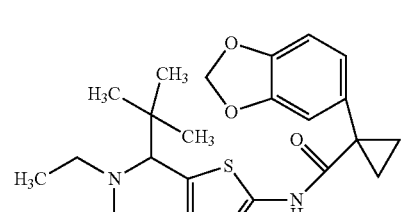 |
| 394 | 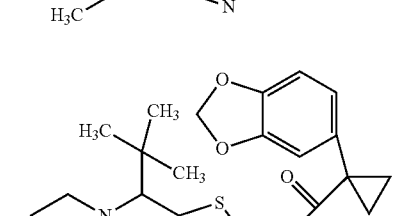 |
| 395 | 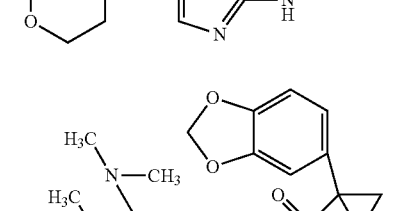 |
| 396 | 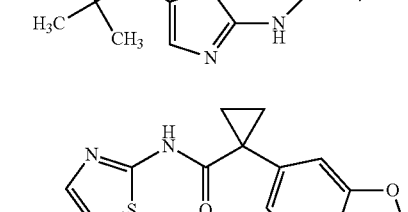 |
| 397 | 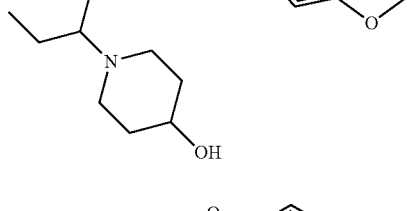 |

221
-continued
| Cmpd # | Compound |
|---|---|
| 398 | 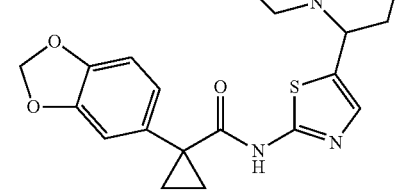 |
| 399 | 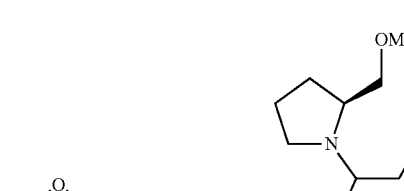 |
| 400 | 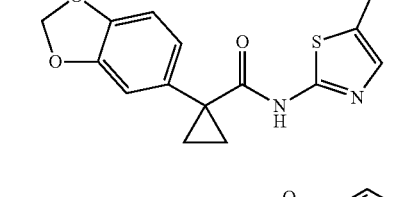 |
| 401 | 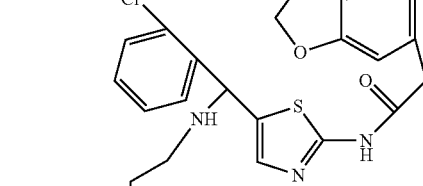 |
| 402 | 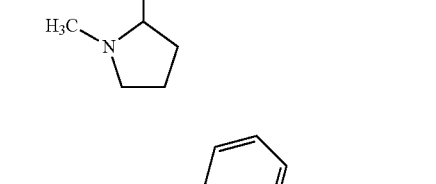 |
222
-continued
| Cmpd # | Compound |
|---|---|
| 403 | |
| 404 | |
| 405 | |
| 406 | |
| 407 | |

| Cmpd # | Compound |
|---|---|
| 408 | |
| 409 | |
| 410 | |
| 411 | |
| 412 | |
| 413 | |
| 414 | |
| 415 | |
| 416 | |
| 417 | |
| 418 | |

| Cmpd # | Compound |
|---|---|
| 419 | (structure) |
| 420 | (structure) |
| 421 | (structure) |
| 422 | (structure) |
| 423 | (structure) |
| 424 | (structure) |
| 425 | (structure) |
| 426 | (structure) |
| 427 | (structure) |
| 428 | (structure) |
| 429 | (structure) |

| Cmpd # | Compound | | Cmpd # | Compound |
|---|---|---|---|---|
| 430 | 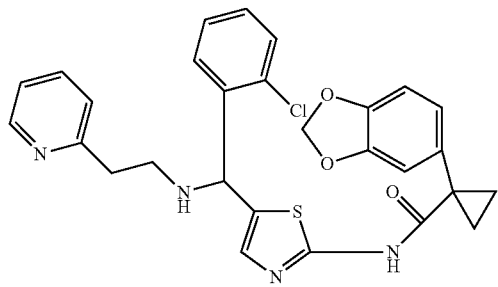 [SMILES: O=C(Nc1ncc(C(NCCc2ccccn2)c2ccccc2Cl)s1)C1(c2ccc3c(c2)OCO3)CC1] | | 435 | 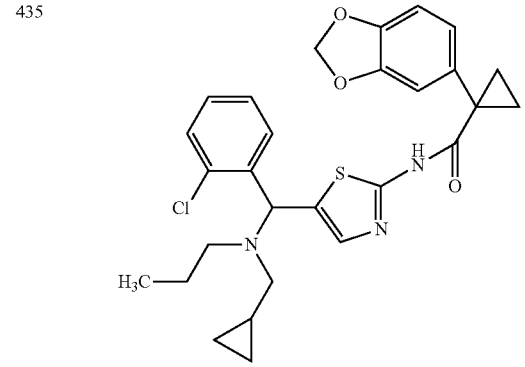 |
| 431 | 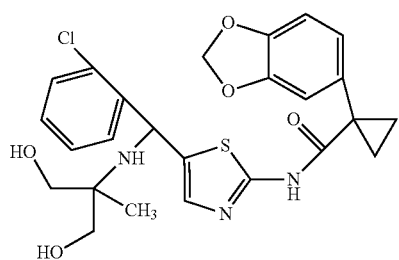 [SMILES: CC(CO)(CO)NC(c1cnc(NC(=O)C2(c3ccc4c(c3)OCO4)CC2)s1)c1ccccc1Cl] | | 436 | 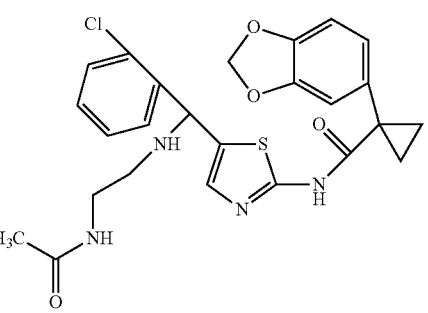 |
| 432 | 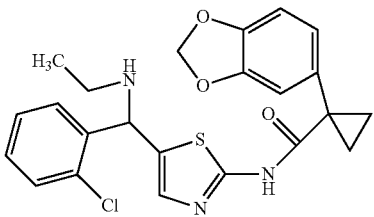 [SMILES: CCNC(c1cnc(NC(=O)C2(c3ccc4c(c3)OCO4)CC2)s1)c1ccccc1Cl] | | 437 | 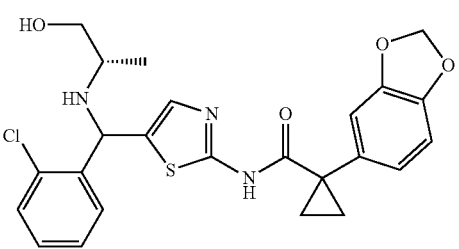 |
| 433 | 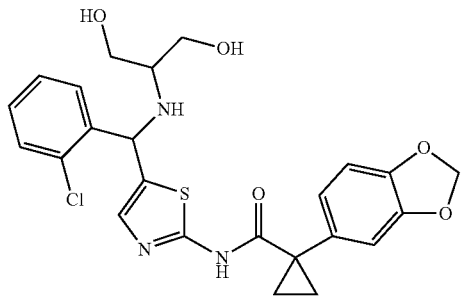 [SMILES: O=C(Nc1ncc(C(NC(CO)CO)c2ccccc2Cl)s1)C1(c2ccc3c(c2)OCO3)CC1] | | 438 | 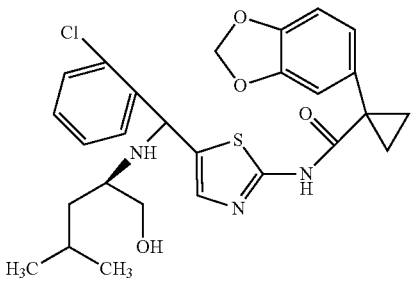 |
| 434 | 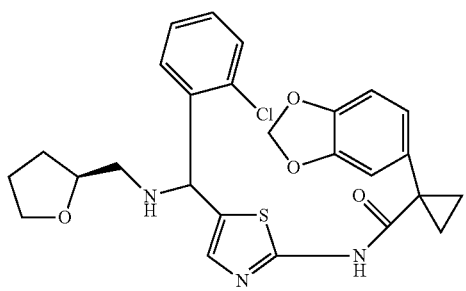 [SMILES: O=C(Nc1ncc(C(NC[C@@H]2CCCO2)c2ccccc2Cl)s1)C1(c2ccc3c(c2)OCO3)CC1] | | 439 | 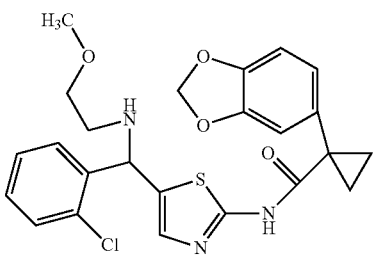 [SMILES: COCCNC(c1cnc(NC(=O)C2(c3ccc4c(c3)OCO4)CC2)s1)c1ccccc1Cl] |

| Cmpd # | Compound |
|---|---|
| 440 | 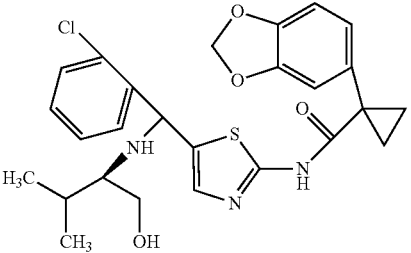 [SMILES: CC(C)[C@H](CO)NC(c1cnc(NC(=O)C2(c3ccc4c(c3)OCO4)CC2)s1)c1ccccc1Cl] |
| 441 | 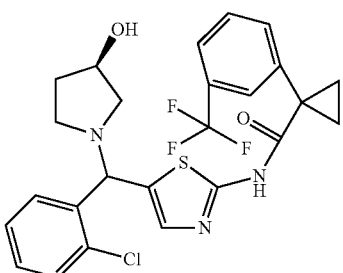 |
| 442 | 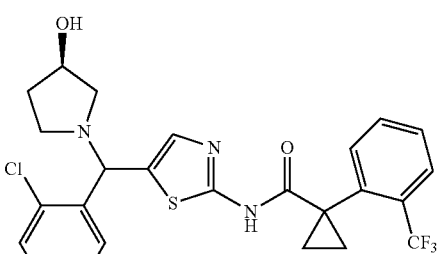 |
| 443 | 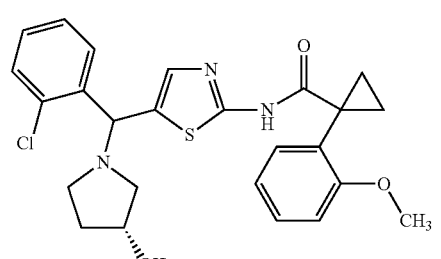 |
| 444 | 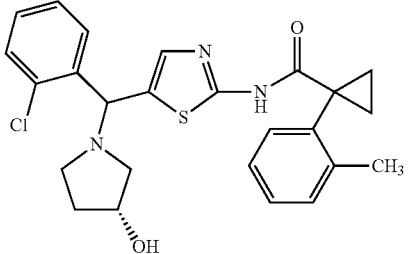 [SMILES: Cc1ccccc1C1(C(=O)Nc2ncc(C(c3ccccc3Cl)N3CC[C@@H](O)C3)s2)CC1] |
| Cmpd # | Compound |
|---|---|
| 445 | 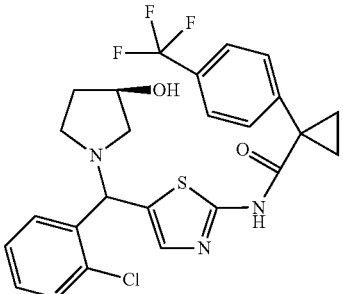 |
| 446 | 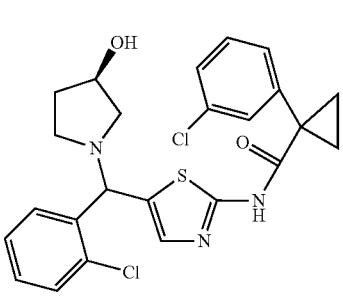 [SMILES: O=C(Nc1ncc(C(c2ccccc2Cl)N2CC[C@@H](O)C2)s1)C1(c2cccc(Cl)c2)CC1] |
| 447 | 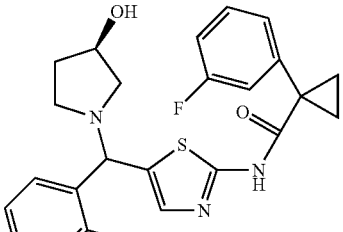 |
| 448 | 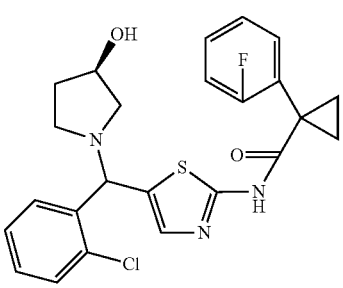 |
| 449 | 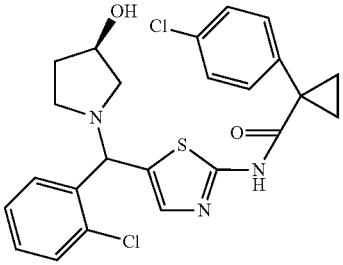 [SMILES: O=C(Nc1ncc(C(c2ccccc2Cl)N2CC[C@@H](O)C2)s1)C1(c2ccc(Cl)cc2)CC1] |

US 8,541,453 B2
-continued
| Cmpd # | Compound |
|---|---|
| 450 | 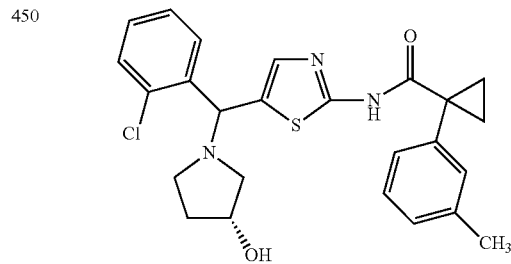 |
| 451 | 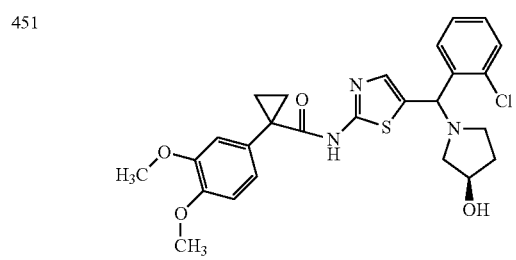 |
| 452 | 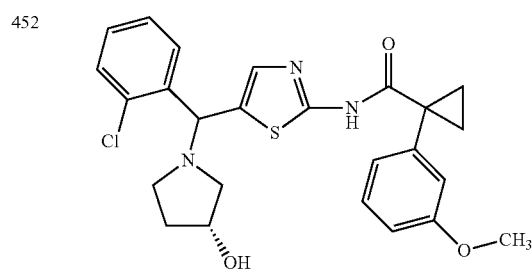 |
| 453 | 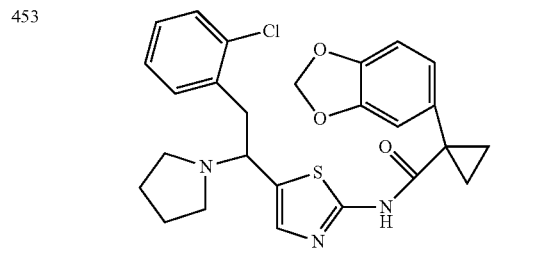 |
| 454 | 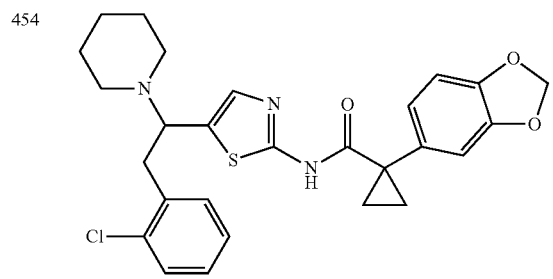 |
| 455 | 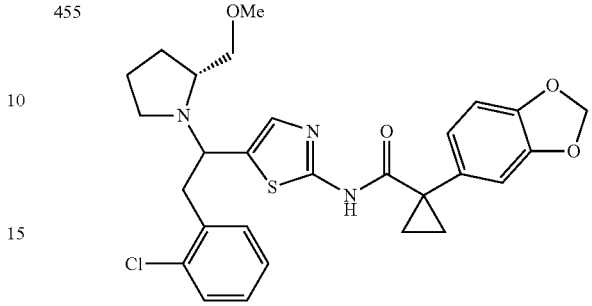 |
| 456 | 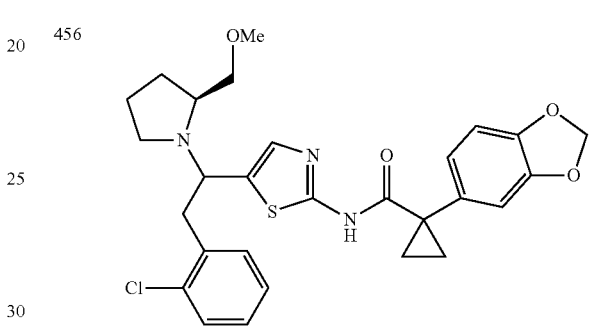 |
| 457 | 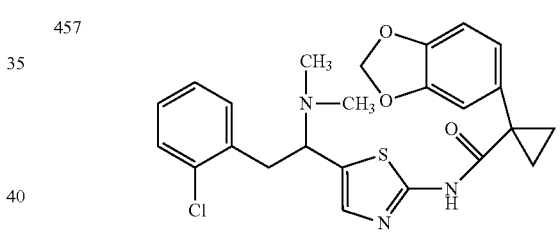 |
| 458 | 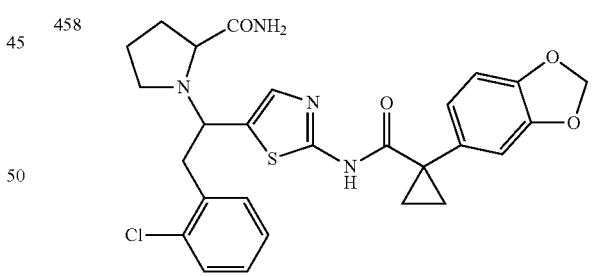 |
| 459 | 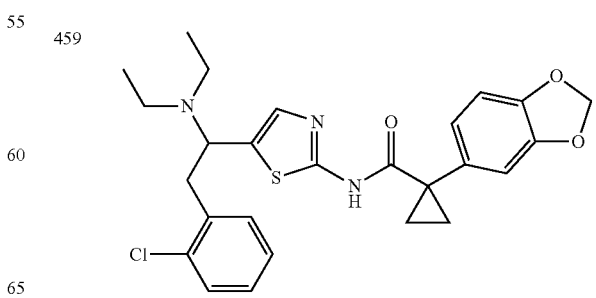 |

US 8,541,453 B2
| Cmpd # | Compound |
|---|---|
| 460 | 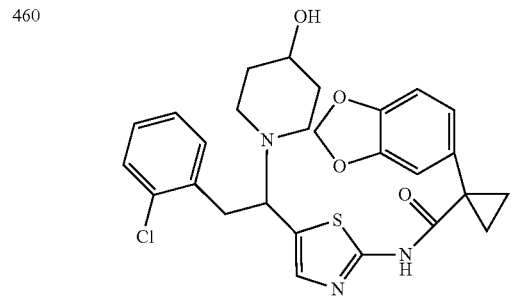 |
| 461 | 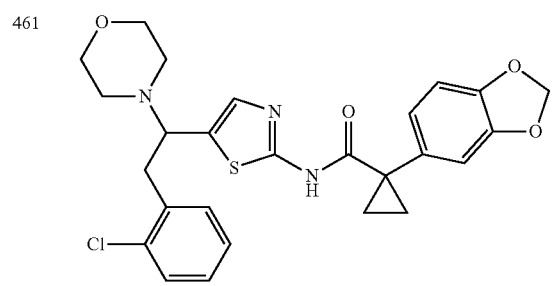 |
| 462 | 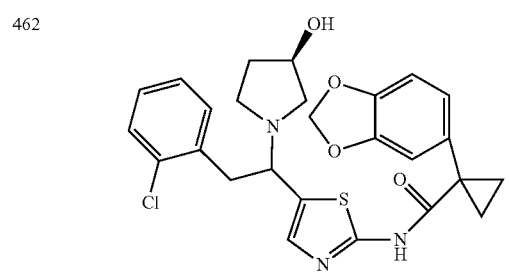 |
| 463 | 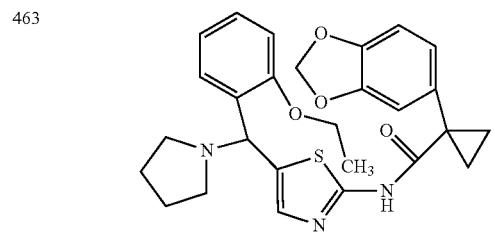 |
| 464 | 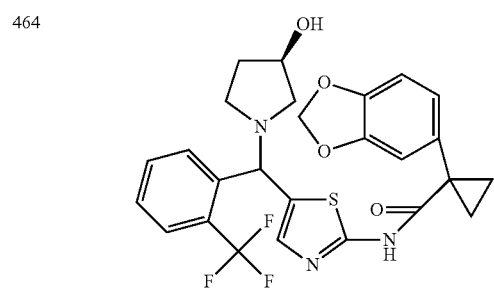 |
| Cmpd # | Compound |
|---|---|
| 465 | 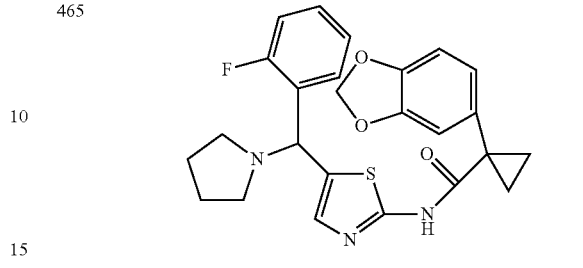 |
| 466 | 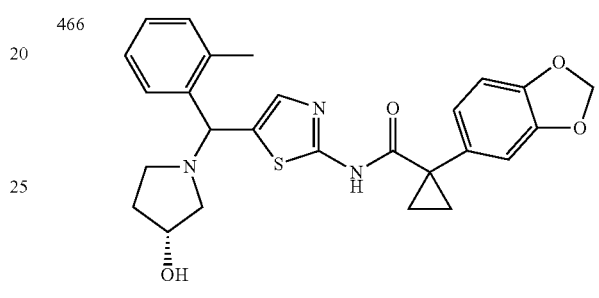 |
| 467 | 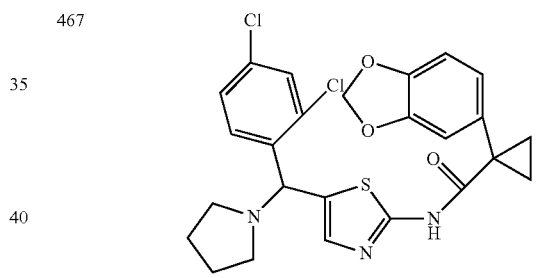 |
| 468 | 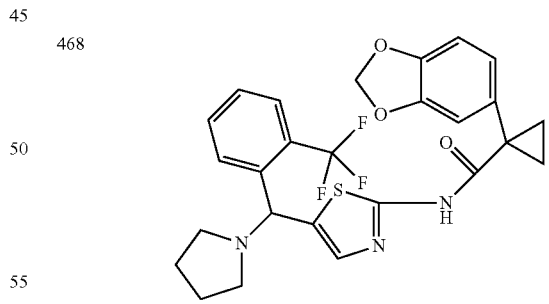 |
| 469 | 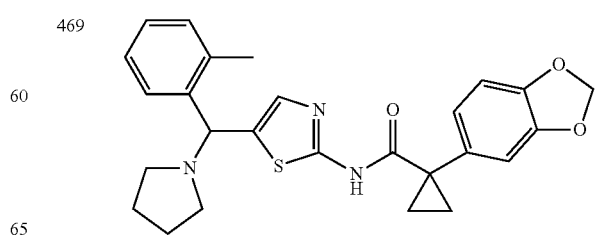 |

235
-continued

| Cmpd # | Compound |
|---|---|
| 470 | |
| 471 | |
| 472 | |
| 473 | |
| 474 | |
| 475 | |

236
-continued

| Cmpd # | Compound |
|---|---|
| 476 | |
| 477 | |
| 478 | |
| 479 | |
| 480 | |
| 481 | |

237
-continued

| Cmpd # | Compound |
|---|---|
| 482 | |
| 483 | |
| 484 | |
| 485 | |
| 486 | |
| 487 | |

238
-continued

| Cmpd # | Compound |
|---|---|
| 488 | |
| 489 | |
| 490 | |
| 491 | |
| 492 | |

| Cmpd # | Compound |
|---|---|
| 493 | 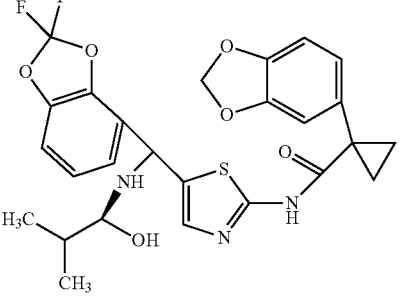 |
| 494 | 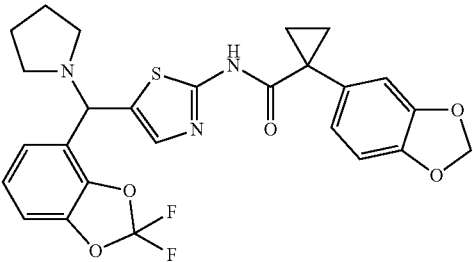 [SMILES: O=C(Nc1ncc(C(c2cccc3c2OC(F)(F)O3)N2CCCC2)s1)C1(c2ccc3c(c2)OCO3)CC1] |
| 495 | 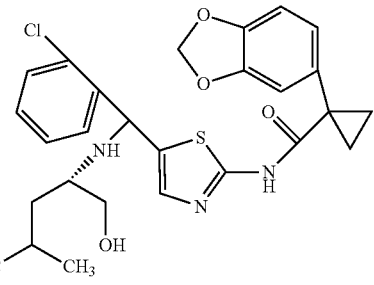 |
| 496 | 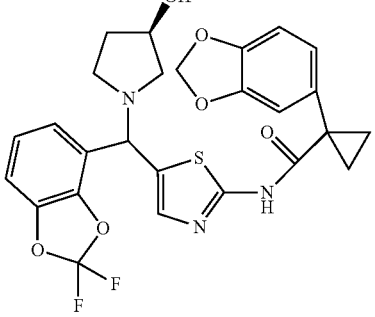 |
| 497 | 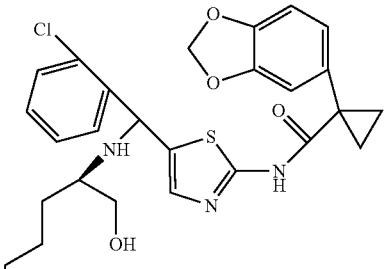 |
| 498 | 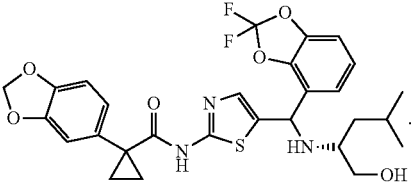 |
30. The method of claim 3, wherein $XR^X$ is hydrogen.
31. The method of claim 3, wherein $ZR^Z$ is selected from halo, $CF_3$, $OCF_3$, C1-C4 alkoxy, methylenedioxy, or difluoromethylenedioxy.
32. The method of claim 3, wherein z is 1-3.
33. The method of claim 3, wherein the compound is
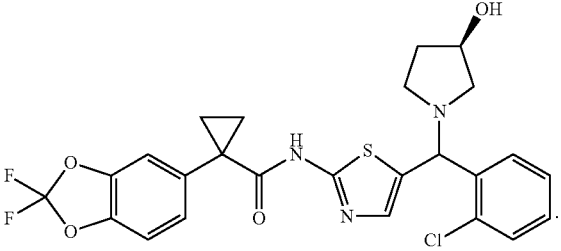 [SMILES: O=C(Nc1ncc(C(c2ccccc2Cl)N2CC[C@@H](O)C2)s1)C1(c2ccc3c(c2)OC(F)(F)O3)CC1]
* * * * *